(12) United States Patent
Rodino-Klapac et al.

(10) Patent No.: US 11,925,675 B2
(45) Date of Patent: Mar. 12, 2024

(54) SYSTEMIC DELIVERY OF ADENO-ASSOCIATED VIRUS VECTOR EXPRESSING GAMMA-SARCOGLYCAN AND THE TREATMENT OF MUSCULAR DYSTROPHY

(71) Applicant: Sarepta Therapeutics, Inc., Cambridge, MA (US)

(72) Inventors: Louise Rodino-Klapac, Cambridge, MA (US); Eric Pozsgai, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 72 days.

(21) Appl. No.: 17/468,086

(22) Filed: Sep. 7, 2021

(65) Prior Publication Data
US 2022/0088123 A1   Mar. 24, 2022

Related U.S. Application Data

(60) Provisional application No. 63/075,697, filed on Sep. 8, 2020.

(51) Int. Cl.
| | |
|---|---|
| *A61P 21/00* | (2006.01) |
| *A61K 38/17* | (2006.01) |
| *A61K 48/00* | (2006.01) |
| *C07K 14/705* | (2006.01) |
| *C12N 15/86* | (2006.01) |

(52) U.S. Cl.
CPC ........ *A61K 38/177* (2013.01); *A61K 48/0058* (2013.01); *A61K 48/0066* (2013.01); *A61P 21/00* (2018.01); *C07K 14/705* (2013.01); *C12N 15/86* (2013.01); *C12N 2750/14143* (2013.01); *C12N 2750/14171* (2013.01)

(58) Field of Classification Search
CPC .............. A61K 38/177; A61K 48/0058; A61K 48/0066; A61P 21/00; C07K 14/705; C07K 14/4707; C12N 15/86; C12N 2750/14143; C12N 2750/14171; C12N 2830/008
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 2020/0360534 A1* | 11/2020 | Rodino-Klapac | ................... C07K 14/4707 |
| 2023/0040544 A1* | 2/2023 | Pozsgai | ................... A61P 21/00 |
| 2023/0256117 A1* | 8/2023 | Richard | ............. A61K 48/0058 514/44 R |

FOREIGN PATENT DOCUMENTS

| | | |
|---|---|---|
| WO | WO-9513365 A1 | 5/1995 |
| WO | WO-9513392 A1 | 5/1995 |
| WO | WO-9617947 A1 | 6/1996 |
| WO | WO-9706243 A1 | 2/1997 |
| WO | WO-9708298 A1 | 3/1997 |
| WO | WO-9709441 A2 | 3/1997 |
| WO | WO-9721825 A1 | 6/1997 |
| WO | WO-9809657 A2 | 3/1998 |
| WO | WO-9911764 A2 | 3/1999 |
| WO | WO-0183692 A2 | 11/2001 |
| WO | WO-02053703 A2 | 7/2002 |
| WO | WO-2019152474 A1 | 8/2019 |
| WO | WO-2020176614 A1 | 9/2020 |

OTHER PUBLICATIONS

Pozsgai, E. R., Griffin, D. A., Heller, K. N., Mendell, J. R., & Rodino-Klapac, L. R. (2017). Systemic AAV-mediated β-sarcoglycan delivery targeting cardiac and skeletal muscle ameliorates histological and functional deficits in LGMD2E mice. Molecular Therapy, 25(4), 855-869. (Year: 2017).*
Israeli, D., Cosette, J., Corre, G., Amor, F., Poupiot, J., Stockholm, D., . . . & Richard, I. (2019). An AAV-SGCG dose-response study in a γ-sarcoglycanopathy mouse model in the context of mechanical stress. Molecular Therapy-Methods & Clinical Development, 13 , 494-502. (Year: 2019).*
Zygmunt, D. A., Xu, R., Jia, Y., Ashbrook, A., Menke, C., Shao, G., . . . & Martin, P. T. (2019). rAAVrh74. MCK. GALGT2 demonstrates safety and widespread muscle glycosylation after intravenous delivery in C57BL/6J mice. Molecular Therapy-Methods & Clinical Development, 15, 305-319. (Year: 2019).*
Anderson, M. L. M., and Young, B. D., "Chapter 4: Quantitative Filter Hybridisation," in *Nucleic Acid Hybridisation: A Practical Approach*, pp. 73-111, Hames, B. D., et al., eds., IRL Press Ltd., United Kingdom (1985).
Blacklowe, N. R., "Chapter 11: Adeno-Associated Viruses of Humans," in *Parvoviruses and Human Disease*, pp. 165-174, Pattison, J. R., ed., CRC Press, Inc., United States (1988).
Carter, B. J., et al., "Chapter 11: AAV DNA replication, integration, and genetics," in *CRC Handbook of Parvoviruses*, vol. 1, pp. 169-226, Tijssen, P., ed., CRC Press, Inc., United States (1989).

(Continued)

*Primary Examiner* — Neil P Hammell
*Assistant Examiner* — Khaleda B Hasan
(74) *Attorney, Agent, or Firm* — Sterne, Kessler, Goldstein & Fox P.L.L.C.

(57) ABSTRACT

Described herein are methods of treating muscular dystrophy comprising administering to a subject a recombinant AAV (rAAV) scAAVrh74.MHCK7.hSGCG vector, methods of expressing gamma-sarcoglycan gene in a patient, pharmaceutical compositions comprising the rAAV scAAVrh74.MHCK7.hSGCG for usage in such methods, the doses and the ranges thereof for such methods, and methods of generating and producing the rAAV scAAVrh74.MHCK7.hSGCG.

14 Claims, 13 Drawing Sheets
(11 of 13 Drawing Sheet(s) Filed in Color)
Specification includes a Sequence Listing.

(56) References Cited

OTHER PUBLICATIONS

Carter, B. J., "Adeno-associated virus vectors," Curr Opin Biotechnol 3(5):533-539, Elsevier, Netherlands (Oct. 1992).

Clark, K. R., et al., "A stable cell line carrying adenovirus-inducible rep and cap genes allows for infectivity titration of adeno-associated virus vectors," Gene Ther 3(12):1124-1132, Nature Publishing Group, United Kingdom (Dec. 1996).

Clark, K. R., et al., "Highly purified recombinant adeno-associated virus vectors are biologically active and free of detectable helper and wild-type viruses," Hum Gene Ther 10(6):1031-1039, Mary Ann Liebert Inc., United States (Apr. 1999).

Cserjesi, P., and Olson, E. N., "Myogenin induces the myocyte-specific enhancer binding factor MEF-2 independently of other muscle-specific gene products," Mol Cell Biol 11(10):4854-4862, American Society of Microbiology, United States (Oct. 1991).

Hakim, C. H., et al., "Evaluation of Muscle Function of the Extensor Digitorum Longus Muscle Ex vivo and Tibialis Anterior Muscle In situ in Mice," Journal of Visualized Experiments 72:50183, 8 pages, MYJoVE Corporation, United States (2013).

Hermonat, P. L., and Muzyczka, N., "Use of adeno-associated virus as a mammalian DNA cloning vector: transduction of neomycin resistance into mammalian tissue culture cells," Proc Natl Acad Sci USA 81(20):6466-6470, National Academy of Sciences, United States (Oct. 1984).

Johnson, J. E., et al., "Muscle creatine kinase sequence elements regulating skeletal and cardiac muscle expression in transgenic mice," Mol Cell Biol 9(8):3393-3399, American Society of Microbiology, United States (Aug. 1989).

Laughlin, C. A., et al., "Cloning of infectious adeno-associated virus genomes in bacterial plasmids," Gene 23(1):65-73, Elsevier, Netherlands (Jul. 1983).

Lebkowski, J. S., et al., "Adeno-associated virus: a vector system for efficient introduction and integration of DNA into a variety of mammalian cell types," Mol Cell Biol 8(10):3988-3996, American Society of Microbiology, United States (Oct. 1988).

Mader, S., and White, J. H., "A steroid-inducible promoter for the controlled overexpression of cloned genes in eukaryotic cells," Proc Natl Acad Sci USA 90(12):5603-5607, National Academy of Sciences, United States (Jun. 1993).

Marsic, D., et al., "Vector design Tour de Force: integrating combinatorial and rational approaches to derive novel adeno-associated virus variants," Mol Ther 22(11):1900-1909, Cell Press, United States (Nov. 2014).

McLaughlin, S. K., et al., "Adeno-associated virus general transduction vectors: analysis of proviral structures," J Virol 62(6):1963-1973, American Society of Microbiology, United States (Jun. 1988).

Muscat, G. E., and Kedes, L., "Multiple 5'-flanking regions of the human alpha-skeletal actin gene synergistically modulate muscle-specific expression," Mol Cell Biol 7(11):4089-4099, American Society of Microbiology, United States (Nov. 1987).

Muzyczka, N., "Use of adeno-associated virus as a general transduction vector for mammalian cells," Curr Top Microbiol Immunol 158:97-129, Springer Verlag, Germany (1992).

Paul, R. W., et al., "Increased viral titer through concentration of viral harvests from retroviral packaging lines," Hum Gene Ther 4(5):609-614, Mary Ann Liebert, Inc., United States (Oct. 1993).

Perrin, P., et al., "An experimental rabies vaccine produced with a new BHK-21 suspension cell culture process: use of serum-free medium and perfusion-reactor system," Vaccine 13(13):1244-1250, Elsevier, Netherlands (Sep. 1995).

Rodino-Klapac, L. R., et al., "A translational approach for limb vascular delivery of the micro-dystrophin gene without high volume or high pressure for treatment of Duchenne muscular dystrophy," J Transl Med 5:45, 11 pages, Biomed Central, United Kingdom (Sep. 2007).

Rose, J. A., "Chapter 1: Parvovirus Reproduction," in *Comprehensive Virology*, vol. 3, pp. 1-61, Heinz, F.-C., et al., eds., Plenum Press, United States (1974).

Samulski, R. J., et al., "Cloning of adeno-associated virus into pBR322: rescue of intact virus from the recombinant plasmid in human cells," Proc Natl Acad Sci USA 79(6):2077-2081, National Academy of Sciences, United States (Mar. 1982).

Samulski, R. J., et al., "Helper-free stocks of recombinant adeno-associated viruses: normal integration does not require viral gene expression," J Virol 63(9):3822-3828, American Society for Microbiology, United States (Sep. 1989).

Schnepp, B., and Clark, K. R., "Highly purified recombinant adeno-associated virus vectors. Preparation and quantitation," Methods in Molecular Medicine 69:427-443, Humana Press, United States (2002).

Semenza, G. L., et al., "Hypoxia-inducible nuclear factors bind to an enhancer element located 3' to the human erythropoietin gene," Proc Natl Acad Sci USA 88(13):5680-5684, National Academy of Sciences, United States (Jul. 1991).

Senapathy, P., and Carter, B. J., "Molecular cloning of adeno-associated virus variant genomes and generation of infectious virus by recombination in mammalian cells," J Biol Chem 259(7):4661-4666, Elsevier, Netherlands (Apr. 1984).

Tratschin, J. D., et al., "A human parvovirus, adeno-associated virus, as a eucaryotic vector: transient expression and encapsidation of the procaryotic gene for chloramphenicol acetyltransferase," Mol Cell Biol 4(10):2072-2081, American Society of Microbiology, United States (Oct. 1984).

Tratschin, J. D., et al., "Adeno-associated virus vector for high-frequency integration, expression, and rescue of genes in mammalian cells," Mol Cell Biol 5(11):3251-3260, American Society of Microbiology, United States (Nov. 1985).

Weintraub, H., et al., "The myoD gene family: nodal point during specification of the muscle cell lineage," Science 251(4995):761-766, American Association for the Advancement of Science, United States (Feb. 1991).

Cordier, L., et al., "Muscle-specific promoters may be necessary for adeno-associated virus-mediated gene transfer in the treatment of muscular dystrophies," *Hum. Gene Ther*. 12(2):205-215, Mary Ann Liebert, United States (Jan. 2001).

International Search Report and Written Opinion for International Appl. No. PCT/US2021/048957, European Patent Office, Netherlands, dated Dec. 23, 2021, 14 pages.

Pozsgai, E., et al., "Systemic gene therapy restores [gamma]-sarcoglycan expression in skeletal and cardiac muscle in LGMD2C mice," *Mol. Ther*. 26(5):S1, Cell Press, United States (2018).

Seo, Y.E., et al., "Systemic Dose-Finding Study with AAV-Mediated [gamma]-Sarcoglycan Gene Therapy for Treatment of Muscle Deficits in LGMD2C Mice," *25th International Annual Congress of the World Muscle Society*, p. 138, United States, Sep. 30-Oct. 2, 2020; accessed at URL: https://investorrelations.sarepta.com/static-files/12c957cb-7203-4110-b7fd-a69182d7ac09 on Sep. 30, 2022.

Seo, Y.E., et al., p. 138 "Systemic dose-finding study with AAV-mediated Gamma-sarcoglycan gene therapy for treatment of muscle deficits in LGMD2C Mice," *Neuromuscular Disorders* 30:138, Elsevier, Netherlands (2020).

\* cited by examiner $*p < 0.05; p < 0.01; *p < 0.001; ****p < 0.0001$

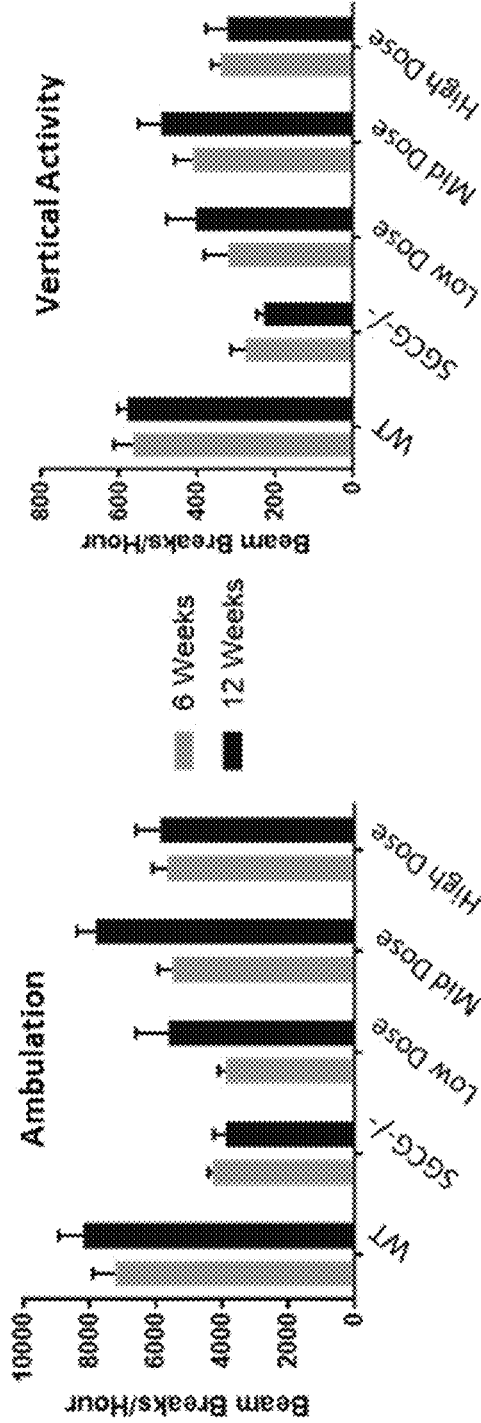
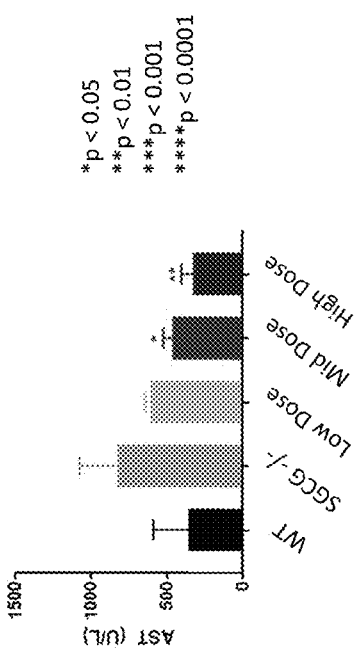
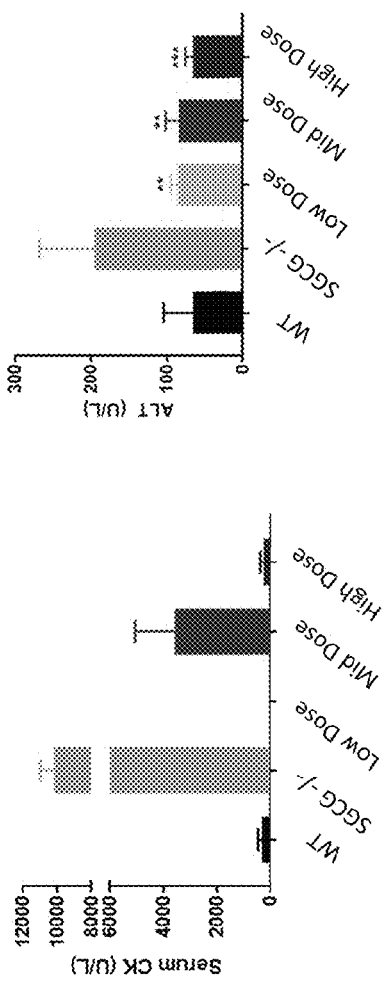

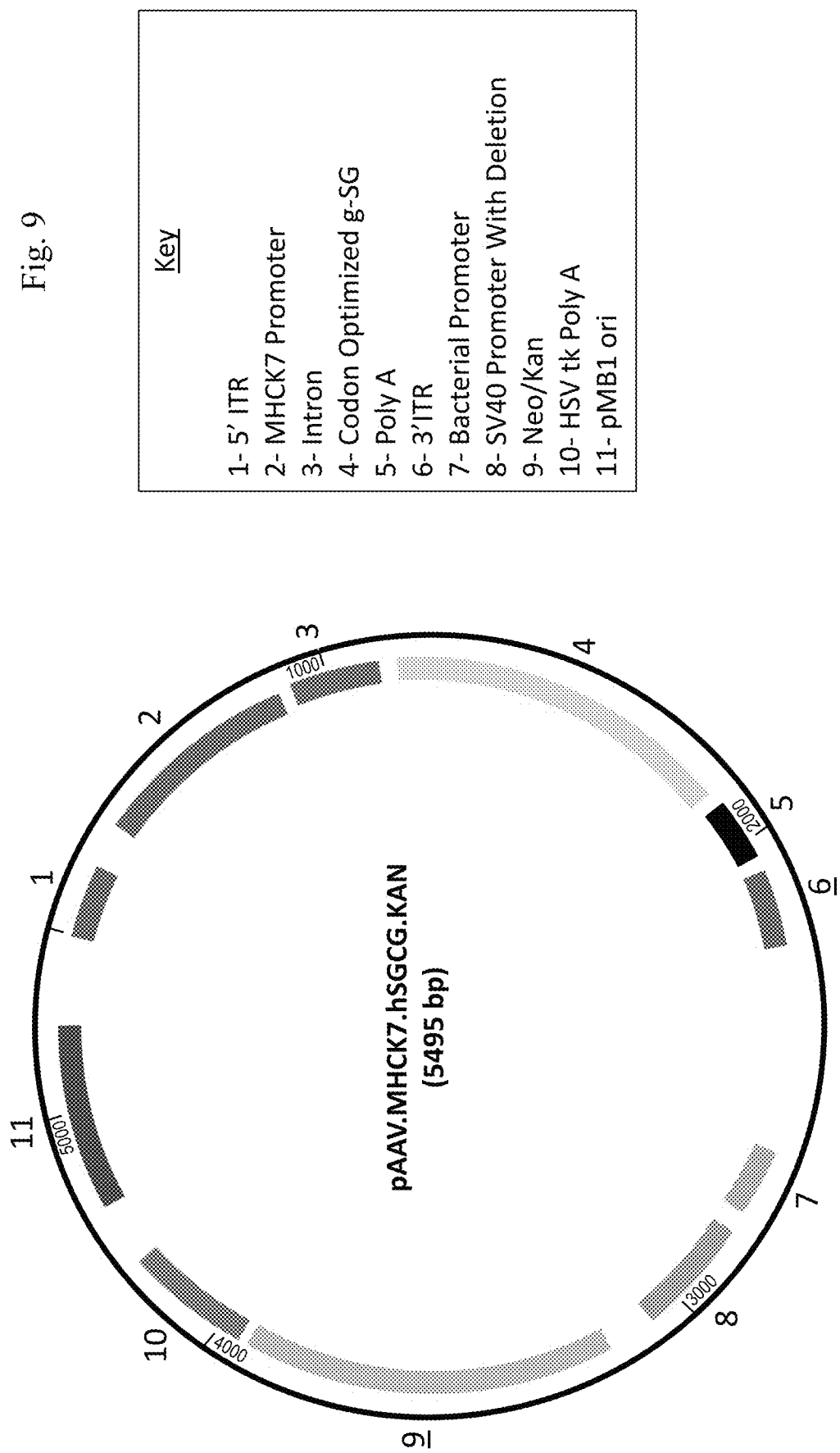

```
                         SEQUENCE LISTING

<160> NUMBER OF SEQ ID NOS: 15

<210> SEQ ID NO 1
<211> LENGTH: 876
<212> TYPE: DNA
<213> ORGANISM: Artificial Sequence
<220> FEATURE:
<223> OTHER INFORMATION: Human Gamma-Sarcoglycan nucleotide sequence
      (codon-optimized)

<400> SEQUENCE: 1
atggtgaggg agcagtacac cacagcaacc gagggaatct gcatcgagag gccagagaac      60
cagtacgtgt ataagatcgg catctacggc tggcggaaga gatgtctgta tctgttcgtg     120
ctgctgctgc tgatcatcct ggtggtgaat ctggccctga ccatctggat cctgaaagtg     180
atgtggtttt ccccagcagg aatgggacac ctgtgcgtga caaaggacgg actgcggctg     240
gagggagagt ctgagttcct gtttcccctg tatgccaagg agatccacag cagagtggat     300
agctccctgc tgctgcagtc cacccagaac gtgacagtga acgcaaggaa tagcgaggga     360
gaggtgaccg gcagactgaa ggtcggcccc aagatggtgg aggtgcagaa tcagcagttc     420
cagatcaact ccaatgacgg caagcctctg tttacagtgg atgagaagga ggtggtggtg     480
ggcaccgaca agctgagggt gacaggacct gagggcgccc tgttcgagca ctctgtggag     540
accccactgg tgcgcgcaga ccctttcag gatctgaggc tggagagccc aacacgcagc     600
ctgtccatgg acgcacccag aggcgtgcac atccaggcac acgcaggcaa gatcgaggcc     660
ctgagccaga tggatatcct gttccactct agcgacggca tgctggtgct ggatgccgag     720
accgtgtgcc tgcctaagct ggtgcagggc acatggggcc catctggctc ctctcagagc     780
ctgtacgaga tctgcgtgtg cccagatggc aagctgtatc tgtccgtggc cggcgtgtct     840
accacatgcc aggagcacaa ccacatctgt ctgtga                               876

<210> SEQ ID NO 2
<211> LENGTH: 792
<212> TYPE: DNA
<213> ORGANISM: Artificial Sequence
<220> FEATURE:
<223> OTHER INFORMATION: MHCK7 promoter sequence

<400> SEQUENCE: 2
aagcttgcat gtctaagcta gacccttcag attaaaaata actgaggtaa gggcctgggt      60
aggggaggtg gtgtgagacg ctcctgtctc tcctctatct gcccatcggc cctttgggga     120
ggaggaatgt gcccaaggac taaaaaaagg ccatggagcc agagggcga gggcaacaga     180 cctttcatgg gcaaaccttg gggccctgct gtctagcatg ccccactacg ggtctaggct     240
gcccatgtaa ggaggcaagg cctggggaca cccgagatgc ctggttataa ttaacccaga     300
catgtggctg cccccccccc cccaacacct gctgcctcta aaaataaccc tgtccctggt     360
ggatcccctg catgcgaaga tcttcgaaca aggctgtggg ggactgaggg caggctgtaa     420
caggcttggg ggccagggct tatacgtgcc tgggactccc aaagtattac tgttccatgt     480
```

```
tcccggcgaa gggccagctg tccccgcca gctagactca gcacttagtt taggaaccag    540
tgagcaagtc agcccttggg gcagcccata caaggccatg ggctgggca agctgcacgc    600 ctgggtccgg ggtgggcacg gtgcccgggc aacgagctga aagctcatct gctctcaggg    660 gccctccct ggggacagcc cctcctggct agtcacaccc tgtaggctcc tctatataac    720
ccaggggcac aggggctgcc ctcattctac caccacctcc acagcacaga cagacactca    780
ggagcagcca gc                                                        792

<210> SEQ ID NO 3
<211> LENGTH: 106
<212> TYPE: DNA
<213> ORGANISM: Artificial Sequence
<220> FEATURE:
<223> OTHER INFORMATION: 5' ITR

<400> SEQUENCE: 3
ctgcgcgctc gctcgctcac tgaggccgcc cgggcaaagc ccgggcgtcg ggcgaccttt    60
ggtcgcccgg cctcagtgag cgagcgagcg cgcagagagg gagtgg                   106

<210> SEQ ID NO 4
<211> LENGTH: 130
<212> TYPE: DNA
<213> ORGANISM: Artificial Sequence
<220> FEATURE:
<223> OTHER INFORMATION: 3' ITR

<400> SEQUENCE: 4
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag                                                          130

<210> SEQ ID NO 5
<211> LENGTH: 53
<212> TYPE: DNA
<213> ORGANISM: Artificial Sequence
<220> FEATURE:
<223> OTHER INFORMATION: Poly A sequence

<400> SEQUENCE: 5
ggccgcaata aaagatcttt attttcatta gatctgtgtg ttggttttttt gtg          53

<210> SEQ ID NO 6
<211> LENGTH: 148
<212> TYPE: DNA
<213> ORGANISM: Artificial Sequence
<220> FEATURE:
<223> OTHER INFORMATION: Intron Sequence

<400> SEQUENCE: 6
aggtaagttt agtcttttg tcttttattt caggtcccgg atccggtggt ggtgcaaatc    60
aaagaactgc tcctcagtgg atgttgcctt tacttctagg cctgtacgga agtgttactt    120
ctgctctaaa agctgcggaa ttgtaccc                                       148

<210> SEQ ID NO 7
<211> LENGTH: 2225
<212> TYPE: DNA
<213> ORGANISM: Artificial Sequence
<220> FEATURE:
<223> OTHER INFORMATION: Expression cassette polynucleotide sequence
      5'ITR Through 3'ITR
```

```
<400> SEQUENCE: 7
ctgcgcgctc gctcgctcac tgaggccgcc cgggcaaagc ccgggcgtcg ggcgaccttt      60
ggtcgcccgg cctcagtgag cgagcgagcg cgcagagagg gagtgggggtt aaccaattgg    120 cggccgcaag cttgcatgtc taagctagac ccttcagatt aaaaataact gaggtaaggg    180
cctgggtagg ggaggtggtg tgagacgctc ctgtctctcc tctatctgcc catcggccct    240
ttggggagga ggaatgtgcc caaggactaa aaaaaggcca tggagccaga ggggcgaggg    300
caacagacct ttcatgggca aaccttgggg ccctgctgtc tagcatgccc cactacgggt    360
ctaggctgcc catgtaagga ggcaaggcct ggggacaccc gagatgcctg gttataatta    420
acccagacat gtggctgccc cccccccccc aacacctgct gcctctaaaa ataaccctgt    480
ccctggtgga tcccctgcat gcgaagatct tcgaacaagg ctgtggggga ctgagggcag    540
gctgtaacag gcttggggggc cagggcttat acgtgcctgg gactcccaaa gtattactgt    600
tccatgttcc cggcgaaggg ccagctgtcc cccgccagct agactcagca cttagtttag    660
gaaccagtga gcaagtcagc ccttggggca gcccatacaa ggccatgggg ctgggcaagc    720
tgcacgcctg ggtccggggt gggcacggtg cccgggcaac gagctgaaag ctcatctgct    780
ctcaggggcc cctccctggg gacagcccct cctggctagt cacaccctgt aggctcctct    840
atataaccca ggggcacagg ggctgccctc attctaccac cacctccaca gcacagacag    900
acactcagga gcagccagcg gcgcgcccag gtaagtttag tctttttgtc ttttatttca    960
ggtcccggat ccggtggtgg tgcaaatcaa agaactgctc ctcagtggat gttgccttta   1020
cttctaggcc tgtacggaag tgttacttct gctctaaaag ctgcggaatt gtacccggta   1080
ccaccatggt gagggagcag tacaccacag caaccgaggg aatctgcatc gagaggccag   1140
agaaccagta cgtgtataag atcggcatct acggctggcg gaagagatgt ctgtatctgt   1200
tcgtgctgct gctgctgatc atcctggtgg tgaatctggc cctgaccatc tggatcctga   1260
aagtgatgtg gttttcccca gcaggaatgg gacacctgtg cgtgacaaag gacggactgc   1320
ggctggaggg agagtctgag ttcctgtttc ccctgtatgc caaggagatc cacagcagag   1380
tggatagctc cctgctgctg cagtccaccc agaacgtgac agtgaacgca aggaatagcg   1440
agggagaggt gaccggcaga ctgaaggtcg gccccaagat ggtggaggtg cagaatcagc   1500
agttccagat caactccaat gacggcaagc ctctgttta cagtggatgag aaggaggtgg   1560 tggtgggcac cgacaagctg agggtgacag gacctgaggg cgccctgttc gagcactctg   1620
tggagacccc actggtgcgc gcagaccctt ttcaggatct gaggctggag agcccaacac   1680
gcagcctgtc catggacgca cccagaggcg tgcacatcca ggcacacgca ggcaagatcg   1740
aggccctgag ccagatggat atcctgttcc actctagcga cggcatgctg gtgctggatg   1800
ccgagaccgt gtgcctgcct aagctggtgc agggcacatg gggcccatct ggctcctctc   1860
agagcctgta cgagatctgc gtgtgcccag atggcaagct gtatctgtcc gtggccggcg   1920
tgtctaccac atgccaggag cacaaccaca tctgtctgtg actcgagggc cgcaataaaa   1980
gatctttatt ttcattagat ctgtgtgttg gttttttgtg tgtcctgcag gggcgcgcct   2040
aatctagagc atggctacgt agataagtag catggcgggt taatcattaa ctacaaggaa   2100
cccctagtga tggagttggc cactccctct ctgcgcgctc gctcgctcac tgaggccggg   2160
cgaccaaagg tcgcccgacg cccgggcttt gcccgggcgg cctcagtgag cgagcgagcg   2220
cgcag                                                               2225
```

```
<210> SEQ ID NO 8
<211> LENGTH: 5495
<212> TYPE: DNA
<213> ORGANISM: Artificial Sequence
<220> FEATURE:
<223> OTHER INFORMATION: pAAV.MHCK7.hSGCG. KAN plasmid sequence

<400> SEQUENCE: 8
cagctgcgcg ctcgctcgct cactgaggcc gcccgggcaa agcccggggcg tcgggcgacc      60 tttggtcgcc cggcctcagt gagcgagcga gcgcgcagag agggagtggg gttaaccaat     120
tggcggccgc aagcttgcat gtctaagcta gacccttcag attaaaaata actgaggtaa     180
gggcctgggt aggggaggtg gtgtgagacg ctcctgtctc tcctctatct gcccatcggc     240
cctttgggga ggaggaatgt gcccaaggac taaaaaaagg ccatggagcc agagggcga      300 gggcaacaga cctttcatgg gcaaaccttg gggccctgct gtctagcatg ccccactacg     360
ggtctaggct gcccatgtaa ggaggcaagg cctggggaca cccgagatgc tggttataa     420 ttaacccaga catgtggctg ccccccccccc ccaacacct gctgcctcta aaaataaccc    480
tgtccctggt ggatcccctg catgcgaaga tcttcgaaca aggctgtggg ggactgaggg     540
caggctgtaa caggcttggg ggccagggct tatacgtgcc tgggactccc aaagtattac     600
tgttccatgt tcccggcgaa gggccagctg tcccccgcca gctagactca gcacttagtt     660
taggaaccag tgagcaagtc agcccttggg gcagcccata caaggccatg gggctgggca     720
agctgcacgc ctgggtccgg ggtgggcacg gtgcccgggc aacgagctga aagctcatct     780
gctctcaggg gcccctccct ggggacagcc cctcctggct agtcacaccc tgtaggctcc     840
tctatataac ccaggggcac aggggctgcc ctcattctac caccacctcc acagcacaga     900
cagacactca ggagcagcca gcggcgcgcc caggtaagtt tagtcttttt gtctttatt      960 tcaggtcccg gatccggtgg tggtgcaaat caaagaactg ctcctcagtg gatgttgcct    1020
ttacttctag gcctgtacgg aagtgttact tctgctctaa aagctgcgga attgtacccg    1080
gtaccaccat ggtgagggag cagtacacca cagcaaccga gggaatctgc atcgagaggc    1140
cagagaacca gtacgtgtat aagatcggca tctacggctg gcggaagaga tgtctgtatc    1200
tgttcgtgct gctgctgctg atcatcctgg tggtgaatct ggcccctgacc atctggatcc    1260 tgaaagtgat gtggttttcc ccagcaggaa tgggacacct gtgcgtgaca aaggacggac    1320
tgcggctgga gggagagtct gagttcctgt ttccctgta tgccaaggag atccacagca    1380
gagtggatag ctccctgctg ctgcagtcca cccagaacgt gacagtgaac gcaaggaata    1440
gcgagggaga ggtgaccggc agactgaagg tcggccccaa gatggtggag gtgcagaatc    1500
agcagttcca gatcaactcc aatgacggca gcctctgtt tacagtggat gagaaggagg    1560
tggtggtggg caccgacaag ctgagggtga caggacctga gggcgccctg ttcgagcact    1620
ctgtggagac cccactggtg cgcgcagacc cttttcagga tctgaggctg gagagcccaa    1680
cacgcagcct gtccatggac gcacccgag gcgtgcacat ccaggcacac gcaggcaaga    1740
tcgaggccct gagccagatg gatatcctgt tccactctag cgacggcatg ctggtgctgg    1800
atgccgagac cgtgtgcctg cctaagctgg tgcagggcac atggggccca tctggctcct    1860
ctcagagcct gtacgagatc tgcgtgtgcc cagatgcaa gctgtatctg tccgtggccg    1920
gcgtgtctac cacatgccag gagcacaacc acatctgtct gtgactcgag ggccgcaata    1980
aaagatcttt attttcatta gatctgtgtg ttggtttttt gtgtgtcctg caggggcgcg    2040
cctaatctag agcatggcta cgtagataag tagcatggcg ggttaatcat taactacaag    2100
```

```
gaaccccctag tgatggagtt ggccactccc tctctgcgcg ctcgctcgct cactgaggcc    2160
gggcgaccaa aggtcgcccg acgcccgggc tttgcccggg cggcctcagt gagcgagcga    2220
gcgcgcagct ggcgtaatag cgaagaggcc cgcaccgatc gcccttccca acagttgcgc    2280
agcctgaatg gcgaatggcg attccgttgc aatggctggc ggtaatattg ttctggatat    2340
taccagcaag gccgatagtt tgagttcttc tactcaggca agtgatgtta ttactaatca    2400
aagaagtatt gcgacaacgg ttaatttgcg tgatggacag actcttttac tcggtggcct    2460
cactgattat aaaaacactt ctcaggattc tggcgtaccg ttcctgtcta aaatcccttt    2520
aatcggcctc ctgtttagct cccgctctga ttctaacgag gaaagcacgt tatacgtgct    2580
cgtcaaagca accatagtac gcgccctgta gcggcgcatt aagcgcggcg ggtgtggtgg    2640
ttacgcgcag cgtgaccgct acacttgcca gcgccctagc gcccgctcct ttcgctttct    2700
tcccttcctt tctcgccacg ttcgccatct tcaaatatgt atccgctcat gagacaataa    2760
ccctgataaa tgcttcaata atattgaaaa aggaagagtc ctgaggcgga aagaaccagc    2820
tgtggaatgt gtgtcagtta gggtgtggaa agtccccagg ctccccagca ggcagaagta    2880
tgcaaagcat gcatctcaat tagtcagcaa ccaggtgtgg aaagtcccca ggctccccag    2940
caggcagaag tatgcaaagc atgcatctca attagtcagc aaccatagtc ccgcccctaa    3000
ctccgcccca tggctgacta atttttttta tttatgcaga ggccgaggcc gcctcggcct    3060
ctgagctatt ccagaagtag tgaggaggct ttttttggagg cctaggcttt tgcaaagatc    3120
gatcaagaga caggatgagg atcgtttcgc atgattgaac aagatggatt gcacgcaggt    3180
tctccggccg cttgggtgga gaggctattc ggctatgact gggcacaaca gacaatcggc    3240
tgctctgatg ccgccgtgtt ccggctgtca gcgcaggggc gcccggttct ttttgtcaag    3300
accgacctgt ccggtgccct gaatgaactg caagacgagg cagcgcggct atcgtggctg    3360
gccacgacgg gcgttccttg cgcagctgtg ctcgacgttg tcactgaagc gggaagggac    3420
tggctgctat tgggcgaagt gccggggcag gatctcctgt catctcacct tgctcctgcc    3480
gagaaagtat ccatcatggc tgatgcaatg cggcggctgc atacgcttga tccggctacc    3540
tgcccattcg accaccaagc gaaacatcgc atcgagcgag cacgtactcg gatggaagcc    3600
ggtcttgtcg atcaggatga tctggacgaa gagcatcagg ggctcgcgcc agccgaactg    3660
ttcgccaggc tcaaggcgag catgcccgac ggcgaggatc tcgtcgtgac ccatggcgat    3720
gcctgcttgc cgaatatcat ggtggaaaat ggccgctttt ctggattcat cgactgtggc    3780
cggctgggtg tggcggaccg ctatcaggac atagcgttgg ctacccgtga tattgctgaa    3840
gagcttggcg gcgaatgggc tgaccgcttc ctcgtgcttt acggtatcgc cgctcccgat    3900
tcgcagcgca tcgccttcta tcgccttctt gacgagttct tctgagcggg actctggggt    3960
tcgaaatgac cgaccaagcg acgcccaacc tgccatcacg agatttcgat tccaccgccg    4020
ccttctatga aaggttgggc ttcggaatcg ttttccggga cgccggctgg atgatcctcc    4080
agcgcgggga tctcatgctg gagttcttcg cccacccctag ggggaggcta actgaaacac    4140
ggaaggagac aataccggaa ggaacccgcg ctatgacggc aataaaaaga cagaataaaa    4200
acgttcgcga actattaaac tggcgaacta cttactctag cttcccggca acaattaata    4260
gactggatgg aggcggataa agttgcagga ccacttctgc gctcggccct tccggctggc    4320
tggtttattg ctgataaatc tggagccggt gagcgtgggt ctcgcggtat cattgcagca    4380
ctggggccag atggtaagcc ctcccgtatc gtagttatct acacgacggg gagtcaggca    4440
actatggatg aacgaaatag acagatcgct gagataggtg cctcactgat taagcattgg    4500
```

```
taactgtcag accaagttta ctcatatata ctttagattg atttaaaact tcatttttaa    4560
tttaaaagga tctaggtgaa gatccttttt gataatctca tgaccaaaat cccttaacgt    4620
gagttttcgt tccactgagc gtcagacccc gtagaaaaga tcaaaggatc ttcttgagat    4680
cctttttttc tgcgcgtaat ctgctgcttg caaacaaaaa aaccaccgct accagcggtg    4740
gtttgtttgc cggatcaaga gctaccaact cttttccga aggtaactgg cttcagcaga    4800
gcgcagatac caaatactgt tcttctagtg tagccgtagt taggccacca cttcaagaac    4860
tctgtagcac cgcctacata cctcgctctg ctaatcctgt taccagtggc tgctgccagt    4920
ggcgataagt cgtgtcttac cgggttggac tcaagacgat agttaccgga taaggcgcag    4980
cggtcgggct gaacggggggg ttcgtgcaca gcccagct tggagcgaac gacctacacc    5040
gaactgagat acctacagcg tgagctatga gaaagcgcca cgcttcccga agggagaaag    5100
gcggacaggt atccggtaag cggcagggtc ggaacaggag agcgcacgag ggagcttcca    5160
gggggaaacg cctggtatct ttatagtcct gtcgggtttc gccacctctg acttgagcgt    5220 cgattttgt gatgctcgtc aggggggcgg agcctatgga aaaacgccag caacgcggcc    5280 ttttacggt tcctggcctt ttgctggcct tttgctcaca tgttctttcc tgcgttatcc    5340
cctgattctg tggataaccg tattaccgcc tttgagtgag ctgataccgc tcgccgcagc    5400
cgaacgaccg agcgcagcga gtcagtgagc gaggaagcgg aagagcgccc aatacgcaaa    5460
ccgcctctcc ccgcgcgttg gccgattcat taatg                              5495
```

<210> SEQ ID NO 9
<211> LENGTH: 291
<212> TYPE: PRT
<213> ORGANISM: Artificial Sequence
<220> FEATURE:
<223> OTHER INFORMATION: Human Gamma-Sarcoglycan amino acid sequence

<400> SEQUENCE: 9

```
Met Val Arg Glu Gln Tyr Thr Thr Ala Thr Glu Gly Ile Cys Ile Glu
1               5                   10                  15

Arg Pro Glu Asn Gln Tyr Val Tyr Lys Ile Gly Ile Tyr Gly Trp Arg
            20                  25                  30

Lys Arg Cys Leu Tyr Leu Phe Val Leu Leu Leu Ile Ile Leu Val
        35                  40                  45

Val Asn Leu Ala Leu Thr Ile Trp Ile Leu Lys Val Met Trp Phe Ser
    50                  55                  60

Pro Ala Gly Met Gly His Leu Cys Val Thr Lys Asp Gly Leu Arg Leu
65                  70                  75                  80

Glu Gly Glu Ser Glu Phe Leu Phe Pro Leu Tyr Ala Lys Glu Ile His
                85                  90                  95

Ser Arg Val Asp Ser Ser Leu Leu Gln Ser Thr Gln Asn Val Thr
            100                 105                 110

Val Asn Ala Arg Asn Ser Glu Gly Glu Val Thr Gly Arg Leu Lys Val
        115                 120                 125

Gly Pro Lys Met Val Glu Val Gln Asn Gln Gln Phe Gln Ile Asn Ser
    130                 135                 140

Asn Asp Gly Lys Pro Leu Phe Thr Val Asp Glu Lys Glu Val Val Val
145                 150                 155                 160

Gly Thr Asp Lys Leu Arg Val Thr Gly Pro Glu Gly Ala Leu Phe Glu
                165                 170                 175

His Ser Val Glu Thr Pro Leu Val Arg Ala Asp Pro Phe Gln Asp Leu
```

```
            180             185             190
Arg Leu Glu Ser Pro Thr Arg Ser Leu Ser Met Asp Ala Pro Arg Gly
            195             200             205

Val His Ile Gln Ala His Ala Gly Lys Ile Glu Ala Leu Ser Gln Met
        210             215             220

Asp Ile Leu Phe His Ser Ser Asp Gly Met Leu Val Leu Asp Ala Glu
225             230             235             240

Thr Val Cys Leu Pro Lys Leu Val Gln Gly Thr Trp Gly Pro Ser Gly
            245             250             255

Ser Ser Gln Ser Leu Tyr Glu Ile Cys Val Cys Pro Asp Gly Lys Leu
        260             265             270

Tyr Leu Ser Val Ala Gly Val Ser Thr Thr Cys Gln Glu His Asn His
        275             280             285

Ile Cys Leu
        290

<210> SEQ ID NO 10
<211> LENGTH: 4355
<212> TYPE: DNA
<213> ORGANISM: Artificial Sequence
<220> FEATURE:
<223> OTHER INFORMATION: Self-complementary (SC) expression cassette
      polynucleotide sequence of scAAVrh74.MHCK7.hSGCG

<400> SEQUENCE: 10
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
agattaggcg cgcccctgca ggacacacaa aaaccaaca cacagatcta atgaaaataa      240
agatctttta ttgcggccct cgagtcacag acagatgtgg ttgtgctcct ggcatgtggt     300
agacacgccg ccacggaca gatacagctt gccatctggg cacacgcaga tctcgtacag     360
gctctgagag gagccagatg ggccccatgt gccctgcacc agcttaggca ggcacacggt     420
ctcggcatcc agcaccagca tgccgtcgct agagtggaac aggatatcca tctggctcag     480
ggcctcgatc ttgcctgcgt gtgcctggat gtgcacgcct ctgggtgcgt ccatggacag     540
gctgcgtgtt gggctctcca gcctcagatc ctgaaaaggg tctgcgcgca ccagtggggt     600
ctccacagag tgctcgaaca gggcgccctc aggtcctgtc accctcagct tgtcggtgcc     660
caccaccacc tccttctcat ccactgtaaa cagaggcttg ccgtcattgg agttgatctg     720
gaactgctga ttctgcacct ccaccatctt ggggccgacc ttcagtctgc cggtcacctc     780
tccctcgcta ttccttgcgt tcactgtcac gttctgggtg gactgcagca gcagggagct     840
atccactctg ctgtggatct ccttggcata caggggaaac aggaactcag actctccctc     900
cagccgcagt ccgtcctttg tcacgcacag gtgtcccatt cctgctgggg aaaaccacat     960
cactttcagg atccagatgg tcaggccag attaccacc aggatgatca gcagcagcag     1020
cacgaacaga tacagacatc tcttccgcca gccgtagatg ccgatcttat acacgtactg     1080
gttctctggc ctctcgatgc agattccctc ggttgctgtg gtgtactgct ccctcaccat     1140
ggtggtaccg ggtacaattc cgcagctttt agagcagaag taacacttcc gtacaggcct     1200
agaagtaaag gcaacatcca ctgaggagca gttctttgat ttgcaccacc accggatccg     1260
ggacctgaaa taaagacaa aaagactaaa cttacctggg cgcgccgctg ctgctcctg      1320
agtgtctgtc tgtgctgtgg aggtggtggt agaatgaggg cagcccctgt gcccctgggt     1380
```

| | | | | |
|---|---|---|---|---|
| tatatagagg | agcctacagg | gtgtgactag | ccaggagggg | ctgtcccag ggaggggccc | 1440 |
| ctgagagcag | atgagctttc | agctcgttgc | ccgggcaccg | tgcccacccc ggacccaggc | 1500 |
| gtgcagcttg | cccagcccca | tggccttgta | tgggctgccc | caagggctga cttgctcact | 1560 |
| ggttcctaaa | ctaagtgctg | agtctagctg | gcggggggaca | gctggccctt cgccgggaac | 1620 |
| atggaacagt | aatactttgg | gagtcccagg | cacgtataag | ccctggcccc caagcctgtt | 1680 |
| acagcctgcc | ctcagtcccc | cacagccttg | ttcgaagatc | ttcgcatgca ggggatccac | 1740 |
| cagggacagg | gttatttttta | gaggcagcag | gtgttggggg | ggggggggca gccacatgtc | 1800 |
| tgggttaatt | ataaccaggc | atctcgggtg | tccccaggcc | ttgcctcctt acatgggcag | 1860 |
| cctagacccg | tagtggggca | tgctagacag | cagggcccca | aggtttgccc atgaaaggtc | 1920 |
| tgttgccctc | gccctctgg  | ctccatggcc | ttttttttagt | ccttgggcac attcctcctc | 1980 |
| cccaaagggc | cgatgggcag | atagaggaga | gacaggagcg | tctcacacca cctcccctac | 2040 |
| ccaggccctt | acctcagtta | tttttaatct | gaagggtcta | gcttagacat gcaagcttgc | 2100 |
| ggccgccaat | tggttaaccc | cactccctct | ctgcgcgctc | gctcgctcac tgaggccgcc | 2160 |
| cgggcaaagc | ccgggcgtcg | ggcgaccttt | ggtcgcccgg | cctcagtgag cgagcgagcg | 2220 |
| cgcagagagg | gagtggggtt | aaccaattgg | cggccgcaag | cttgcatgtc taagctagac | 2280 |
| ccttcagatt | aaaaataact | gaggtaaggg | cctgggtagg | ggaggtggtg tgagacgctc | 2340 |
| ctgtctctcc | tctatctgcc | catcggccct | ttggggagga | ggaatgtgcc caaggactaa | 2400 |
| aaaaaggcca | tggagccaga | ggggcgaggg | caacagacct | ttcatgggca aaccttgggg | 2460 |
| ccctgctgtc | tagcatgccc | cactacgggt | ctaggctgcc | catgtaagga ggcaaggcct | 2520 |
| ggggacaccc | gagatgcctg | gttataatta | acccagacat | gtggctgccc cccccccccc | 2580 |
| aacacctgct | gcctctaaaa | ataaccctgt | ccctggtgga | tcccctgcat gcgaagatct | 2640 |
| tcgaacaagg | ctgtggggga | ctgagggcag | gctgtaacag | gcttggggc cagggcttat | 2700 |
| acgtgcctgg | gactcccaaa | gtattactgt | tccatgttcc | cggcgaaggg ccagctgtcc | 2760 |
| cccgccagct | agactcagca | cttagtttag | gaaccagtga | gcaagtcagc ccttggggca | 2820 |
| gcccatacaa | ggccatgggg | ctgggcaagc | tgcacgcctg | ggtccggggt gggcacggtg | 2880 |
| cccgggcaac | gagctgaaag | ctcatctgct | ctcaggggcc | cctccctggg gacagcccct | 2940 |
| cctggctagt | cacaccctgt | aggctcctct | atataaccca | ggggcacagg ggctgccctc | 3000 |
| attctaccac | cacctccaca | gcacagacag | acactcagga | gcagccagcg gcgcgcccag | 3060 |
| gtaagtttag | tcttttttgtc | ttttatttca | ggtcccggat | ccggtggtgg tgcaaatcaa | 3120 |
| agaactgctc | ctcagtggat | gttgcccttta | cttctaggcc | tgtacggaag tgttacttct | 3180 |
| gctctaaaag | ctgcggaatt | gtaccccggta | ccaccatggt | gagggagcag tacaccacag | 3240 |
| caaccgaggg | aatctgcatc | gagaggccag | agaaccagta | cgtgtataag atcggcatct | 3300 |
| acggctggcg | gaagagatgt | ctgtatctgt | tcgtgctgct | gctgctgatc atcctggtgg | 3360 |
| tgaatctggc | cctgaccatc | tggatcctga | aagtgatgtg | gtttccccca gcaggaatgg | 3420 |
| gacacctgtg | cgtgacaaag | gacggactgc | ggctggaggg | agagtctgag ttcctgtttc | 3480 |
| ccctgtatgc | caaggagatc | cacagcagag | tggatagctc | cctgctgctg cagtccaccc | 3540 |
| agaacgtgac | agtgaacgca | aggaatagcg | agggagaggt | gaccggcaga ctgaaggtcg | 3600 |
| gccccaagat | ggtggaggtg | cagaatcagc | agttccagat | caactccaat gacgcaagc | 3660 |
| ctctgtttac | agtggatgag | aaggaggtgg | tggtgggcac | cgacaagctg agggtgacag | 3720 |

```
gacctgaggg cgccctgttc gagcactctg tggagacccc actggtgcgc gcagacccttt    3780 ttcaggatct gaggctggag agcccaacac gcagcctgtc catggacgca cccagaggcg    3840
tgcacatcca ggcacacgca ggcaagatcg aggccctgag ccagatggat atcctgttcc    3900
actctagcga cggcatgctg gtgctggatg ccgagaccgt gtgcctgcct aagctggtgc    3960
agggcacatg gggcccatct ggctcctctc agagcctgta cgagatctgc gtgtgcccag    4020
atggcaagct gtatctgtcc gtggccggcg tgtctaccac atgccaggag cacaaccaca    4080
tctgtctgtg actcgagggc cgcaataaaa gatctttatt ttcattagat ctgtgtgttg    4140
gttttttgtg tgtcctgcag gggcgcgcct aatctagagc atggctacgt agataagtag    4200
catggcgggt taatcattaa ctacaaggaa ccctagtga tggagttggc cactccctct    4260
ctgcgcgctc gctcgctcac tgaggccggg cgaccaaagg tcgcccgacg cccgggcttt    4320
gcccgggcgg cctcagtgag cgagcgagcg cgcag                              4355
```

<210> SEQ ID NO 11
<211> LENGTH: 25
<212> TYPE: DNA
<213> ORGANISM: Artificial Sequence
<220> FEATURE:
<223> OTHER INFORMATION: SGCG Primer 1

<400> SEQUENCE: 11
ggaggaagcg ctgcctatac ctatt                                          25

<210> SEQ ID NO 12
<211> LENGTH: 25
<212> TYPE: DNA
<213> ORGANISM: Artificial Sequence
<220> FEATURE:
<223> OTHER INFORMATION: SGCG Primer 2

<400> SEQUENCE: 12
ggaggaagcg ctgcctatac ctatt                                          25

<210> SEQ ID NO 13
<211> LENGTH: 21
<212> TYPE: DNA
<213> ORGANISM: Artificial Sequence
<220> FEATURE:
<223> OTHER INFORMATION: MHCK7 forward primer

<400> SEQUENCE: 13
ccaacacctg ctgcctctaa a                                              21

<210> SEQ ID NO 14
<211> LENGTH: 19
<212> TYPE: DNA
<213> ORGANISM: Artificial Sequence
<220> FEATURE:
<223> OTHER INFORMATION: MHCK7 reverse primer

<400> SEQUENCE: 14
gtcccccaca gccttgttc                                                 19

<210> SEQ ID NO 15
<211> LENGTH: 23
<212> TYPE: DNA

```
<213> ORGANISM: Artificial Sequence
<220> FEATURE:
<223> OTHER INFORMATION: MHCK7 intron probe sequence

<400> SEQUENCE: 15
tggatcccct gcatgcgaag atc                                              23
```

US 11,925,675 B2

SYSTEMIC DELIVERY OF ADENO-ASSOCIATED VIRUS VECTOR EXPRESSING GAMMA-SARCOGLYCAN AND THE TREATMENT OF MUSCULAR DYSTROPHY

CROSS REFERENCE TO RELATED APPLICATIONS

This application claims benefit under 35 U.S.C. § 119(e) of U.S. Provisional Application No. 63/075,697, filed Sep. 8, 2020, the content of which is incorporated herein by reference in its entirety.

SEQUENCE LISTING

The content of the electronically submitted Sequence Listing in ASCII text file (Name: 4140_0540001_Seqlisting_ST25.txt; Size: 23,895 bytes; and Date of Creation: Sep. 7, 2021), filed with the application, is incorporated herein by reference in its entirety.

FIELD OF THE INVENTION

Described herein are therapy vectors such as AAV vectors expressing γ-sarcoglycan and method of using these vectors to reduce and prevent fibrosis in subjects suffering from a muscular dystrophy.

BACKGROUND

Limb-girdle muscular dystrophy (LGMD) type 2C (LGMD2C) is an autosomal recessive disorder resulting from mutations in the gene encoding γ-sarcoglycan (SGCG), causing loss of functional protein. It presents as progressive muscular dystrophies starting in the girdle muscles before extending to lower and upper extremity muscles, and can also present in the diaphragm (DIA) and heart (HRT), resulting in respiratory and cardiac failure in specific patients. There is no approved disease-modifying therapies for LGMD2C. Therefore, there is a need for an effective therapy for LGMD2C patients.

SUMMARY

Described herein are gene therapy vectors, e.g. AAV, expressing the γ-sarcoglycan gene and methods of delivering γ-sarcoglycan to the muscle to reduce and/or prevent fibrosis; and/or to increase muscular force, and/or to treat a mammalian subject suffering from muscular dystrophy.

In one aspect, described herein is a method of treating muscular dystrophy in a subject in need thereof comprising the step of administering a recombinant adeno-associated virus (rAAV) scAAVrh74.MHCK7.hSGCG to a subject in need thereof, wherein the rAAV is administered using a systemic route of administration and at a dose of about $2 \times 10^{12}$ vg/kg to about $5.0 \times 10^{14}$ vg/kg based on a supercoiled plasmid as the quantitation standard or $3.0 \times 10^{12}$ vg/kg to about $1.0 \times 10^{14}$ vg/kg based on a linearized plasmid as the quantitation standard; wherein the serum creatine kinase (CK) level in the subject is decreased after administration of the rAAV as compared to serum CK level before administration of the rAAV.

In another aspect, provided is a method of treating muscular dystrophy in a subject in need thereof comprising the step of administering a recombinant adeno-associated virus (rAAV) scAAVrh74.MHCK7.hSGCG, wherein the level of gamma-sarcoglycan gene expression in a cell of the subject is increased after administration of the rAAV as compared to the level of gamma-sarcoglycan gene expression before administration of the rAAV; wherein the number of gamma-sarcoglycan positive fibers in the muscle tissue of the subject is increased after administration of the rAAV as compared to the number of gamma-sarcoglycan positive fibers before administration of the rAAV; or wherein motor function is improved in said subject as compared to the motor function of said subject before administration of the rAAV, and wherein the motor function is determined by a 100 meter timed walk test and/or NSAD. In the embodiment, the NSAD are increased in in said subject as compared to the NSAD of said subject before administration of the rAAV.

In another aspect, this disclosure provides a method of treating a limb-girdle muscular dystrophy in a subject in need, comprising administering to the subject an rAAV intravenous infusion at a dose of about $4.63 \times 10^{12}$ vg/kg, about $1.85 \times 10^{13}$ vg/kg or $7.41 \times 10^{13}$ vg/kg based on a linearized plasmid as the quantitation standard, and wherein the rAAV comprises a nucleotide sequence of SEQ ID NO: 1, SEQ ID NO: 7, or SEQ ID NO: 10. In one embodiment, the rAAV comprises a nucleotide sequence of SEQ ID NO: 10. In another aspect, the disclosure describes a method of expressing gamma-sarcoglycan gene in a subject's cell comprising administering to the subject the scAAVrh74.MHCK7.hSGCG construct that comprises a nucleotide sequence that is at least 90%, 95%, or 99% identical to SEQ ID NO: 7 or 10. In one aspect, the disclosure provides a method of increasing gamma-sarcoglycan positive fibers and/or decreasing CK level in a subject's muscle tissue comprising administering to the subject the scAAVrh74.MHCK7.hSGCG construct nucleotide sequence that is at least 90%, 95%, or 99% identical to SEQ ID NO: 7.

In one aspect, described herein is a method of increasing the expression of alpha-sarcoglycan and/or beta-sarcoglycan in a subject in need thereof comprising administering to the subject an rAAV comprising a scAAVrh74.MHCK7.hSGCG construct with a nucleotide sequence that is at least 90%, 95%, or 99% identical to SEQ ID NO: 1 or SEQ ID NO: 7, or SEQ ID NO: 10. In another aspect, provided herein is a method of increasing localization of alpha-sarcoglycan and/or beta-sarcoglycan to a cell membrane in a subject in need thereof comprising administering to the subject the scAAVrh74.MHCK7.hSGCG construct nucleotide sequence that is at least 90%, 95%, or 99% identical to SEQ ID NO: 1 or SEQ ID NO: 7 or SEQ ID NO: 10. In another aspect, provided is a method of increasing sarcoglycan expression in muscle tissue or improving muscle function of a subject comprising administering to the subject an rAAV comprising a nucleotide sequence that is at least 90%, 95%, or 99% identical to SEQ ID NO: 7 or SEQ ID NO: 10. In another aspect, the disclosure provides a method of increasing sarcoglycan expression in muscle tissue of a subject comprising administering to the subject a construct comprising a nucleotide sequence encoding a first sarcoglycan, and detecting increased expression of at least a second sarcoglycan in the cell membrane of the cell expressing said first sarcoglycan.

In another aspect, described is a composition, comprising an rAAV scAAVrh74.MHCK7.hSGCG vector, a buffer agent, an ionic strength agent, and a surfactant. In another aspect, described herein is a pharmaceutical composition comprising a recombinant AAV (rAAV) scAAVrh74.MHCK7.hSGCG, wherein the scAAVrh74.MHCK7.hSGCG comprising a nucleotide sequence that is at least 90%, 95% or 99% identical to SEQ ID NO: 7 or SEQ ID NO: 10. In another embodiment, the scAAVrh74.MHCK7.hSGCG comprising a nucleotide sequence that is at least 90%, 95% or 99% identical to SEQ ID NO: 10. In another embodiment, the scAAVrh74.MHCK7.hSGCG comprising a nucleotide sequence of SEQ ID NO: 10.

In another aspect, provided is a method of generating a recombinant AAV scAAVrh74.MHCK7.hSGCG, comprising transferring a plasmid to a cell, wherein the plasmid comprises a nucleotide sequence that is at least 90%, 95%, or 99% identical to SEQ ID NO: 8. In particular, the plasmid comprises a nucleotide sequence of SEQ ID NO: 8. In another embodiment, the plasmid comprises a nucleotide sequence of SEQ ID NO: 7 or SEQ ID NO: 10.

In another aspect, described here in a recombinant AAV vector comprising a polynucleotide sequence encoding γ-sarcoglycan. In some embodiments, the polynucleotide sequence encoding γ-sarcoglycan comprises a sequence e.g. at least 65%, at least 70%, at least 75%, at least 80%, 81%, 82%, 83%, 84%, 85%, 86%, 87%, 88%, or 89%, more typically 90%, 91%, 92%, 93%, 94%, 95%, 96%, 97%, 98%, 99% or more identical to the nucleotide sequence set forth in SEQ ID NO: 1 and encodes protein that retains γ-sarcoglycan activity. In some embodiments, the polynucleotide sequence encoding γ-sarcoglycan comprises the nucleotide sequence set forth in SEQ ID NO: 1. In some embodiments, the polynucleotide sequence encoding γ-sarcoglycan consists of the nucleotide sequence set forth in SEQ ID NO: 1.

In another aspect, a recombinant AAV vector described herein comprises a polynucleotide sequence encoding γ-sarcoglycan that is at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the amino acid sequence of SEQ ID NO: 9, and the protein retains γ-sarcoglycan activity.

In another aspect, described herein is a recombinant AAV vector comprising a polynucleotide sequence encoding functional γ-sarcoglycan. In one embodiment, the polynucleotide sequence comprises a nucleotide sequence that hybridizes under stringent conditions to the nucleic acid sequence of SEQ ID NO: 1 or SEQ ID NO: 10, or a complement thereof.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

When ranges are used herein for physical properties, such as molecular weight, concentration, or dosage, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

In another aspect, the recombinant AAV vectors described herein may be operably linked to a muscle-specific control element. For example the muscle-specific control element is human skeletal actin gene element, cardiac actin gene element, myocyte-specific enhancer binding factor MEF, muscle creatine kinase (MCK), tMCK (truncated MCK), myosin heavy chain (MHC), MHCK7 (a hybrid version of MHC and MCK), C5-12 (synthetic promoter), murine creatine kinase enhancer element, skeletal fast-twitch troponin C gene element, slow-twitch cardiac troponin C gene element, the slow-twitch troponin I gene element, hypozia-inducible nuclear factors, steroid-inducible element or glucocorticoid response element (GRE).

In some embodiments, the rAAV pAAV.MHCK7.hSGCG comprises a nucleotide sequence that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to the nucleotide sequence set forth in SEQ ID NO: 1 or SEQ ID NO: 7 or SEQ ID NO: 10, or a nucleotide sequence that encodes a polypeptide that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to SEQ ID NO: 9.

In one embodiment, the polynucleotide sequence encodes a protein that retains sarcoglycan activity, including beta- and/or alpha-sarcoglycan activity. In another embodiment, the polynucleotide sequence encodes a protein that retains gamma-sarcoglycan activity.

In some embodiments, the muscle-specific promoter is tMHCK7 (SEQ ID NO: 2). An exemplary rAAV described herein is pAAV.tMCK.hSGCG which comprises the nucleotide sequence of SEQ ID NO: 7 or SEQ ID NO: 10.

The AAV can be any serotype, for example AAV-1, AAV-2, AAV-3, AAV-4, AAV-5, AAV-6, AAV-7, AAV-8, AAV-9, AAV-10, AAV-11, AAV-12, AAV-13 and AAVrh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

Compositions comprising any of the rAAV vectors described herein are also contemplated.

In some embodiments, the disclosure provides a composition or pharmaceutical composition that comprises an scAAVrh74.MHCK7.hSGCG rAAV vector comprising a nucleotide sequence that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to the nucleotide sequence set forth in SEQ ID NO: 1 or SEQ ID NO: 7 or SEQ ID NO: 10, or comprising a nucleotide sequence that encodes a polypeptide that is at least 65%, at least 70%, at least 75%, at least 80%, about 81%, about 82%, about 83%, about 84%, about 85%, about 86%, about 87%, about 88%, or about 89%, more typically about 90%, about 91%, about 92%, about 93%, about 94%, about 95%, about 96%, about 97%, about 98%, or about 99% identical to SEQ ID NO: 9. In addition, the disclosure provides a provides a composition or pharmaceutical composition that comprises an scAAVrh74.MHCK7.hSGCG rAAV vector comprising a nucleotide sequence of SEQ ID NO: 1 or SEQ ID NO: 7 or SEQ ID NO: 10, or comprising a nucleotide sequence that encodes a polypeptide comprising the amino acid sequence of SEQ ID NO: 9.

Provided are methods of treating muscular dystrophy in a subject in need thereof comprising the step of administering a recombinant adeno-associated virus (rAAV) scAAVrh74.MHCK7.hSGCG, wherein the rAAV is administered using a systemic route of administration and at a dose of $2 \times 10^{12}$ vg/kg to about $5.0 \times 10^{14}$ vg/kg based on a linearized plasmid as the quantitation standard.

Also provided are compositions for treating muscular dystrophy, wherein the composition comprises a recombinant adeno-associated virus (rAAV) scAAVrh74.MHCK7.hSGC at a dose of about $2.0 \times 10^{12}$ vg/kg to about $5.0 \times 10^{14}$ vg/kg based on a linearized plasmid as the quantitation standard and the composition is formulated for systemic administration.

In addition, provided are uses of a recombinant adeno-associated virus (rAAV) scAAVrh74.MHCK7.hSGC for the preparation of a medicament for treating muscular dystrophy, wherein the medicament comprises scAAVrh74.MHCK7.hSGC at a dose of about $1.0 \times 10^{12}$ vg/kg to about $5.0 \times 10^{14}$ vg/kg based on a linearized plasmid as the quantitation standard and the medicament is formulated for systemic administration.

In any of the provided methods, compositions and uses, the level of gamma-sarcoglycan gene expression in a cell of the subject is increased after administration of the rAAV as compared to the level of gamma-sarcoglycan gene expression before administration of the rAAV; wherein the serum creatine kinase (CK) level in the subject is decreased after administration of the rAAV as compared to serum CK level before administration of the rAAV; and/or wherein the number of gamma-sarcoglycan positive fibers in the muscle tissue of the subject is increased after administration of the rAAV as compared to the number of gamma-sarcoglycan positive fibers before administration of the rAAV.

In another embodiment, in any of the provided methods, compositions and uses, motor function is improved in said subject as compared to the motor function of said subject before administration of the rAAV, and wherein the motor function is determined by a 100 meter timed walk test. For example, motor function is improved by at least 5% in 1 month or thirty days post-gene transfer, at least 10% in 2 months or sixty days post-gene transfer, or at least 15% in 3 months or ninety days post gene transfer. In some embodiments, the motor function is improved by at least 5%, 10%, 15%, 20%, 25%, 30%, 40%, 45%, or 50%.

For example, in any of the provided methods, compositions and uses, the systemic route of administration is an intravenous route. For example, the rAAV is administered using an intravenous route and the dose of the rAAV administered is about $4.63 \times 10^{12}$ vg/kg, about $1.85 \times 10^{13}$ vg/kg or $7.41 \times 10^{13}$ vg/kg based on a linearized plasmid as the quantitation standard.

In some embodiments, the dose of rAAV administered using an intravenous route and the dose is about $2.0 \times 10^{13}$ vg/kg to about $5 \times 10^{14}$ based on a linearized plasmid as the quantitation standard.

In addition, the dose of the rAAV administered is about $1.5 \times 10^{13}$ vg to about $2 \times 10^{16}$ vg, or $1.5 \times 10^{13}$ vg to $1 \times 10^{16}$ vg, or about $1.5 \times 10^{13}$ vg to about $2 \times 10^{15}$ vg, or about $1.5 \times 10^{13}$ vg to about $1 \times 10^{15}$ vg. In addition, in any of the methods, compositions and uses, the dose of rAAV is administered at a concentration of about 10 mL/kg. In any of the methods, compositions or uses provided, the muscular dystrophy is limb-girdle muscular dystrophy.

In addition, provided are methods of treating muscular dystrophy in a subject in need thereof comprising the step of administering a recombinant adeno-associated virus (rAAV) scAAVrh74.MHCK7.hSGCG, wherein the rAAV is administered using a systemic route of administration and at a dose of about $2.0 \times 10^{12}$ vg/kg to about $5.0 \times 10^{14}$ vg/kg based on a linearized plasmid as the quantitation standard; wherein the level of gamma-sarcoglycan gene expression in a cell of the subject is increased after administration of the rAAV as compared to the level of gamma-sarcoglycan gene expression before administration of the rAAV; wherein the serum CK level in the subject is decreased after administration of the rAAV as compared to serum CK level before administration of the rAAV; or wherein the number of gamma-sarcoglycan positive fibers in the muscle tissue of the subject is increased after administration of the rAAV as compared to the number of gamma-sarcoglycan positive fibers before administration of the rAAV. For example, in any of the provided methods, the systemic route of administration is an intravenous route and the dose of the rAAV administered is about $4.63 \times 10^{12}$ vg/kg vg/kg based on a linearized plasmid as the quantitation standard. In another embodiment, the dose of the rAAV administered is about $1.85 \times 10^{13}$ vg/kg based on a linearized plasmid as the quantitation standard. In another embodiment, the dose of the rAAV administered is about $7.41 \times 10^{13}$ vg/kg based on a linearized plasmid as the quantitation standard. In addition, the total dose of the rAAV administered is about $1.5 \times 10^{13}$ vg to about $2 \times 10^{16}$ vg, or $1.5 \times 10^{13}$ vg to $1 \times 10^{16}$ vg, or about $1.5 \times 10^{13}$ vg to about $2 \times 10^{15}$ vg, or about $1.5 \times 10^{13}$ vg to about $1 \times 10^{15}$ vg. In addition, in any of the methods, the dose of rAAV is administered at a concentration of about 10 mL/kg. In any of the methods provided, the muscular dystrophy is limb-girdle muscular dystrophy.

In some embodiments, the disclosure includes a method of treating muscular dystrophy in a subject in need thereof comprising the step of administering a recombinant adeno-associated virus (rAAV) scAAVrh74.MHCK7.hSGCG, wherein motor function is demonstrably improved in said subject as compared to motor function of said subject before administration of the rAAV, and wherein motor function is determined by a 100 m timed walk test and/or NSAD. In some aspects, motor function is improved by at least 5% in 1 month or thirty days post-gene transfer, at least 10% in 2 months or sixty days post-gene transfer, or at least 15% in 3 months or ninety days post gene transfer. In some aspects, motor function is improved by at least about 5%, about 10%, about 15%, about 20%, about 25%, about 30%, about 40%, about 45%, or about 50%.

Provided are methods of increasing the level of alpha-sarcoglycan and/or beta-sarcoglycan in a subject in need thereof comprising administering to the subject the scAAVrh74.MHCK7.hSGCG construct that comprises a nucleotide sequence of SEQ ID NO: 1 or SEQ ID NO: 7 or SEQ ID NO: 10. In addition, provided are composition for increasing the level of alpha-sarcoglycan and/or beta-sarcoglycan in a subject in need, wherein the composition comprises scAAVrh74.MHCK7.hSGCG construct comprising a nucleotide sequence of SEQ ID NO: 1 or SEQ ID NO: 7. Also provided are uses of scAAVrh74.MHCK7.hSGCG construct that comprises a nucleotide sequence of SEQ ID NO: 1 or SEQ ID NO: 7 or SEQ ID NO: 10 for the preparation of a medicament for increasing the level of alpha-sarcoglycan and/or beta-sarcoglycan in a subject in need thereof. In some aspects, the alpha-sarcoglycan and/or beta-sarcoglycan is colocalized to the membrane of a cell expressing a gamma-sarcoglycan encoded by scAAVrh74.MHCK7.hSGCG. In some aspects, the beta-sarcoglycan is colocalized to the membrane of a cell expressing a gamma-sarcoglycan encoded by scAAVrh74.MHCK7.hSGCG.

In some embodiments, the scAAVrh74.MHCK7.hSGCG construct comprises an intron sequence. In one embodiment, the intron sequence comprise a nucleotide sequence of SEQ ID NO: 6. In another embodiment, the scAAVrh74.MHCK7.hSGCG construct comprises a polyA sequence. In one embodiment, the polyA sequence comprises a nucleotide sequence of SEQ ID NO: 5. In another embodiment, the scAAVrh74.MHCK7.hSGCG construct comprises a 5' inverted terminal repeat (ITR) sequence. In one embodiment, the 5'ITR sequence comprises a nucleotide sequence of SEQ ID NO: 3. In another embodiment, the scAAVrh74.MHCK7.hSGCG construct comprises a 3' inverted terminal repeat (ITR) sequence. In one embodiment, the 3'ITR sequence comprises a nucleotide sequence of SEQ ID NO: 4.

Also provided are methods of increasing sarcoglycan expression in muscle tissue of a subject comprising administering to the subject a construct comprising a nucleotide sequence encoding a first sarcoglycan, and detecting increased expression of at least a second sarcoglycan in the cell membrane of the cell expressing said first sarcoglycan. In some aspects, the first sarcoglycan is γ-sarcoglycan (SGCG), and said second sarcoglycan is α-sarcoglycan (SGCA), γ-sarcoglycan (SGCG), or δ-sarcoglycan (SGCD).

In any of the methods, uses and compositions of treating muscular dystrophy provided, the subject is 4-15 years of age, has confirmed gamma-sarcoglycan (SGCG) mutation in both alleles, was negative for AAVrh74 antibodies and/or had >40% or normal 100 meter walk test. In any of the methods, uses and compositions of treating muscular dystrophy provided, the subject is a pediatric subject. In some embodiments, the subject is a pediatric subject, such as a subject ranging in age from 1 to 10 years. In some embodiments, the subject is 4 to 15 years of age. The subject, in on embodiment, is an adolescent subject, such as a subject ranging in age from 10 to 19 years. In addition, the subject, in one embodiment, is a young adult subject such as a subject ranging in age from late teens or early twenties, such as the subject may range in age from 15 to 29 years of age. In some embodiments, the subject is a middle-aged adult or an elderly subject, such that the middle-aged adult may range in age from 25-55 years of age and the elderly subject may range in age over 50 years of age.

In some embodiments, the rAAV is administered by injection, infusion or implantation. For example, the rAAV is administered by infusion over approximately 1 to 2 hours. In addition, the rAAV is administered by an intravenous route through a peripheral limb vein.

In the methods of treating muscular dystrophy in a subject in need thereof comprising the step of administering a recombinant adeno-associated virus (rAAV) scAAVrh74.MHCK7.hSGCG, wherein the rAAV is administered using a systemic route of administration and at a dose of about $1.0 \times 10^{12}$ vg/kg to about $5.0 \times 10^{14}$ vg/kg based on a linearized plasmid as the quantitation standard and the rAAV comprises the human γ-sarcoglycan nucleotide sequence of SEQ ID NO: 1. In addition, the rAAV comprises the MHCK7 promoter sequence of SEQ ID NO: 2. In some embodiments, the rAAV is of the serotype AAVrh.74. In addition, the rAAV comprises the scAAVrh74.MHCK7.hSGCG construct nucleotide sequence of SEQ ID NO: 1 or SEQ ID NO: 7 or SEQ ID NO: 10.

In an exemplary embodiment, methods of treating muscular dystrophy in a subject in need thereof comprise the step of administering a recombinant adeno-associated virus (rAAV) scAAVrh74.MHCK7.hSGCG, wherein the rAAV is administered using a systemic route of administration and at a dose of about $1.0 \times 10^{12}$ vg/kg to about $5.0 \times 10^{14}$ vg/kg based on a linearized plasmid as the quantitation standard, wherein the subject is suffering from limb-girdle muscular dystrophy, and the rAAV is administered by intravenous infusion over approximately 1 to 2 hours at a dose of about $1.25 \times 10^{13}$ vg/kg, about $5.0 \times 10^{13}$ vg/kg or about $2.0 \times 10^{14}$ vg/kg based on a supercoiled plasmid as the quantitation standard, or about $1.85 \times 10^{13}$ vg/kg, $7.41 \times 10^{13}$ vg/kg or about $4.63 \times 10^{12}$ vg/kg based on a linearized plasmid as the quantitation standard, and wherein the rAAV comprises the scAAVrh74.MHCK7.hSGCG construct nucleotide sequence of SEQ ID NO: 1 or SEQ ID NO: 7 or SEQ ID NO: 10.

The disclosure also provides for use of a dose of recombinant adeno-associated virus (rAAV) scAAVrh74.MHCK7.hSGCG for the preparation of a medicament for the treatment of limb-girdle muscular dystrophy, wherein the dose of rAAV at about $1.25 \times 10^{13}$ vg/kg, about $5.0 \times 10^{13}$ vg/kg or about $2.0 \times 10^{14}$ vg/kg based on a supercoiled plasmid as the quantitation standard, or about $1.85 \times 10^{13}$ vg/kg, about $4.63 \times 10^{12}$ vg/kg, or about $7.41 \times 10^{13}$ vg/kg based on a linearized plasmid as the quantitation standard and the medicament is formulated to deliver the dose by intravenous infusion over approximately 1 to 2 hours.

The disclosure further provides a method of improving muscle function of a subject comprising administering to the subject a construct comprising a nucleotide sequence with at least 90% identity, at least 95% identity, at least 99% identity, or 100% identity to SEQ ID NO: 1 or 7. In addition, provided are compositions for improving muscle function of a subject, wherein the composition comprises a construct comprising a nucleotide sequence with at least 90% identity, at least 95% identity, at least 99% identity or 100% identity to SEQ ID NO: 1 or 7 or 10. Also provided are uses of a construct comprising a nucleotide sequence with at least 90% identity, at least 95% identity, at least 99% identity or 100% identity to SEQ ID NO: 1 or 7 or 10 for the preparation of a medicament for improving muscle function of a subject.

In any of the provided methods, uses or compositions, the subject suffers from a genetic mutation in a gene encoding a sarcoglycan or a muscular dystrophy. In some aspects, the sarcoglycan is γ-sarcoglycan (SGCG), α-sarcoglycan (SGCA), γ-sarcoglycan (SGCG), or δ-sarcoglycan (SGCD). In some aspects, the sarcoglycan is γ-sarcoglycan.

In any of the provided methods, uses or compositions, the level of gamma-sarcoglycan gene expression in a cell of the subject is increased after administration of the rAAV as compared to the level of gamma-sarcoglycan gene expression before administration of the rAAV.

In addition, in any of the provided methods, uses or compositions, the expression of the gamma-sarcoglycan gene in the cell is detected by measuring the gamma-sarcoglycan protein level on a Western blot or immunohistochemistry in muscle biopsied before and after administration of the rAAV.

In any of the provided methods, uses or compositions, the level of gamma-sarcoglycan protein is increased by at least 25%, or at least 26%, or at least 27%, or at least 28%, or at least 29%, or at least 30%, or at least 31%, or at least 32%, or at least 33%, or at least 34%, or at least or 35% or at least 36%, or at least 37%, or at least 38%, or at least 39%, or at least 40%, or at least 41%, or at least 42%, or at least 43%, or at least 44%, or at least 45% or at least 46%, or at least 47%, or at least 48%, or at least 49%, or at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 85%, or at least 90% or at least 95%, or at least 98% after administration of rAAV. For example, the level of gamma-sarcoglycan protein is increased by at least 33% as detected by measuring the gamma-sarcoglycan protein level on a Western blot in muscle biopsied before and after administration of the rAAV, or the level of gamma-sarcoglycan protein is increased by at least 38% or at least 39% as detected by measuring the gamma-sarcoglycan protein level by immunohistochemistry in muscle biopsies before and after administration of the rAAV.

In any of the methods, uses or compositions provided herein, the serum CK level in the subject is decreased after administration of the rAAV as compared to serum CK level before administration of the rAAV. For example, the serum level CK level in the subject is decreased by at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 81%, or at least 82%, or at least 83%, or at least 84%, or at least 85%, or at least 86% or at least 87%, or at least 88%, or at least 89%, or at least 90% or at least 95%, or at least 98% by 60 to 90 days or 60 days or 90 days after administration of rAAV as compared to the serum CK level before administration of the rAAV.

In any of the methods, uses or compositions provided herein, the number of gamma-sarcoglycan positive fibers in the muscle tissue of the subject is increased after administration of the rAAV as compared to the number of gamma-sarcoglycan positive fibers before administration of the rAAV. For example, the number of gamma-sarcoglycan positive fibers is detected by measuring the gamma-sarcoglycan protein level by Western blot or immunohistochemistry on muscle biopsies before and after administration of the rAAV. For example, the number of gamma-sarcoglycan positive fibers in the muscle tissue of the subject is increased by at least 25%, or at least 26%, or at least 27%, or at least 28%, or at least 29%, or at least 30%, or at least 31%, or at least 32%, or at least 33%, or at least 34%, or at least 35% or at least 36%, or at least 37%, or at least 38%, or at least 39%, or at least 40%, or at least 41%, or at least 42%, or at least 43%, or at least 44%, or at least 45% or at least 46%, or at least 47%, or at least 48%, or at least 49%, or at least 50%, or at least 51%, or at least 52%, or at least 53%, or at least 54%, or at least 55% or at least 56%, or at least 57%, or at least 58%, or at least 59%, or at least 60%, or at least 63%, or at least 65%, or at least 70%, or at least 75%, or at least 80%, or at least 85%, or at least 90% or at least 95%, or at least 98% after administration of rAAV.

In any of the methods, compositions and uses provided herein, the level of alpha-sarcoglycan and/or beta-sarcoglycan in the subject is increased after administration of the rAAV as compared to the level of alpha-sarcoglycan and/or beta-sarcoglycan before administration of the rAAV. In any of the methods, compositions and uses provided herein, the level of beta-sarcoglycan in the subject is increased after administration of the rAAV as compared to the level of beta-sarcoglycan before administration of the rAAV. The level of alpha-sarcoglycan or beta-sarcoglycan is detected by measuring the alpha-sarcoglycan protein level by immunohistochemistry or Western blot on muscle biopsies before and after administration of the rAAV.

Another embodiment provides for methods expressing gamma-sarcoglycan gene in a cell comprising administering to the subjects the scAAVrh74.MHCK7.hSGCG construct nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

Also provided are compositions for expressing gamma-sarcoglycan gene in a cell, wherein the composition comprises the scAAVrh74.MHCK7.hSGCG construct nucleotide sequence that is at least 90%, 95%, or 99% identical to SEQ ID NO: 1 or SEQ ID NO: 7 or SEQ ID NO: 10, or comprising the nucleotide sequence of SEQ ID NO: 1 or SEQ ID NO: 7 or SEQ ID NO: 10.

The disclosure also provides for uses of the scAAVrh74.MHCK7.hSGCG construct nucleotide sequence for the preparation of a medicament for the expressing gamma-sarcoglycan gene in a cell, wherein the scAAVrh74.MHCK7.hSGCG construct nucleotide sequence is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

In any of the provided methods, uses or compositions for expressing gamma-sarcoglycan gene in a cell, expression of the gamma-sarcoglycan gene in the cell is detected by measuring the gamma-sarcoglycan protein level on a Western blot or immunohistochemistry in muscle biopsies before and after administration of the scAAVrh74.MHCK7.hSGCG construct. For example, the cell has more than one AAV viral copy number. In addition, the gamma-sarcoglycan gene is measured in the subject by detecting greater than 1 rAAV vector genome copy per nucleus in at least one cell. In one embodiment, the average rAAV copy number in a muscle cell of the treated subject is at least 0.01 copy per nucleus. In another embodiment, the average rAAV copy number in a muscle cell of the treated subject is at least 0.1 copy per nucleus. In another embodiment, the average rAAV copy number in a muscle cell of the treated subject is at least 1 copy per nucleus. In another embodiment, the average rAAV copy number in a muscle cell of the treated subject is at least 10 copies per nucleus.

Also provided are compositions for decreasing serum CK levels in a subject in need thereof, wherein the composition comprises the scAAVrh74.MHCK7.hSGCG construct nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

The disclosure also provides for uses of the scAAVrh74.MHCK7.hSGCG construct nucleotide sequence for the preparation of a medicament for decreasing serum CK levels in a subject in need thereof, wherein the scAAVrh74.MHCK7.hSGCG construct nucleotide sequence is at least 90%, 95%, or 99% identical to SEQ ID NO:1 or SEQ ID NO: 7 or SEQ ID NO: 10 or comprising the nucleotide sequence of SEQ ID NO: 1 or SEQ ID NO: 7 or SEQ ID NO: 10.

In any of these methods, uses, and compositions, the serum CK level in the subject is decreased by at least 82% by 60 days after administration of the rAAV as compared to the serum CK level before administration of the rAAV.

In any of these methods, uses, and compositions, the number of gamma-sarcoglycan positive fibers is detected by measuring the gamma-sarcoglycan protein level by Western blot or immunohistochemistry on muscle biopsies before and after administration of the rAAV. In addition, in any of the methods, uses and compositions, the number of gamma-sarcoglycan positive fibers is measured by detecting greater than 1 rAAV vector genome copy per nucleus.

Another embodiment provides for methods of increasing the expression of alpha-sarcoglycan in a subject in need thereof comprising administering to the subject the scAAVrh74.MHCK7.hSGCG construct that comprises a nucleotide sequence that is at least 90%, 95%, or 99% identical to SEQ ID NO:1 or SEQ ID NO: 7 or SEQ ID NO: 10 or comprising the nucleotide sequence of SEQ ID NO: 1 or SEQ ID NO: 7 or SEQ ID NO: 10.

Also provided are compositions for increasing the expression of alpha-sarcoglycan in a subject in need thereof, wherein the composition comprises the scAAVrh74.MHCK7.hSGCG construct nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

The disclosure also provides for uses of the scAAVrh74.MHCK7.hSGCG construct nucleotide sequence for the preparation of a medicament for increasing the expression of alpha-sarcoglycan in a subject, wherein the scAAVrh74.MHCK7.hSGCG construct nucleotide sequence is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

Also provided are methods of increasing localization of alpha-sarcoglycan to a cell membrane in a subject in need thereof comprising administering to the subject the scAAVrh74.MHCK7.hSGCG construct nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

Also provided are compositions for increasing localization of alpha-sarcoglycan to a cell membrane in a subject in need thereof, wherein the composition comprises the scAAVrh74.MHCK7.hSGCG construct nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

The disclosure also provides for uses of the scAAVrh74.MHCK7.hSGCG construct nucleotide sequence for the preparation of a medicament for increasing localization of alpha-sarcoglycan and/or beta-sarcoglycan to a cell membrane in a subject in need thereof, wherein the scAAVrh74.MHCK7.hSGCG construct nucleotide sequence is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

In any of these methods, uses and compositions the level of alpha-sarcoglycan is detected by measuring the alpha-sarcoglycan protein level by Western blot or immunohistochemistry on muscle biopsies before and after administration of the rAAV. In addition, in any of the provided methods, uses and compositions, alpha-sarcoglycan is colocalized to the membrane of a cell expressing a gamma-sarcoglycan encoded by scAAVrh74.MHCK7.hSGCG.

Another embodiment provides for methods of increasing sarcoglycan expression in muscle tissue of a subject in need thereof, comprising administering to the subject the scAAVrh74.MHCK7.hSGCG construct that comprises a nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

Also provided are compositions for increasing the expression of sarcoglycan expression in muscle tissue of a subject in need thereof, wherein the composition comprises the scAAVrh74.MHCK7.hSGCG construct nucleotide sequence that is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

The disclosure also provides for uses of the scAAVrh74.MHCK7.hSGCG construct nucleotide sequence for the preparation of a medicament for increasing sarcoglycan expression in muscle tissue of a subject in need thereof, wherein the scAAVrh74.MHCK7.hSGCG construct nucleotide sequence is at least 90%, 95%, or 99% identical to SEQ ID NO: 1 or SEQ ID NO: 7 or SEQ ID NO: 10 or comprising the nucleotide sequence of SEQ ID NO: 1 or SEQ ID NO: 7 or SEQ ID NO: 10.

In any of these methods, uses and compositions for increasing sarcoglycan expression in muscle tissue, the subject suffers from a genetic mutation in a gene encoding a sarcoglycan or a muscular dystrophy. For example, in any of these methods, uses or compositions, the sarcoglycan is γ-sarcoglycan (SGCG), α-sarcoglycan (SGCA), γ-sarcoglycan (SGCG), or δ-sarcoglycan (SGCD).

Methods of producing a recombinant AAV vector particle comprising culturing a cell that is transferred with a plasmid described herein and recovering recombinant AAV particles from the supernatant of the transfected cells are also provided. Viral particles comprising any of the recombinant AAV vectors described herein are also contemplated. In one embodiment, the method of generating the rAAV comprising transferring an AAV vector plasmid to a host cell. In another embodiment, the plasmid comprises a nucleotide sequence that is at least 90%, 95%, or 99% identical to SEQ ID NO: 24. In another aspect, the disclosure provides a cell that comprising an AAV vector plasmid that comprises a nucleotide sequence of SEQ ID NO: 8. The cell described herein comprises an insect cell, e.g., a *Drosophila* cell (e.g., an S2 cell or Kc cell), a silkworm cell (e.g., a Bme21 cell), or a mosquito cell (e.g., a C6/36 cell); or a mammalian cell (preferably a human cell, e.g., a human primary cell or an established cell line). In one embodiment, the mammalian cell comprises a 293 cell, a COS cell, a HeLa cell, or a KB cell.

In another embodiment, the plasmid comprises a nucleotide sequence that is at least 90%, 95%, or 99% identical to SEQ ID NO: 1, or 7 or SEQ ID NO: 10. In some embodiments, the vector plasmid comprises a nucleotide sequence of any one of SEQ ID NO: 1, or 7 or 10. In some embodiments, the AAV vector plasmid is stably expressed in the host cell. The host cell stably harboring the AAV vector plasmid can be used to generate rAAV. In one embodiment, the AAV vector plasmid is a pAAV.MHCK7.hSGCG. KAN plasmid.

The method of producing recombinant AAV vector particles provided herein may further comprise a step of transferring a packaging plasmid and/or a helper virus to the host cell. For example, the methods further comprise a step wherein the packaging cell comprises a stably integrated AAV cap gene and/or wherein the packaging cell comprises a stably integrated AAV rep gene. The invention also provides for a cell comprising a plasmid that comprises a nucleotide sequence that is at least 90%, 95%, or 99% identical to SEQ ID NO: 8 or an plasmid that comprises a nucleotide sequence of SEQ ID NO: 8. Also provided is a cell comprising a nucleotide sequence of SEQ ID NO: 1, or 7.

Methods of reducing fibrosis in a mammalian subject in need thereof is also provided. In this regard, the method comprises administering a therapeutically effective amount of an AAV vector described herein (or composition comprising an AAV vector described herein) to the mammalian subject. In some embodiments, the mammalian subject suffers from muscular dystrophy. In some embodiments, administration of an AAV vector described herein (or composition comprising an AAV vector described herein) reduces fibrosis in skeletal muscle or in cardiac muscle of the subject.

The term "muscular dystrophy" as used herein refers to a disorder in which strength and muscle bulk gradually decline. Non-limiting examples of muscular dystrophy diseases may include Becker muscular dystrophy, tibial muscular dystrophy, Duchenne muscular dystrophy, Emery-Dreifuss muscular dystrophy, facioscapulohumeral muscular dystrophy, sarcoglycanopathies, congenital muscular dystrophy such as congenital muscular dystrophy due to partial LAMA2 deficiency, merosin-deficient congenital muscular dystrophy, type 1D congenital muscular dystrophy, Fukuyama congenital muscular dystrophy, limb-girdle type 1A muscular dystrophy, limb-girdle type 2A muscular dystrophy, limb-girdle type 2B muscular dystrophy, limb-girdle type 2C muscular dystrophy, limb-girdle type 2D muscular dystrophy, limb-girdle type 2E muscular dystrophy, limb-girdle type 2F muscular dystrophy, limb-girdle type 2G muscular dystrophy, limb-girdle type 2H muscular dystrophy, limb-girdle type 2I muscular dystrophy, limb-girdle type 2I muscular dystrophy, limb-girdle type 2J muscular dystrophy, limb-girdle type 2K muscular dystrophy, limb-girdle type IC muscular dystrophy, rigid spine muscular dystrophy with epidermolysis bullosa simplex, oculopharyngeal muscular dystrophy, Ullrich congenital muscular dystrophy, and Ullrich scleroatonic muscular dystrophy. In some embodiments, the subject is suffering from limb-girdle muscular dystrophy. In some embodiments, the subject is suffering from limb-girdle muscular dystrophy type 2C (LGMD2C).

The term "fibrosis" as used herein refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include collagen, e.g. collagen 1, collagen 2 or collagen 3, and fibronectin.

In another aspect, described herein is a method of increasing muscular force and/or muscle mass in a mammalian subject comprising administering a therapeutically effective amount of an AAV vector described herein (or composition comprising an AAV vector described herein) to the mammalian subject. In one embodiment, the subject is a human.

In any of the methods of the invention, the subject may be suffering from muscular dystrophy such as limb-girdle muscular dystrophy or any other dystrophin-associated muscular dystrophy.

Also provided is a method of treating muscular dystrophy in a mammalian subject comprising administering a therapeutically effective amount of an AAV vector described herein (or composition comprising an AAV vector described herein) to the mammalian subject. In some embodiments, the muscular dystrophy is limb-girdle muscular dystrophy.

In any of the methods of the invention, the rAAV is administered by intramuscular injection or intravenous injection. In addition, in any of the method of the invention, the rAAV is administered systemically, such as parental administration by injection, infusion or implantation.

The compositions of the invention are formulated for intramuscular injection or intravenous injection. In addition, the compositions of the invention are formulated for systemic administration, such as parental administration by injection, infusion or implantation.

In any of the provided formulations or compositions, the buffer agent comprises one or more of tris, tricine, Bis-tricine, HEPES, MOPS, TES, TAPS, PIPES, and CAPS. For example, the buffer agent comprises the tris with pH 8.0 at concentration of about 5 mM to about 40 mM or the buffer agent comprises the tris with pH 8.0 at about 20 mM.

In any of the provided formulations or compositions, the ionic strength agent comprises one or more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. For example, the ionic strength agent comprises $MgCl_2$ at a concentration of about 0.2 mM to about 4 mM or the ionic strength agent comprises NaCl at a concentration of about 50 mM to about 500 mM, or the ionic strength agent comprises $MgCl_2$ at a concentration of about 0.2 mM to about 4 mM and NaCl at a concentration of about 50 mM to about 500 mM, or the ionic strength agent comprises $MgCl_2$ at a concentration of about 1 mM and NaCl at a concentration of about 200 mM.

In any of the provided formulations or compositions, the surfactant comprises one or more of a sulfonate, a sulfate, a phosphonate, a phosphate, a Poloxamer, and a cationic surfactant. For example, the Poloxamer comprises one or more of Poloxamer 124, Poloxamer 181, Poloxamer 184, Poloxamer 188, Poloxamer 237, Poloxamer 331, Poloxamer 338, and Poloxamer 407. The Poloxamer may be at a concentration of about 0.00001% to about 1%. An exemplary surfactant is Poloxamer 188 at a concentration of about 0.001%.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

The patent or application file contains at least one drawing executed in color. Copies of this patent or patent application publication with color drawing(s) will be provided by the Office upon request and payment of the necessary fee.

BRIEF DESCRIPTION OF THE FIGURES

FIG. 2A shows the immunofluorescence imaging of skeletal muscles, diaphragm, and heart from SGCG$^{-/-}$ mice intravenously injected with low-dose, mid-dose, and high-dose scAAVrh.74.MHCK7.hSGCG. FIG. 2B shows the percentages of fibers with SGCG protein expression at low-dose, mid-dose, and high-dose.

FIG. 3A shows the immunofluorescence imaging of DAPC protein expressions. FIG. 3B shows the percentages of fibers with DAPC protein expression at low-dose, mid-dose, and high-dose.

FIG. 4A shows H&E stain of quadriceps and diaphragm muscle from BL/6 WT, SGCG–/–, and scAAVrh.74.MHCK7.hSGCG treated mice at low-dose, mid-dose, and high-dose; FIG. 4B shows trichrome staining for fibrosis; FIG. 4C shows percentage of centralized nuclei; FIG. 4D shows percentage of fibrois.

FIGS. 7A and 7B shows the physical activities of mice after treatment with scAAVrh.74.MHCK7.hSGCG at low-dose, mid-dose, and high-dose.

FIGS. 8A, 8B and 8C provides CK and chemistry analysis of mice after treatment with scAAVrh.74.MHCK7.hSGCG at low-dose, mid-dose, and high-dose.

FIG. 9 provides a schematic map of pAAV.MHCK7.hSGCG. KAN AAV vector plasmid.

DETAILED DESCRIPTION

Figure 1:
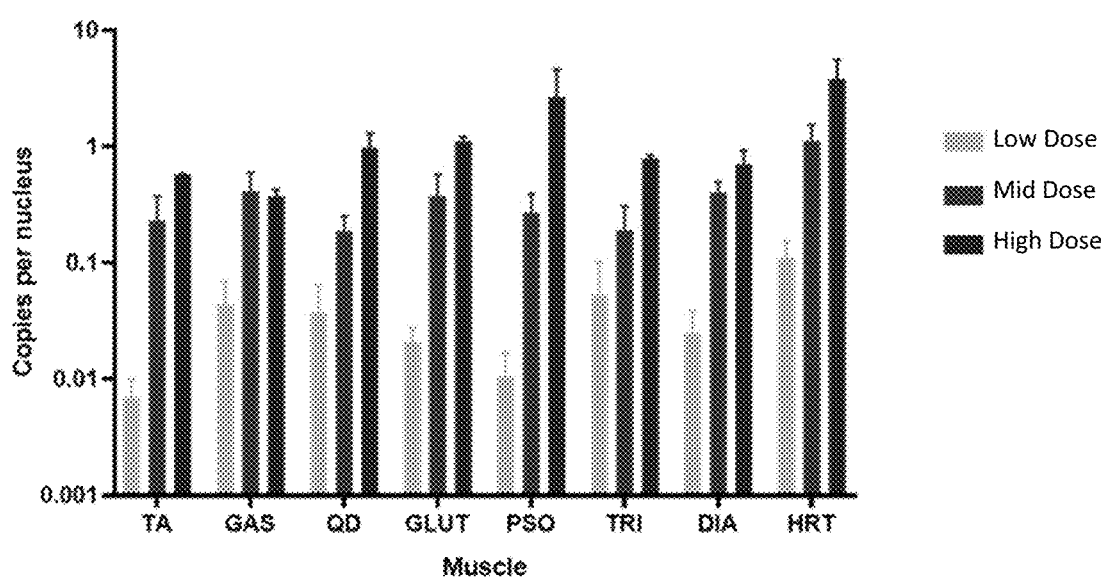
FIG. 1 shows the biodistribution of vector genome copies in various parts of skeletal muscle after the mice were administered with low-, mid-, and high-dose rAAV.MHCK7.hSGCBSGCG.

The present disclosure is based on the discovery that administration of an AAV vector comprising a polynucleotide expressing γ-sarcoglycan results in a reduction or complete reversal of muscle fibrosis or restoration of sarcoglycan complex proteins in a limb-girdle muscular dystrophy animal model. As demonstrated in the Examples, administration of the AAV vector described herein resulted in the reversal of dystrophic features including fewer degenerating fibers, increased ambulation, reduced CK level, reduced inflammation and improved functional recovery by protection against eccentric contraction with increased force generation.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector," as used herein, refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion," or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle. AAV Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV rh.10 and AAV rh.74. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote skeletal muscle specific expression, AAV-1, AAV-5, AAV-6, AAVrh74, AAV-8 or AAV-9 may be used.

DNA plasmids of the invention comprise rAAV genomes. The DNA plasmids are transferred to cells permissible for infection with a helper virus of AAV (e.g., adenovirus, E1-deleted adenovirus or herpes virus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692, which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., *Proc. Natl. Acad. Sci USA*, 79:2077-2081 (1982)), addition of synthetic linkers containing restriction endonuclease cleavage sites (Laughlin et al., *Gene* 23:65-73 (1983)) or by direct, blunt-end ligation (Senapathy & Carter, *J. Biol. Chem.* 259:4661-4666 (1984)). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Tratschin et al., *Mol. Cell. Biol.* 4:2072 (1984); Hermonat et al., *Proc. Natl. Acad. Sci. USA*, 81:6466 (1984); Tratschin et al., *Mol. Cell. Biol.* 5:3251 (1985); McLaughlin et al., *J. Virol.* 62:1963 (1988); and Lebkowski et al., *Mol. Cell. Biol.* 7:349 (1988). Samulski et al., *J. Virol.* 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al., *Vaccine* 13:1244-1250 (1995); Paul et al., *Human Gene Therapy* 4:609-615 (1993); Clark et al., *Gene Therapy* 3:1124-1132 (1993); U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, the rAAV named pAAV.MHCK7.hSGCG which comprises the polynucleotide sequence set forth in SEQ ID NO: 1 or SEQ ID NO: 7.

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schnepp and Clark, *Methods Mol. Med.*, 69 427-443 (2002); U.S. Pat. No. 6,566,118 and WO 98/09657.

In another embodiment, the invention contemplates compositions comprising rAAV of the present invention. Compositions described herein comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg). The titers of rAAV may be determined by the supercoiled plasmid quantitation standard or the linearized plasmid quantitation standard.

In one embodiment, the disclosure provides methods of measuring the titer of an AAV vector, comprising tittering the AAV vector with PCR with a first primer of SEQ ID NO: 13 and a second primer of SEQ ID NO: 14. In another embodiment, methods of measuring the titer of an AAV vector, comprising tittering the AAV vector with using a probe comprising a sequence of SEQ ID NO: 15. The probe, in one embodiment, comprise 5'-FAM-TGG ATC CCC-Zen-TGC ATG CGA AGA TC-3IABKFQ. In another embodiment, the AAV vector is an scAAVrh74.MHCK7.hSGCG.

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is muscular dystrophy, such as limb-girdle muscular dystrophy. Thus, provided is a method of transducing a target cell with an rAAV scAAVrh74.MHCK7.hSGCG, which comprises a nucleotide sequence of SEQ ID NO: 1 or 7. The disclosure also provides a primer of SEQ ID NO: 11. In another embodiment, the disclosure provides a primer of SEQ ID NO: 12. In one embodiment, the disclosure provides a method of measuring SGCG expression in a cell or a subject, wherein the method comprises a PCR analysis with the primers of SEQ ID NO: 11 and SEQ ID NO: 12. In one embodiment, the subject suffers from a LGMD. In one embodiment, the method comprises measuring expression of the scAAVrh74.MHCK7.hSGCG vector in the cell or the patient.

Combination therapies are also contemplated by the invention. Combination as used herein includes both simultaneous treatment or sequential treatments. Combinations of methods of the invention with standard medical treatments (e.g., steroids, corticosteroids, and/or glucocorticoids including but not limited to one or more of prednisone, prednisolone; and deflazacort) are specifically contemplated, as are combinations with novel therapies. In this regard, the combinations include administering to a subject one or more steroids, corticosteroids, and/or glucocorticoids including but not limited to one or more of prednisone, prednisolone; and deflazacort before administering an rAAV of the inventive methods to the subject, simultaneously with administering the rAAV to the subject, or after administering the rAAV to the subject.

In related embodiments of a combination therapy contemplated by the invention, the glucocorticoid includes, but is not limited to beclomethasone, betamethasone, budesonide, cortisone, dexamethasone, hydrocortisone, methylprednisolone, or triamcinolone.

It is recognized that an antigen specific T-cell response may occur in a subject administered with the rAAV vector. This is an expected response between 2-4 weeks following gene transfer. One possible consequence to such antigen specific T-cell responses is clearance of the transduced cells and loss of transgene expression. To dampen the host immune response to the rAAV based therapy, before the therapy, for example, twenty-four hours prior to the therapy procedure, subjects can be started on approximately 1 mg/kg/day prophylactic prednisone or comparable glucocorticoid by mouth with a maximum dose of 60 mg/day. IV administration of a comparable glucocorticoid at the approximate dose of 1 mg/kg/day would also be allowable if needed. Treatment will continue for approximately one month. A tapering protocol for prednisone or comparable glucocorticoid can be implemented based on individual subjects' immune response to the gene transfer, assessed by ELISpot assay and also by liver function monitoring with GGT.

A therapeutically effective amount of the rAAV vector is a dose of rAAV ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, 9e14 vg/kg, 1e15 vg/kg, 2e15 vg/kg, 3e15 vg/kg, 4e15 vg/kg, 5e15 vg/kg, 6e15 vg/kg, 7e15 vg/kg, 8e15 vg/kg, 9e15 vg/kg, or 1e16 vg/kg. The invention also comprises compositions comprising these ranges of rAAV vector. In one embodiment, the dosage is based on a linearized plasmid as the quantitation standard. In one embodiment, the dosage is based on a supercoiled plasmid as the quantitation standard.

For example, a therapeutically effective amount of rAAV vector is a dose of 1e13 vg/kg, about 2e13 vg/kg, about 3e13 vg/kg, about 4e13 vg/kg, about 5e13 vg/kg, about 6e13 vg/kg, about 7e13 vg/kg, about 7.4e13 vg/kg, about 8e13 vg/kg, about 9e13 vg/kg, about 1e14 vg/kg, about 2e14 vg/kg, about 3e14 vg/kg, about 4e14 vg/kg, about 5e14 vg/kg, about 6e14 vg/kg, about 7e14 vg/kg, about 8e14 vg/kg, about 9e14 vg/kg, about 1e15 vg/kg, about 2e15 vg/kg, about 3e15 vg/kg, about 4e15 vg/kg, about 5e15 vg/kg, about 6e15 vg/kg, about 7e15 vg/kg, about 8e15 vg/kg, about 9e15 vg/kg, or about 1e16 vg/kg. The titer or dosage of AAV vectors can vary based on the physical forms of plasmid DNA as a quantitation standard. For example, the value of titer or dosage may vary based off of a supercoiled standard qPCR titering method or a linear standard qPCR titering method. In one embodiment, a therapeutically effective amount of rAAV is a dose of 5e13 vg/kg based on a supercoiled plasmid as the quantitation standard or a dose of 1.85e13 vg/kg based on a linearized plasmid as the quantitation standard. In another embodiment, a therapeutically effective amount of rAAV is a dose of 2e14 vg/kg based on the supercoiled plasmid as the quantitation standard or a dose of 7.41e13 vg/kg based on the linearized plasmid as the quantitation standard. In another embodiment, a therapeutically effective amount of rAAV is a dose of about $4.63 \times 10^{12}$ vg/kg based on the linearized plasmid as the quantitation standard or about $1.25 \times 10^{13}$ vg/kg based on a supercoiled plasmid as the quantitation standard. In another embodiment, the therapeutically effective amount of scAAVrh74.MHCK7.hSGCG is a dose ranging from about 1e13 vg/kg to about 5e14 vg/kg, or about 1e13 vg/kg to about 2e13 vg/kg, or about 1e13 vg/kg to about 3e13 vg/kg, or about 1e13 vg/kg to about 4e13 vg/kg, or about 1e13 vg/kg to about 5e13 vg/kg, or about 1e13 vg/kg to about 6e13 vg/kg, or about 1e13 vg/kg to about 7e13 vg/kg, or about 1e13 vg/kg to about 8e13 vg/kg, or about 1e13 vg/kg to about 9e13 vg/kg, or about 1e13 vg/kg to about 1e14 vg/kg, or about 1e13 vg/kg to about 2e14 vg/kg, or 1e13 vg/kg to about 3e14 vg/kg, or about 1e13 to about 4e14 vg/kg, or about 3e13 vg/kg to about 4e13 vg/kg, or about 3e13 vg/kg to about 5e13 vg/kg, or about 3e13 vg/kg to about 6e13 vg/kg, or about 3e13 vg/kg to about 7e13 vg/kg, or about 3e13 vg/kg to about 8e13 vg/kg, or about 3e13 vg/kg to about 9e13 vg/kg, or about 3e13 vg/kg to about 1e14 vg/kg, or about 3e13 vg/kg to about 2e14 vg/kg, or 3e13 vg/kg to about 3e14 vg/kg, or about 3e13 to about 4e14 vg/kg, or about 3e13 vg/kg to about 5e14 vg/kg, or about 5e13 vg/kg to about 6e13 vg/kg, or about 5e13 vg/kg to about 7e13 vg/kg, or about 5e13 vg/kg to about 8e13 vg/kg, or about 5e13 vg/kg to about 9e13 vg/kg, or about 5e13 vg/kg to about 1e14 vg/kg, or about 5e13 vg/kg to about 2e14 vg/kg, or 5e13 vg/kg to about 3e14 vg/kg, or about 5e13 to about 4e14 vg/kg, or about 5e13 vg/kg to about 5e14 vg/kg, or about 1e14 vg/kg to about 2e14 vg/kg, or 1e14 vg/kg to about 3e14 vg/kg, or about 1e14 to about 4e14 vg/kg, or about 1e14 vg/kg to about 5e14 vg/kg, 6e14 vg/kg, 7e14 vg/kg, 8e14 vg/kg, 9e14 vg/kg, 1e15 vg/kg, 2e15 vg/kg, 3e15 vg/kg, 4e15 vg/kg, 5e15 vg/kg, 6e15 vg/kg, 7e15 vg/kg, 8e15 vg/kg, 9e15 vg/kg, or 1e16 vg/kg, based on the supercoiled plasmid as the quantitation standard. The invention also comprises compositions comprising these doses of rAAV vector.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the γ-sarcoglycan.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein.

Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling. Thus, in another aspect, the application is directed to a formulation that comprises an rAAV that comprises an AAVrh74 derived capsid, a buffer agent, an ionic strength agent, and a surfactant. In one embodiment, the rAAV is at a concentration of $1.0 \times 10^{12}$ vg/ml to about $1.0 \times 10^{16}$ vg/ml or about $1.0 \times 10^{12}$ vg/ml to about $5.0 \times 10^{14}$ vg/ml. In another embodiment, the rAAV is at a concentration of about $5.0 \times 10^{12}$ vg/ml to about $1.0 \times 10^{14}$ vg/ml based on a supercoiled plasmid as the quantitation standard. In another embodiment, the rAAV is at a concentration of about $5.0 \times 10^{12}$ vg/ml to about $1.0 \times 10^{14}$ vg/ml based on a linearized plasmid as the quantitation standard. In another embodiment, the rAAV is at a concentration of about $2.0 \times 10^{13}$ vg/ml based on a supercoiled plasmid as the quantitation standard. In one embodiment, the rAAV is an scAAVrh74.MHCK7.hSGCG vector. In one embodiment, the concentration of rAAV in the composition or formulation is from $1 \times 10^{13}$ vg/ml to $2 \times 10^{14}$ vg/ml based on a supercoiled plasmid as the quantitation standard. In another embodiment, the concentration is $2 \times 10^{13}$ vg/ml, $4 \times 10^{13}$ vg/ml, or $5 \times 10^{13}$ vg/ml based on a supercoiled plasmid as the quantitation standard. In one embodiment, the buffer agent comprises one or more of tris, tricine, Bis-tricine, HEPES, MOPS, TES, TAPS, PIPES, and CAPS. In another embodiment, the buffer agent comprises tris with pH 8.0 at concentration of about 5 mM to about 40 mM. In one embodiment, the buffer agent comprises tris with pH 8.0 at about 20 mM. In one embodiment, the ionic strength agent comprises one of more of potassium chloride (KCl), potassium acetate, potassium sulfate, ammonium sulfate, ammonium chloride ($NH_4Cl$), ammonium acetate, magnesium chloride ($MgCl_2$), magnesium acetate, magnesium sulfate, manganese chloride ($MnCl_2$), manganese acetate, manganese sulfate, sodium chloride (NaCl), sodium acetate, lithium chloride (LiCl), and lithium acetate. In one embodiment, the ionic strength agent comprises $MgCl_2$ at a concentration of about 0.2 mM to about 4 mM. In another embodiment, the ionic strength agent comprises NaCl at a concentration of about 50 mM to about 500 mM. In another embodiment, the ionic strength agent comprises $MgCl_2$ at a concentration of about 0.2 mM to about 4 mM and NaCl at a concentration of about 50 mM to about 500 mM. In another embodiment, the ionic strength agent comprises $MgCl_2$ at a concentration of about 1 mM and NaCl at a concentration of about 200 mM. In one embodiment, the surfactant comprises one or more of a sulfonate, a sulfate, a phosphonate, a phosphate, a Poloxamer, and a cationic surfactant. In one embodiment, the Poloxamer comprises one or more of Poloxamer 124, Poloxamer 181, Poloxamer 184, Poloxamer 188, Poloxamer 237, Poloxamer 331, Poloxamer 338, and Poloxamer 407. In one embodiment, the surfactant comprises the Poloxamer at a concentration of about 0.00001% to about 1%. In another embodiment, the surfactant comprises Poloxamer 188 at a concentration of about 0.001%. For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of γ-sarcoglycan. The present invention thus provides methods of administering/delivering rAAV which express γ-sarcoglycan to a mammalian subject, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251: 761-766 (1991)], the myocyte-specific enhancer binding factor MEF-2 [Cserjesi and Olson, *Mol Cell Biol* 11: 4854-4862 (1991)], control elements derived from the human skeletal actin gene [Muscat et al., *Mol Cell Biol,* 7: 4089-4099 (1987)], the cardiac actin gene, muscle creatine kinase sequence elements [See Johnson et al., *Mol Cell Biol,* 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA,* 88: 5680-5684 (1991)), steroid-inducible elements and promoters including the glucocorticoid response element (GRE) (See Mader and White, *Proc. Natl. Acad. Sci. USA* 90: 5603-5607 (1993)), and other control elements.

Muscle tissue is an attractive target for in vivo DNA delivery, because it is not a vital organ and is easy to access. The invention contemplates sustained expression of miR-NAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of a polynucleotide of interest (e.g., a polynucleotide sequence encoding γ-sarcoglycan) to a recipient cell either in vivo or in vitro, via a replication-deficient rAAV described resulting in expression of γ-sarcoglycan by the recipient cell.

Thus, also described herein are methods of administering an effective dose (or doses, administered essentially simultaneously or doses given at intervals) of rAAV that encode γ-sarcoglycan to a mammalian subject in need thereof.

All publications and patents mentioned herein are hereby incorporated by reference in their entirety as if each individual publication or patent was specifically and individually indicated to be incorporated by reference. In case of conflict, the present application, including any definitions herein, will control.

The invention is further described in the following Examples, which do not limit the scope of the invention described in the claims.

In another embodiment, the disclosure provides a method of generating the rAAV pAAV.MHCK7.hSGCG, which comprises transferring an AAV vector plasmid to a host cell. The methods of transferring a DNA to a host cell are known in the art, which include but are not limited to transfection, infection, transformation, electroporation, and transduction. In one embodiment, the vector plasmid comprises a nucleotide sequence that is at least 90%, 95%, or 99% identical to SEQ ID NO: 8. In another embodiment, the vector plasmid comprises a nucleotide sequence of SEQ ID NO: 8. In another aspect, the disclosure provides a host cell comprising an AAV vector plasmid that comprises a nucleotide sequence of SEQ ID NO: 8. In some embodiment, the AAV vector plasmid is stably expressed in the host cell. The host cell stably harboring the AAV vector plasmid can be used to generate rAAV. In one embodiment, the AAV vector plasmid is a pAAV.MHCK7.hSGCG. KAN plasmid. The pAAV.MHCK7.hSGCG. KAN plasmid is illustrated in FIG. 9.

TABLE 1

Examples of Protein and Nucleotide Sequences

| Sequence Description | Sequence | SEQ ID NO |
|---|---|---|
| Human γ-Sarcoglycan nucleotide sequence (codon-optimized) | ATGGTGAGGGAGCAGTACACCACAGCAACCGAGGG AATCTGCATCGAGAGGCCAGAGAACCAGTACGTGTATAAGATCG GCATCTACGGCTGGCGGAAGAGATGTCTGTATCTGTTCGTGCTGC TGCTGCTGATCATCCTGGTGGTGAATCTGGCCCTGACCATCTGGA TCCTGAAAGTGATGTGGTTTTCCCCAGCAGGAATGGGACACCTGT GCGTGACAAAGGACGGACTGCGGCTGGAGGGAGAGTCTGAGTTC CTGTTTCCCCTGTATGCCAAGGAGATCCACAGCAGAGTGGATAGC TCCCTGCTGCTGCAGTCCACCCAGAACGTGACAGTGAACGCAAG GAATAGCGAGGGAGAGGTGACCGGCAGACTGAAGGTCGGCCCCA AGATGGTGGAGGTGCAGAATCAGCAGTTCCAGATCAACTCCAAT GACGGCAAGCCTCTGTTTACAGTGGATGAGAAGGAGGTGGTGGT GGGCACCGACAAGCTGAGGGTGACAGGACCTGAGGGCGCCCTGT TCGAGCACTCTGTGGAGACCCCACTGGTGCGCGCAGACCCTTTTC AGGATCTGAGGCTGGAGAGCCCAACACGCAGCCTGTCCATGGAC GCACCCAGAGGCGTGCACATCCAGGCACACGCAGGCAAGATCGA GGCCCTGAGCCAGATGGATATCCTGTTCCACTCTAGCGACGGCAT GCTGGTGCTGGATGCCGAGACCGTGTGCCTGCCTAAGCTGGTGCA GGGCACATGGGGCCCATCTGGCTCCTCTCAGAGCCTGTACGAGAT CTGCGTGTGCCCAGATGGCAAGCTGTATCTGTCCGTGGCCGGCGT GTCTACCACATGCCAGGAGCACAACCACATCTGTCTGTGA | 1 |
| MHCK7 promoter sequence | AAG CTTGCATGTC TAAGCTAGAC CCCTTCAGATT AAAAATAACT GAGGTAAGGGCCTGGGTAGG GGAGGTGGTGTGAGACGCTC CTGTCTCTCCTCTATCTGCCCATCGGCCCTTTGGGGAGGAGGAAT GTGCC CAAGGACTAA AAAAAGGCCA TGGAGCCAGA GGGGCGAGGGCAACAGACCT TTCATGGGCA AACCTTGGGG CCCTGCTGTC TAGCATGCCCCACTACGGGT CTAGGCTGCC CATGTAAGGA GGCAAGGCCT GGGGACACCCGAGATGCCTG GTTATAATTA ACCCAGACAT GTGGCTGCCC CCCCCCCCCC AACACCTGCT GCCTCTAAAA ATAACCCTGT CCCTGGTGGA TCCCCTGCATGCGAAGATCT TCGAACAAGG CTGTGGGGGA CTGAGGGCAG GCTGTAACAGGCTTGGGGGC CAGGGCTTAT ACGTGCCTGG GACTCCCAAA GTATTACTGTTCCATGTTCC CGGCGAAGGG CCAGCTGTCC CCCGCCAGCT AGACTCAGCA CTTAGTTTAG GAACCAGTGA GCAAGTCAGC CCTTGGGGCA GCCCATACAA GGCCATGGGG CTGGGCAAGC TGCACGCCTG GGTCCGGGGT GGGCACGGTG CCCGGGCAAC GAGCTGAAAG CTCATCTGCT CTCAGGGGCC CCTCCCTGGG GACAGCCCCT CCTGGCTAGT CACACCCTGT AGGCTCCTCT ATATAACCCA GGGGCACAGG GGCTGCCCTC ATTCTACCAC CACCTCCACA GCACAGACAGACACTCAGGA GCAGCCAGC | 2 |
| 5'ITR | CTGCGCGCTCGCTCGCTCACTGAGGCCGCCCGGGCAAAGCCCGG GCGTCGGGCGACCTTTGGTCGCCCGGCCTCAGTGAGCGAGCGAG CGCGCAGAGAGGGAGTGG | 3 |
| 3'ITR | AGGAACCCCTAGTGA TGGAGTTGGC CACTCCCTCT CTGCGCGCTC GCTCGCTCAC TGAGGCCGGG CGACCAAAGG TCGCCCGACG CCCGGGCTTT GCCCGGGCGG CCTCAGTGAG CGAGCGAGCG CGCAG | 4 |
| Poly A sequence | GGC CGCAATAAAA GATCTTTATT TTCATTAGATCTGTGTGTTG GTTTTTTGTG | 5 |
| Intron sequence | AG GTAAGTTTAG TCTTTTTGTC TTTTATTTCA GGTCCCGGAT CCGGTGGTGG TGCAAATCAA AGAACTGCTC CTCAGTGGAT GTTGCCTTTA CTTCTAGGCC TGTACGGAAG TGTTACTTCT GCTCTAAAAG CTGCGGAATT GTACCC | 6 |

TABLE 1-continued

Examples of Protein and Nucleotide Sequences

| Sequence Description | Sequence | SEQ ID NO |
|---|---|---|
| Expression cassette polynucleotide sequence 5'ITR Through 3'ITR | CTGCGCGCTC GCTCGCTCAC TGAGGCCGCC CGGGCAAAGC CCGGGCGTCG GGCGACCTTT GGTCGCCCGG CCTCAGTGAG CGAGCGAGCG CGCAGAGAGG GAGTGGGGTT AACCAATTGG CGGCCGCAAG CTTGCATGTC TAAGCTAGAC CCTTCAGATT AAAAATAACT GAGGTAAGGG CCTGGGTAGG GGAGGTGGTG TGAGACGCTC CTGTCTCTCC TCTATCTGCC CATCGGCCCT TTGGGGAGGA GGAATGTGCC CAAGGACTAA AAAAAGGCCA TGGAGCCAGA GGGGCGAGGG CAACAGACCT TTCATGGGCA AACCTTGGGG CCCTGCTGTC TAGCATGCCC CACTACGGGT CTAGGCTGCC CATGTAAGGA GGCAAGGCCT GGGGACACCC GAGATGCCTG GTTATAATTA ACCCAGACAT GTGGCTGCCC CCCCCCCCCC AACACCTGCT GCCTCTAAAA ATAACCCTGT CCCTGGTGGA TCCCCTGCAT GCGAAGATCT TCGAACAAGG CTGTGGGGGA CTGAGGGCAG GCTGTAACAG GCTTGGGGGC CAGGGCTTAT ACGTGCCTGG GACTCCCAAA GTATTACTGT TCCATGTTCC CGGCGAAGGG CCAGCTGTCC CCCGCCAGCT AGACTCAGCA CTTAGTTTAG GAACCAGTGA GCAAGTCAGC CCTTGGGCA GCCCATACAA GGCCATGGGG CTGGGCAAGC TGCACGCCTG GGTCCGGGGT GGGCACGGTG CCCGGGCAAC GAGCTGAAAG CTCATCTGCT CTCAGGGGCC CCTCCCTGGG GACAGCCCCT CCTGGCTAGT CACACCCTGT AGGCTCCTCT ATATAACCCA GGGGCACAGG GGCTGCCCTC ATTCTACCAC CACCTCCACA GCACAGACAG ACACTCAGGA GCAGCCAGCG GCGCGCCCAG GTAAGTTTAG TCTTTTTGTC TTTTATTTCA GGTCCCGGAT CCGGTGGTGG TGCAAATCAA AGAACTGCTC CTCAGTGGAT GTTGCCTTTA CTTCTAGGCC TGTACGGAAG TGTTACTTCT GCTCTAAAAG CTGCGGAATT GTACCCGGTA CCACCATGGT GAGGGAGCAG TACACCACAG CAACCGAGGG AATCTGCATC GAGAGGCCAG AGAACCAGTA CGTGTATAAG ATCGGCATCT ACGGCTGGCG GAAGAGATGT CTGTATCTGT TCGTGCTGCT GCTGCTGATC ATCCTGGTGG TGAATCTGGC CCTGACCATC TGGATCCTGA AAGTGATGTG GTTTTCCCCA GCAGGAATGG GACACCTGTG CGTGACAAAG GACGGACTGC GGCTGGAGGG AGAGTCTGAG TTCCTGTTTC CCCTGTATGC CAAGGAGATC CACAGCAGAG TGGATAGCTC CCTGCTGCTG CAGTCCACCC AGAACGTGAC AGTGAACGCA AGGAATAGCG AGGGAGAGGT GACCGGCAGA CTGAAGGTCG GCCCCAAGAT GGTGGAGGTG CAGAATCAGC AGTTCCAGAT CAACTCCAAT GACGGCAAGC CTCTGTTTAC AGTGGATGAG AAGGAGGTGG TGGTGGGCAC CGACAAGCTG AGGGTGACAG GACCTGAGGG CGCCCTGTTC GAGCACTCTG TGGAGACCCC ACTGGTGCGC GCAGACCCTT TTCAGGATCT GAGGCTGGAG AGCCCAACAC GCAGCCTGTC CATGGACGCA CCCAGAGGCG TGCACATCCA GGCACACGCA GGCAAGATCG AGGCCCTGAG CCAGATGGAT ATCCTGTTCC ACTCTAGCGA CGGCATGCTG GTGCTGGATG CCGAGACCGT GTGCCTGCCT AAGCTGGTGC AGGGCACATG GGGCCCATCT GGCTCCTCTC AGAGCCTGTA CGAGATCTGC GTGTGCCCAG ATGGCAAGCT GTATCTGTCC GTGGCCGGCG TGTCTACCAC ATGCCAGGAG CACAACCACA TCTGTCTGTG ACTCGAGGGC CGCAATAAAA GATCTTTATT TTCATTAGAT CTGTGTGTTG GTTTTTTGTG TGTCCTGCAG GGGCGCGCCT AATCTAGAGC ATGGCTACGT AGATAAGTAG CATGGCGGGT TAATCATTAA CTACAAGGAA CCCCTAGTGA TGGAGTTGGC CACTCCCTCT CTGCGCGCTC GCTCGCTCAC TGAGGCCGGG CGACCAAAGG TCGCCCGACG CCCGGGCTTT GCCCGGGCGG CCTCAGTGAG CGAGCGAGCG CGCAG | 7 |
| pAAV.MHCK7.hSGCG.KAN plasmid sequence | CAGCTGCGCGCTCGCTCGCTCACTGAGGCCGCCCGGGCAAAGCCC GGGCGTCGGGCGACCTTTGGTCGCCCGGCCTCAGTGAGCGAGCG AGCGCGCAGAGAGGGAGTGGGGTTAACCAATTGGCGGCCGCAAG CTTGCATGTCTAAGCTAGACCCTTCAGATTAAAAATAACTGAGGT AAGGGCCTGGGTAGGGGAGGTGGTGTGAGACGCTCCTGTCTCTCC TCTATCTGCCCATCGGCCCTTTGGGGAGGAGGAATGTGCCCAAGG ACTAAAAAAAGGCCATGGAGCCAGAGGGGCGAGGGCAACAGAC CTTTCATGGGCAAACCTTGGGGCCCTGCTGTCTAGCATGCCCCAC TACGGGTCTAGGCTGCCCATGTAAGGAGGCAAGGCCTGGGGACA CCCGAGATGCCTGGTTATAATTAACCCAGACATGTGGCTGCCCCC CCCCCCCAACACCTGCTGCCTCTAAAAATAACCCTGTCCCTGGT GGATCCCCTGCATGCGAAGATCTTCGAACAAGGCTGTGGGGGAC TGAGGGCAGGCTGTAACAGGCTTGGGGGCCAGGGCTTATACGTG CCTGGGACTCCCAAAGTATTACTGTTCCATGTTCCCGGCGAAGGG CCAGCTGTCCCCCGCCAGCTAGACTCAGCACTTAGTTTAGGAACC AGTGAGCAAGTCAGCCCTTGGGCAGCCCATACAAGGCCATGGG GCTGGGCAAGCTGCACGCCTGGGTCCGGGGTGGGCACGGTGCCC GGGCAACGAGCTGAAAGCTCATCTGCTCTCAGGGGCCCCTCCCTG | 8 |

TABLE 1-continued

Examples of Protein and Nucleotide Sequences

| Sequence Description | Sequence | SEQ ID NO |
|---|---|---|
| | GGGACAGCCCCTCCTGGCTAGTCACACCCTGTAGGCTCCTCTATA | |
| | TAACCCAGGGGCACAGGGGCTGCCCTCATTCTACCACCACCTCCA | |
| | CAGCACAGACAGACACTCAGGAGCAGCCAGCGGCGCGCCCAGGT | |
| | AAGTTTAGTCTTTTTGTCTTTTATTTCAGGTCCCGGATCCGGTGGT | |
| | GGTGCAAATCAAAGAACTGCTCCTCAGTGGATGTTGCCTTTACTT | |
| | CTAGGCCTGTACGGAAGTGTTACTTCTGCTCTAAAAGCTGCGGAA | |
| | TTGTACCCGGTACCACCATGGTGAGGGAGCAGTACACCACAGCA | |
| | ACCGAGGGAATCTGCATCGAGAGGCCAGAGAACCAGTACGTGTA | |
| | TAAGATCGGCATCTACGGCTGGCGGAAGAGATGTCTGTATCTGTT | |
| | CGTGCTGCTGCTGCTGATCATCCTGGTGGTGAATCTGGCCCTGAC | |
| | CATCTGGATCCTGAAAGTGATGTGGTTTTCCCCAGCAGGAATGGG | |
| | ACACCTGTGCGTGACAAAGGACGGACTGCGGCTGGAGGGAGAGT | |
| | CTGAGTTCCTGTTTCCCCTGTATGCCAAGGAGATCCACAGCAGAG | |
| | TGGATAGCTCCCTGCTGCTGCAGTCCACCCAGAACGTGACAGTGA | |
| | ACGCAAGGAATAGCGAGGGAGAGGTGACCGGCAGACTGAAGGT | |
| | CGGCCCCAAGATGGTGGAGGTGCAGAATCAGCAGTTCCAGATCA | |
| | ACTCCAATGACGGCAAGCCTCTGTTTACAGTGGATGAGAAGGAG | |
| | GTGGTGGTGGGCACCGACAAGCTGAGGGTGACAGGACCTGAGGG | |
| | CGCCCTGTTCGAGCACTCTGTGGAGACCCCACTGGTGCGCGCAGA | |
| | CCCTTTTCAGGATCTGAGGCTGGAGAGCCCAACACGCAGCCTGTC | |
| | CATGGACGCACCCAGAGGCGTGCACATCCAGGCACACGCAGGCA | |
| | AGATCGAGGCCCTGAGCCAGATGGATATCCTGTTCCACTCTAGCG | |
| | ACGGCATGCTGGTGCTGGATGCCGAGACCGTGTGCCTGCCTAAGC | |
| | TGGTGCAGGGCACATGGGGCCCATCTGGCTCCTCTCAGAGCCTGT | |
| | ACGAGATCTGCGTGTGCCCAGATGGCAAGCTGTATCTGTCCGTGG | |
| | CCGGCGTGTCTACCACATGCCAGGAGCACAACCACATCTGTCTGT | |
| | GACTCGAGGGCCGCAATAAAAGATCTTTATTTTCATTAGATCTGT | |
| | GTGTTGGTTTTTTGTGTGTCCTGCAGGGGCGCGCCTAATCTAGAG | |
| | CATGGCTACGTAGATAAGTAGCATGGCGGGTTAATCATTAACTAC | |
| | AAGGAACCCCTAGTGATGGAGTTGGCCACTCCCTCTCTGCGCGCT | |
| | CGCTCGCTCACTGAGGCCGGGCGACCAAAGGTCGCCCGACGCCC | |
| | GGGCTTTGCCCGGGCGGCCTCAGTGAGCGAGCGAGCGCGCAGCT | |
| | GGCGTAATAGCGAAGAGGCCCGCACCGATCGCCCTTCCCAACAG | |
| | TTGCGCAGCCTGAATGGCGAATGGCGATTCCGTTGCAATGGCTGG | |
| | CGGTAATATTGTTCTGGATATTACCAGCAAGGCCGATAGTTTGAG | |
| | TTCTTCTACTCAGGCAAGTGATGTTATTACTAATCAAAGAAGTAT | |
| | TGCGACAACGGTTAATTTGCGTGATGGACAGACTCTTTTACTCGG | |
| | TGGCCTCACTGATTATAAAAACACTTCTCAGGATTCTGGCGTACC | |
| | GTTCCTGTCTAAAATCCCTTTAATCGGCCTCCTGTTTAGCTCCCGC | |
| | TCTGATTCTAACGAGGAAAGCACGTTATACGTGCTCGTCAAAGCA | |
| | ACCATAGTACGCGCCCTGTAGCGGCGCATTAAGCGCGGCGGGTG | |
| | TGGTGGTTACGCGCAGCGTGACCGCTACACTTGCCAGCGCCCTAG | |
| | CGCCCGCTCCTTTCGCTTTCTTCCCTTCCTTTCTCGCCACGTTCGCC | |
| | ATCTTCAAATATGTATCCGCTCATGAGACAATAACCCTGATAAAT | |
| | GCTTCAATAATATTGAAAAAGGAAGAGTCCTGAGGCGGAAAGAA | |
| | CCAGCTGTGGAATGTGTGTCAGTTAGGGTGTGGAAAGTCCCCAGG | |
| | CTCCCCAGCAGGCAGAAGTATGCAAAGCATGCATCTCAATTAGTC | |
| | AGCAACCAGGTGTGGAAAGTCCCCAGGCTCCCCAGCAGGCAGAA | |
| | GTATGCAAAGCATGCATCTCAATTAGTCAGCAACCATAGTCCCGC | |
| | CCCTAACTCCGCCCATGGCTGACTAATTTTTTTTATTTATGCAGA | |
| | GGCCGAGGCCGCCTCGGCCTCTGAGCTATTCCAGAAGTAGTGAG | |
| | GAGGCTTTTTTGGAGGCCTAGGCTTTTGCAAAGATCGATCAAGAG | |
| | ACAGGATGAGGATCGTTTCGCATGATTGAACAAGATGGATTGCA | |
| | CGCAGGTTCTCCGGCCGCTTGGGTGGAGAGGCTATTCGGCTATGA | |
| | CTGGGCACAACAGACAATCGGCTGCTCTGATGCCGCCGTGTTCCG | |
| | GCTGTCAGCGCAGGGGCGCCCGGTTCTTTTTGTCAAGACCGACCT | |
| | GTCCGGTGCCCTGAATGAACTGCAAGACGAGGCAGCGCGGCTAT | |
| | CGTGGCTGGCCACGACGGGCGTTCCTTGCGCAGCTGTGCTCGACG | |
| | TTGTCACTGAAGCGGGAAGGGACTGGCTGCTATTGGGCGAAGTG | |
| | CCGGGGCAGGATCTCCTGTCATCTCACCTTGCTCCTGCCGAGAAA | |
| | GTATCCATCATGGCTGATGCAATGCGGCGGCTGCATACGCTTGAT | |
| | CCGGCTACCTGCCCATTCGACCACCAAGCGAAACATCGCATCGAG | |
| | CGAGCACGTACTCGGATGGAAGCCGGTCTTGTCGATCAGGATGAT | |
| | CTGGACGAAGAGCATCAGGGGCTCGCGCCAGCCGAACTGTTCGC | |
| | CAGGCTCAAGGCGAGCATGCCCGACGGCGAGGATCTCGTCGTGA | |
| | CCCATGGCGATGCCTGCTTGCCGAATATCATGGTGGAAAATGGCC | |
| | GCTTTTCTGGATTCATCGACTGTGGCCGGCTGGGTGTGGCGGACC | |
| | GCTATCAGGACATAGCGTTGGCTACCCGTGATATTGCTGAAGAGC | |
| | TTGGCGGCGAATGGGCTGACCGCTTCCTCGTGCTTTACGGTATCG | |
| | CCGCTCCCGATTCGCAGCGCATCGCCTTCTATCGCCTTCTTGACGA | |
| | GTTCTTCTGAGCGGGACTCTGGGGTTCGAAATGACCGACCAAGCG | |
| | ACGCCCAACCTGCCATCACGAGATTTCGATTCCACCGCCGCCTTC | |
| | TATGAAAGGTTGGGCTTCGGAATCGTTTTCCGGGACGCCGGCTGG | |
| | ATGATCCTCCAGCGCGGGGATCTCATGCTGGAGTTCTTCGCCCAC | |
| | CCTAGGGGGAGGCTAACTGAAACACGGAAGGAGACAATACCGGA | |

TABLE 1-continued

Examples of Protein and Nucleotide Sequences

| Sequence Description | Sequence | SEQ ID NO |
|---|---|---|
| | AGGAACCCGCGCTATGACGGCAATAAAAAGACAGAATAAAAACG TTGCGCAAACTATTAACTGGCGAACTACTTACTCTAGCTTCCCGG CAACAATTAATAGACTGGATGGAGGCGGATAAAGTTGCAGGACC ACTTCTGCGCTCGGCCCTTCCGGCTGGCTGGTTTATTGCTGATAAA TCTGGAGCCGGTGAGCGTGGGTCTCGCGGTATCATTGCAGCACTG GGGCCAGATGGTAAGCCCTCCCGTATCGTAGTTATCTACACGACG GGGAGTCAGGCAACTATGGATGAACGAAATAGACAGATCGCTGA GATAGGTGCCTCACTGATTAAGCATTGGTAACTGTCAGACCAAGT TTACTCATATATACTTTAGATTGATTTAAAACTTCATTTTTAATTT AAAAGGATCTAGGTGAAGATCCTTTTTGATAATCTCATGACCAAA ATCCCTTAACGTGAGTTTTCGTTCCACTGAGCGTCAGACCCCGTA GAAAAGATCAAAGGATCTTCTTGAGATCCTTTTTTTCTGCGCGTA ATCTGCTGCTTGCAAACAAAAAAACCACCGCTACCAGCGGTGGTT TGTTTGCCGGATCAAGAGCTACCAACTCTTTTTCCGAAGGTAACT GGCTTCAGCAGAGCGCAGATACCAAATACTGTTCTTCTAGTGTAG CCGTAGTTAGGCCACCACTTCAAGAACTCTGTAGCACCGCCTACA TACCTCGCTCTGCTAATCCTGTTACCAGTGGCTGCTGCCAGTGGC GATAAGTCGTGTCTTACCGGGTTGGACTCAAGACGATAGTTACCG GATAAGGCGCAGCGGTCGGGCTGAACGGGGGGTTCGTGCACACA GCCCAGCTTGGAGCGAACGACCTACACCGAACTGAGATACCTAC AGCGTGAGCTATGAGAAAGCGCCACGCTTCCCGAAGGGAGAAAG GCGGACAGGTATCCGGTAAGCGGCAGGGTCGGAACAGGAGAGCG CACGAGGGAGCTTCCAGGGGGAAACGCCTGGTATCTTTATAGTCC TGTCGGGTTTCGCCACCTCTGACTTGAGCGTCGATTTTTGTGATGC TCGTCAGGGGGGCGGAGCCTATGGAAAAACGCCAGCAACGCGGC CTTTTTACGGTTCCTGGCCTTTTGCTGGCCTTTTGCTCACATGTTCT TTCCTGCGTTATCCCTGATTCTGTGGATAACCGTATTACCGCCTT TGAGTGAGCTGATACCGCTCGCCGCAGCCGAACGACCGAGCGCA GCGAGTCAGTGAGCGAGGAAGCGGAAGAGCGCCCAATACGCAA ACCGCCTCTCCCCGCGCGTTGGCCGATTCATTAATG | |
| Human γ-Sarcoglycan amino acid sequence | MVREQYTTATEGICIERPENQYVYKIGIYGWRKRCLYLFVLLLLIILV VNLALTIWILKVMWFSPAGMGHLCVTKDGLRLEGESEFLFPLYAKEI HSRVDSSLLLQSTQNVTVNARNSEGEVTGRLKVGPKMVEVQNQQF QINSNDGKPLFTVDEKEVVVGTDKLRVTGPEGALFEHSVETPLVRAD PFQDLRLESPTRSLSMDAPRGVHIQAHAGKIEALSQMDILFHSSDGM LVLDAETVCLPKLVQGTWGPSGSSQSLYEICVCPDGKLYLSVAGVST TCQEHNHICL | 9 |
| Self-complementary (SC) expression cassette polynucleotide sequence of scAAVrh74.MHCK7.hSGCG | CTGCGCGCTCGCTCGCTCACTGAGGCCGCCCGGGCAAAGCCCGG GCGTCGGGCGACCTTTGGTCGCCCGGCCTCAGTGAGCGAGCGAG CGCGCAGAGAGGGAGTGGCCAACTCCATCACTAGGGGTTCCTTGT AGTTAATGATTAACCCGCCATGCTACTTATCTACGTAGCCATGCT CTAGATTAGGCGCGCCCCTGCAGGACACACAAAAAACCAACACA CAGATCTAATGAAAATAAAGATCTTTTATTGCGGCCCTCGAGTCA CAGACAGATGTGGTTGTGCTCCTGGCATGTGGTAGACACGCCGGC CACGGACAGATACAGCTTGCCATCTGGGCACACGCAGATCTCGTA CAGGCTCTGAGAGGAGCCAGATGGGCCCCATGTGCCCTGCACCA GCTTAGGCAGGCACACGGTCTCGGCATCCAGCACCAGCATGCCGT CGCTAGAGTGGAACAGGATATCCATCTGGCTCAGGGCCTCGATCT TGCCTGCGTGTGCCTGGATGTGCACGCCTCTGGGTGCGTCCATGG ACAGGCTGCGTGTTGGGCTCTCCAGCCTCAGATCCTGAAAAGGGT CTGCGCGCACCAGTGGGGTCTCCACAGAGTGCTCGAACAGGGCG CCCTCAGGTCCTGTCACCCTCAGCTTGTCGGTGCCCACCACCACC TCCTTCTCATCCACTGTAAACAGAGGCTTGCCGTCATTGGAGTTG ATCTGGAACTGCTGATTCTGCACCTCCACCATCTTGGGCCGACC TTCAGTCTGCCGGTCACCTCTCCCTCGCTATTCCTTGCGTTCACTG TCACGTTCTGGGTGGACTGCAGCAGCAGGGAGCTATCCACTCTGC TGTGGATCTCCTTGGCATACAGGGGAAACAGGAACTCAGACTCTC CCTCCAGCCGCAGTCCGTCCTTTGTCACGCACAGGTGTCCCATTC CTGCTGGGGAAAACCACATCACTTTCAGGATCCAGATGGTCAGG GCCAGATTCACCACCAGGATGATCAGCAGCAGCAGCACGAACAG ATACAGACATCTCTTCCGCCAGCCGTAGATGCCGATCTTATACAC GTACTGGTTCTCTGGCCTCTCGATGCAGATTCCCTCGGTTGCTGTG GTGTACTGCTCCCTCACCATGGTGGTACCGGGTACAATTCCGCAG CTTTTAGAGCAGAAGTAACACTTCCGTACAGGCCTAGAAGTAAA GGCAACATCCACTGAGGAGCAGTTCTTTGATTTGCACCACCACCG GATCCGGGACCTGAAATAAAAGACAAAAAGACTAAACTTACCTG GGCGCGCCGCTGGCTGCTCCTGAGTGTCTGTCTGTGCTGTGGAGG TGGTGGTAGAATGAGGGCAGCCCCTGTGCCCCTGGGTTATATAGA GGAGCCTACAGGGTGTGACTAGCCAGGAGGGGCTGTCCCCAGGG AGGGGCCCTGAGAGCAGATGAGCTTTCAGCTCGTTGCCCGGGC ACCGTGCCCACCCCGGACCCAGGCGTGCAGCTTGCCCAGCCCCAT GGCCTTGTATGGGCTGCCCCAAGGGCTGACTTGCTCACTGGTTCC TAAACTAAGTGCTGAGTCTAGCTGGCGGGGACAGCTGGCCCTTC | 10 |

TABLE 1-continued

Examples of Protein and Nucleotide Sequences

| Sequence Description | Sequence | SEQ ID NO |
|---|---|---|
| | GCCGGGAACATGGAACAGTAATACTTTGGGAGTCCCAGGCACGT<br>ATAAGCCCTGGCCCCAAGCCTGTTACAGCCTGCCCTCAGTCCCC<br>CACAGCCTTGTTCGAAGATCTTCGCATGCAGGGGATCCACCAGG<br>ACAGGGTTATTTTTAGAGGCAGCAGGTGTTGGGGGGGGGGGGGC<br>AGCCACATGTCTGGGTTAATTATAACCAGGCATCTCGGGTGTCCC<br>CAGGCCTTGCCTCCTTACATGGGCAGCCTAGACCCGTAGTGGGGC<br>ATGCTAGACAGCAGGGCCCCAAGGTTTGCCCATGAAAGGTCTGTT<br>GCCCTCGCCCCTCTGGCTCCATGGCCTTTTTTTAGTCCTTGGGCAC<br>ATTCCTCCTCCCCAAAGGGCCGATGGGCAGATAGAGGAGAGACA<br>GGAGCGTCTCACACCACCTCCCCTACCCAGGCCCTTACCTCAGTT<br>ATTTTTAATCTGAAGGGTCTAGCTTAGACATGCAAGCTTGCGGCC<br>GCCAATTGGTTAACCCCACTCCCTCTCTGCGCGCTCGCTCGCTCAC<br>TGAGGCCGCCCGGGCAAAGCCCGGGCGTCGGGCGACCTTTGGTC<br>GCCCGGCCTCAGTGAGCGAGCGAGCGCGCAGAGAGGGAGTGGGG<br>TTAACCAATTGGCGGCCGCAAGCTTGCATGTCTAAGCTAGACCCT<br>TCAGATTAAAAATAACTGAGGTAAGGGCCTGGGTAGGGGAGGTG<br>GTGTGAGACGCTCCTGTCTCTCCTCTATCTGCCCATCGGCCCTTTG<br>GGGGAGGAGGAATGTGCCCAAGGACTAAAAAAAGGCCATGGAGC<br>CAGAGGGGCGAGGGCAACAGACCTTTCATGGGCAAACCTTGGGG<br>CCCTGCTGTCTAGCATGCCCCACTACGGGTCTAGGCTGCCCATGT<br>AAGGAGGCAAGGCCTGGGGACACCCGAGATGCCTGGTTATAATT<br>AACCCAGACATGTGGCTGCCCCCCCCCCCCCAACACCTGCTGCCT<br>CTAAAAATAACCCTGTCCCTGGTGGATCCCCTGCATGCGAAGATC<br>TTCGAACAAGGCTGTGGGGGACTGAGGGCAGGCTGTAACAGGCT<br>TGGGGGCCAGGGCTTATACGTGCCTGGGACTCCCAAAGTATTACT<br>GTTCCATGTTCCCGGCGAAGGGCCAGCTGTCCCCCGCCAGCTAGA<br>CTCAGCACTTAGTTTAGGAACCAGTGAGCAAGTCAGCCCTTGGGG<br>CAGCCCATACAAGGCCATGGGGCTGGGCAAGCTGCACGCCTGGG<br>TCCGGGGTGGGCACGGTGCCCGGGCAACGAGCTGAAAGCTCATC<br>TGCTCTCAGGGGCCCCTCCCTGGGGACAGCCCCTCCTGGCTAGTC<br>ACACCCTGTAGGCTCCTCTATATAACCCAGGGGCACAGGGGCTGC<br>CCTCATTCTACCACCACCTCCACAGCACAGACAGACACTCAGGAG<br>CAGCCAGCGGCGCGCCCAGGTAAGTTTAGTCTTTTTGTCTTTTATT<br>TCAGGTCCCGGATCCGGTGGTGGTGCAAATCAAAGAACTGCTCCT<br>CAGTGGATGTTGCCTTTACTTCTAGGCCTGTACGGAAGTGTTACTT<br>CTGCTCTAAAAGCTGCGGAATTGTACCCGGTACCACCATGGTGAG<br>GGAGCAGTACACCACAGCAACCGAGGGAATCTGCATCGAGAGGC<br>CAGAGAACCAGTACGTGTATAAGATCGGCATCTACGGCTGGCGG<br>AAGAGATGTCTGTATCTGTTCGTGCTGCTGCTGCTGATCATCCTG<br>GTGGTGAATCTGGCCCTGACCATCTGGATCCTGAAAGTGATGTGG<br>TTTTCCCCAGCAGGAATGGGACACCTGTGCGTGACAAAGGACGG<br>ACTGCGGCTGGAGGGAGAGTCTGAGTTCCTGTTTCCCCTGTATGC<br>CAAGGAGATCCACAGCAGAGTGGATAGCTCCCTGCTGCTGCAGT<br>CCACCCAGAACGTGACAGTGAACGCAAGGAATAGCGAGGGAGA<br>GGTGACCGGCAGACTGAAGGTCGGCCCCAAGATGGTGGAGGTGC<br>AGAATCAGCAGTTCCAGATCAACTCCAATGACGGCAAGCCTCTGT<br>TTACAGTGGATGAGAAGGAGGTGGTGGTGGGCACCGACAAGCTG<br>AGGGTGACAGGACCTGAGGGCGCCCTGTTCGAGCACTCTGTGGA<br>GACCCCACTGGTGCGCGCAGACCCTTTTCAGGATCTGAGGCTGGA<br>GAGCCCAACACGCAGCCTGTCCATGGACGCACCCAGAGGCGTGC<br>ACATCCAGGCACACGCAGGCAAGATCGAGGCCCTGAGCCAGATG<br>GATATCCTGTTCCACTCTAGCGACGGCATGCTGGTGCTGGATGCC<br>GAGACCGTGTGCCTGCCTAAGCTGGTGCAGGGCACATGGGGCCC<br>ATCTGGCTCCTCTCAGAGCCTGTACGAGATCTGCGTGTGCCCAGA<br>TGGCAAGCTGTATCTGTCCGTGGCCGGCGTGTCTACCACATGCCA<br>GGAGCACAACCACATCTGTCTGTGACTCGAGGGCCGCAATAAAA<br>GATCTTTATTTTCATTAGATCTGTGTGTTGGTTTTTTGTGTGTCCTG<br>CAGGGGCGCGCCTAATCTAGAGCATGGCTACGTAGATAAGTAGC<br>ATGGCGGGTTAATCATTAACTACAAGGAACCCCTAGTGATGGAGT<br>TGGCCACTCCCTCTCTGCGCGCTCGCTCGCTCACTGAGGCCGGGC<br>GACCAAAGGTCGCCCGACGCCCGGGCTTTGCCCGGGCGGCCTCA<br>GTGAGCGAGCGAGCGCGCAG | |
| SGCG Primer 1 | GGA GGA AGC GCT GCC TAT ACC TAT T | 11 |
| SGCG Primer 2 | GGA GGA AGC GCT GCC TAT ACC TAT T | 12 |
| MHCK7 forward primer | CCA ACA CCT GCT GCC TCT AAA | 13 |

TABLE 1-continued

Examples of Protein and Nucleotide Sequences

| Sequence Description | Sequence | SEQ ID NO |
|---|---|---|
| MHCK7 reverse primer | GTC CCC CAC AGC CTT GTT C | 14 |
| MHCK7 intron probe sequence | TGG ATC CCC TGC ATG CGA AGA TC | 15 |

In one embodiment, the vector plasmid comprises a nucleotide sequence that is at least 90%, 95%, or 99% identical to SEQ ID NO: 1, or 7. In one embodiment, the vector plasmid comprises a nucleotide sequence of SEQ ID NO: 1, or 7. The method of generating rAAV, in one embodiment, further comprises transferring a packaging plasmid and/or a helper virus to the host cell. The packaging plasmid, in some embodiments, comprises an AAV rep and/or cap gene that is operably linked to a promoter. The promoter, in one embodiment, is an AAV transcription promoter. In one embodiment, the host cell is a packaging cell. In one embodiment, the packaging cell comprises a stably integrated AAV cap gene. In another embodiment, the packaging cell comprises a stably integrated AAV rep gene.

As used herein, the term "host cell" refers to a cell that can be used to express an exogenous DNA sequence. Non-limiting examples of a host cell comprise a microorganism, a yeast cell, an insect cell, and/or a mammalian cell. The host cell can be used as a recipient for an AAV helper construct, a packaging plasmid, an AAV vector plasmid, an accessary function vector, or other DNA. The term as used here encompasses the progeny of the original cell after expressing the exogenous DNA sequence in the original host cell. Non-limiting examples of host cells for AAV production include Sf9 insect cells and HEK 293T cells. In one embodiment, the cell described herein comprises an insect cell, e.g., a *Drosophila* cell (e.g., an S2 cell or Kc cell), a silkworm cell (e.g., a Bme21 cell), or a mosquito cell (e.g., a C6/36 cell); or a mammalian cell (preferably a human cell, e.g., a human primary cell or an established cell line). In one embodiment, the mammalian cell comprises a 293 cell, a COS cell, a HeLa cells, or a KB cell. The AAV vector plasmid can be introduced to the host cells, e.g., Sf9 or 293T, by infection (virus or baculovirus), transient transfection using reagents (e.g., liposomal, calcium phosphate) or physical means (e.g., electroporation), or other means know in the art. In another embodiment, the host cell lines are stably integrated with the rAAV plasmids into their genomes. Such stable cell lines can be established by incorporating a selection marker into the vector plasmid.

In one embodiment, the host cell is a packaging cell for production of AAV viral particles. Thus, in another aspect, the disclosure provides a host cell that comprises an AAV vector plasmid that comprises a nucleotide sequence that is at least 90%, 95%, or 99% identical to SEQ ID NO: 8. In one embodiment, the AAV vector plasmid that comprises a nucleotide sequence of SEQ ID NO: 8. In another embodiment, the host cell comprises a nucleotide sequence of SEQ ID NO: 1, 7 or 10.

EXAMPLES

Preclinical studies using scAAVrh74.MHCK7.hSGCG are described in International Patent Publication No. WO 2019/152474, which is incorporated by reference herein in its entirety.

Example 1

Materials and Methods

Animal models: WT (C57BL/6J) mice and SGCG−/− mice, with BL6 genetic background, were bred and maintained as homozygous animals under standardized conditions in the Animal Resources Core at the Sarepta Gene Therapy Center of Excellence. Mice were maintained on Teklad Global Rodent Diet (3.8% fiber, 18.8% protein, 5% fat chow) with a 12:12-hour dark:light cycle. All animals were housed in standard mouse cages with food and water ad libitum. For all experiments, mice from both sexes were used: WT (n=6, 5 male [M]/1 female [F]); untreated SGCG−/− (n=6, 4M/2F); low dose (n=6, 6M/0F); mid dose (n=6, 4M/2F); high dose (n=6, 0M/6F).

Genotyping

DNA genotyping was used to identify SGCG−/− mice. DNA from tail clippings was isolated and analyzed by PCR using OneTaq DNA Polymerase (New England Biolabs, Ipswich, MA). A series of primers was used in the PCR analysis to determine the SGCG−/− status. The following primers and conditions were used: GGA GGA AGC GCT GCC TAT ACC TAT T (SEQ ID NO: 11); CAA ATG CTT GCC TCA GGT ATT TC; GCC TGC TCT TTA CTG AAG GCT CTT T (SEQ ID NO: 12). Reactions were carried out on genomic DNA for 30 cycles under the following conditions: 94° C., 30 sec; 58° C., 30 sec; 68° C., 25 sec; followed by 5 min at 68° C.

hSGCG Gene Construction (scAAVrh74.MHCK7.hSGCG) and Vector Production

The full-length human SGCG cDNA (NC_000013.11) was codon-optimized and used for all experiments in this study. The cassette includes a consensus Kozak sequence (CCACC), an SV40 chimeric intron, and synthetic polyadenylation site (53 bp). The muscle specific MHCK7 promoter is used to drive expression. This promoter is well established for enhancing cardiac and diaphragm transgene expression. The SGCG expression cassette was cloned between AAV2 inverted terminal repeats (ITRs) and the cassette was packaged into a AAVrh74 vector using a triple transfection method in the Vector Manufacturing Facility in the Center for Gene Therapy at Nationwide Children's Hospital. The AAVrh74 virus has been shown in mice, non-human primates, and humans to be safe and highly efficient in transducing muscle across the vascular barrier. One of the rate-limiting steps of AAV transduction and subsequent transgene expression is the conversion of the single-stranded vector genome into a double-stranded genome through the synthesis of a cDNA strand. Because of the small size of the SGCG transgene, we are able to bypass this critical rate-limiting step by using a self-complementary vector cassette that packages a double-stranded transgene through complementary base-paring and a mutated hairpin ITR.

Taqman qPCR was used to titer the vector using a primer probe set located in the MHCK7 promoter region. There were no alterations from standard AAV production and purification using this approach. A modified cross-packaging approach, previously reported by Rodino-Klapac et al. (J. Trans. Med. 5:45, 2007), was used to produce the rAAV vector. Here, a triple transfection method with CaPO$_4$ precipitation in HEK293 cells allows for AAV2 ITRs to be packaged into a different AAV capsid serotype. (28,29). The production plasmid is (i) pAAV.MHCK7.hSGCG, (ii) rep2-caprh.74 modified AAV helper plasmids encoding cap serotype 8-like isolate rh.74; and (iii) an adenovirus type 5 helper plasmid (pAdhelper) expressing adenovirus E2A, E4 ORF6 and VA I/II RNA genes. Vectors were purified and encapsidated vg titer (utilizing a Prism 7500 Taqman detector system; PE Applied Biosystems, Carlsbad, CA, USA) was determined. The primer and fluorescent probe targeted the MHCK7 promoter and were as follows: MHCK7 forward primer, 5'-CCA ACA CCT GCT GCC TCT AAA-3' (SEQ ID NO: 13); MHCK7 reverse primer, 5'-GTC CCC CAC AGC CTT GTT C-3'(SEQ ID NO: 14); and MHCK7 probe, 5'-FAM-TGG ATC CCC-Zen-TGC ATG CGA AGA TC-3IABKFQ-3'.

Treatment Cohorts

Systemic delivery was administered via injection of vector into the tail vein of three separate doses of vector or saline in a dose-escalation study. Vector dose calculated based on linear qPCR. Four-week old SGCG−/− mice were injected with 8.94×10$^{10}$ vg total dose (4.63×10$^{12}$ vg/kg; n=6, 6M/0F), 3.63×10$^{11}$ vg total dose (1.85×10$^{13}$ vg/kg; n=6, 4M/2F), or 1.26×10$^{12}$ vg total dose (7.41×10$^{13}$ vg/kg; n=6, 0M/6F) of SCAAVRH74.MHCK7.HSGCG, corresponding to low, mid, and high doses, respectively. Additionally, WT mice (n=6, 5M/1F) and SGCG−/− control mice (n=6, 4M/2F) were injected with saline. Mice were injected at 4-5 weeks of age and euthanized 12 weeks after gene delivery.

The low, mid, and high doses are based on a linearized plasmid as the quantitation standard. The AAV vectors were diluted in saline using a 30 gauge ultra-fine insulin syringe. Mice were restrained in a holding tube placing the tail back through tail slot to warm it up in order dilate the blood vessels for ease of injection. After locating the artery down the center line of the tail, the injection was performed in one of the purple/blue lateral veins that run alongside the tail artery. All treated mice were injected at 4-5 weeks of age and euthanized for observation 12-weeks post-injection. The endpoints include but are not limited to biomarker expression (e.g., immunofluorescence), transduction (e.g., qPCR-vector genomes), histology (e.g., central nucleation, diameters, fibrosis), functions (e.g., activity cage, physiology), and safety (e.g., clinical chemistries).

Tissue Processing

Skeletal muscles were extracted from each mouse, placed on a saline-dampened gauze, then placed on cryo-gel mounted wooden chucks and fresh frozen in cooled methylbutane. Organs were bisected, and one half placed in 10% neutral buffered formalin followed by paraffin embedding for sectioning and hematoxylin and eosin (H&E) staining. The other half of the organ was fresh frozen for subsequent molecular studies.

Biodistribution qPCR Analysis

The presence of test article-specific DNA sequences in muscles and organs were evaluated using a real-time qPCR assay with a vector-specific primer probe sets designed to amplify a sequence of the intronic region directly downstream of the MHCK7 promoter (N=9; n=3 per low-, mid-, and high-dose group). Frozen tissues were sectioned using a cryostat (15 sections at 20-micron thickness) into a pre-chilled microcentrifuge tube. Genomic DNA was isolated using a DNeasy Blood & Tissue Kit according to manufacturer's protocol. The resulting DNA samples were stored at −80° C. until analysis. Test DNA was prepared by diluting each sample to the highest possible concentration of 5 ng/µL or 10 ng/µL in ultrapure sterile water. Standards were prepared using a stock plasmid, starting at a concentration of 1×10$^6$ copies/µL and serially diluted to 10 copies/µL. All samples and standards were analyzed in triplicate. Cycling was performed by an initial denaturing step at 95° C. for 20 seconds followed by 40 cycles of 95° C. for 1 second and 60° C. for 30 seconds. QuantStudio system and software were used to run qPCR. The following primers and probe were used in the study: MHCK7 intron forward primer 5'-CCA ACA CCT GCT GCC TCT AAA-3'(SEQ ID NO: 13), MHCK7 intron reverse primer 5'-GTC CCC CAC AGC CTT GTT C-3'(SEQ ID NO: 14), and MHCK7 intron probe 5'-TGG ATC CCC TGC ATG CGA AGA TC-3' (SEQ ID NO: 15) [5' 6-FAM, 3' Iowa Black® FQ, Internal ZEN® Quencher (Integrated DNA Technologies). The primers and probe were diluted to final concentrations of 100 nM, 100 nM, and 200 nM per reaction, respectively. The standard curve was used to calculate the number of copies in each reaction. To determine the number of vector genome copies per nucleus, the following equation was used:

Copies per nucleus=10^((CT−Std Curve Y Intercept)/Std Curve Slope)*(1000/Amount loaded per well (ng))*(5.98×106)

Immunofluorescence

Transgene expression across muscle tissues and DAPC restoration was assessed using immunofluorescence. Cryosections (12 µm thickness) from the tibialis anterior, gastrocnemius, quadriceps, psoas major, gluteus, triceps, diaphragm, and heart muscles were subjected to immunofluorescence staining for the transgene via our previously used protocol. For γ-sarcoglycan protein detection, sections were incubated with a γ-sarcoglycan rabbit polyclonal primary antibody (Novus, Catalog no. NBP1-59744) at a dilution of 1:100. For α-, β-, and δ-sarcoglycan protein detection, sections were incubated with an α-sarcoglycan rabbit polyclonal antibody (Abcam, Catalog no. ab189254), β-sarcoglycan mouse monoclonal antibody (Leica, Catalog no. B-SARC-L-CE), and δ-sarcoglycan primary antibody, respectively, at a dilution of 1:100. Four random 20× images covering the four different quadrants of the muscle section were taken using a Zeiss (Germany) AxioCam MRCS camera. The percentage of fibers positive for α-, β-, δ-, and γ-sarcoglycan protein staining compared with controls was determined for each image and averaged for each muscle. Fibers counted were defined by the structural appearance of the fiber's cross section. To facilitate scoring, National Institutes of Health (NIH) ImageJ software with the Cell Counter plugin was used to count total fibers. Positive fiber expression was defined as having at least 50% of the fiber staining brighter than the vehicle-treated SGCG−/− saline controls, as previously described. Positive fibers were scored based on the original image exposure; there was no adjustment to the brightness or contrast of any image during the positive image scoring process. The remaining fibers were scored as negative. The test article was blinded at the time of injection. The operator who conducted the injections did not perform any analysis outside of the injection. There is no expression or residual protein in the untreated group, so it is clear which animal received treatment and which did not when observing under the scope, leaving blinding irrelevant for immunofluorescence quantification. To mitigate variability in intensity, images were taken at the same exposure. Quantification data of immunofluorescent-positive fibers expressing α-, δ-, and γ-sarcoglycan proteins are reported as mean±SEM, with 6 mice per treatment group.

Western Blot Analysis

Tissue sections (20 μm thickness, 15 sections) were collected into a microcentrifuge tube and homogenized with 150 μL homogenization buffer (125 mM Tris-HCl, 4% SDS, 4 M urea) in the presence of 1 protease inhibitor cocktail tablet. After homogenization, the samples were centrifuged at 10,000 rpm for 10 min at 4° C., and the resulting supernatant was collected. Protein concentration was determined using the NanoDrop. Protein samples (20 μg) were electrophoresed on a 3-8% polyacrylamide Tris-acetate gel for 70 min at 150V then transferred onto a PVDF membrane for 90 min at 35V. The membrane was blocked in 5% non-fat dry milk in TBST for 1 h, and then incubated in a 1:2000 dilution of a monoclonal rabbit γ-sarcoglycan antibody (Abcam, Catalog no. ab203113) and either a 1:50000 dilution of a mouse α-actinin antibody (Sigma, Catalog no. A7811) or a 1:5000 dilution of a monoclonal rabbit vinculin antibody (Fisher, Catalog no. 700062). Anti-mouse (Sigma, Catalog no. AP308P) and anti-rabbit secondary-HRP antibodies (Invitrogen, Catalog no. 65-6120) were used for ECL immunodetection. Western blot detection and quantification were performed using Alliance Q9 Advanced chemiluminescence imaging system and software. Auto capture mode was used to set the exposure time which varied depending on the intensity of the sample. The volumes of the protein bands were quantified as the sum of all the pixel intensities included in the defined area using the analysis mode of the software and normalized to the corresponding loading control bands. Relative protein expression was determined by dividing by the WT volume ratios.

Morphometric Analysis

H&E staining was performed to visualize muscle morphology, including fiber size and central nucleation on cryosections of muscle (12 μm thickness) from 16-week old WT mice (n=6), SGCG-/- mice (n=6), and SCAAVRH74.MHCK7.HSGCG-treated SGCG-/- mice (n=6 per dose, 12 weeks post-treatment). The percentage of myofibers with central nucleation was determined in the tibialis anterior, gastrocnemius, quadriceps, gluteus, triceps, psoas major, and diaphragm muscles. Additionally, muscle fiber diameters were measured using Feret's diameter in the tibialis anterior, triceps, and gastrocnemius muscles. There was a range of 1600-2000 fibers quantified per muscle from each treatment group and from the control cohort. Four random 20× images per muscle per animal were taken with a Zeiss AxioCam MRCS camera. Centrally nucleated fibers were quantified using NIH ImageJ software, and fiber diameters were measured using Zeiss Axiovision LE4 software.

Histopathology

At necropsy, muscles were fresh frozen in liquid nitrogen-cooled methyl-butane and tissues were stained with H&E. All other organs were harvested and fixed in formalin and embedded in paraffin. Slides and all tissues were sent to GEMPath, Inc, for formal review by a veterinary pathologist.

Masson's Trichrome Stain for Fibrosis Quantification

Frozen muscle tissue sections (12 μm) were mounted on Fisherbrand Superfrost charged microscope slides. Slides were stained and fixed in Bouin's fixative for 60 min, then washed with tap water followed by distilled water until clear. Slides were then incubated in Weigert Iron Hematoxylin Solution for 5 min and washed in running water for 5 min. Slides were rinsed in distilled water before placing in Biebrich Scarlet acid for 2 min and washed in distilled water again. Slides transferred to phosphotungstic phosphomolybidic acid for 10 min, and placed in Aniline Blue for 2 min and washed thoroughly with distilled water. After incubation in acetic acid (1% aqueous solution) for 7 min, the slides were dehydrated in graded ethanol, cleared in xylene, and mounted with coverslips using Cytoseal 60 media from Thermo Fisher Scientific (Waltham, MA, USA; Cat #8310). Images were taken using Gryphax software 2.0.0.68 v with a Jenoptik Prokyon camera mounted on a Nikon Eclipse Ni-U Microscope. Four random 20× images covering the four different quadrants of the muscle section were taken for analysis of Masson's trichrome staining and percent collagen quantification. Thresholds for the contrast between red (muscle) and blue (collagen area) colors were set individually using BIOQUANT Life Sciences software (2019). Using the measure function, the area of collagen and muscle was calculated. The total tissue area was determined by adding the muscle area and collagen area. The percentage of collagen was calculated by dividing the area of collagen by the total tissue area. The mean percentage for each individual was calculated.

Tibialis Anterior Tetanic Contraction for Functional Assessment

The tibialis anterior assessment procedure followed the protocol listed in Hakim et al. Mice were anesthetized with ketamine/xylazine mixture (137.5 mg/kg and 10 mg/kg, respectively) administered intraperitoneally. The hind limb skin was removed to expose the tibialis anterior muscle and patella. The length of muscle is measured after dissection, prior to placement of the mouse, and the length is entered into the software. Care was taken to limit drying of the exposed muscle by constantly hydrating the exposed muscles with a saline-dampened Kimwipe drape. The tibialis anterior distal tendon was then dissected out (left and right side per animal; average of both legs used for analysis [n=12 per cohort]), and a double square knot was tied around the tendon with 4-0 suture as close to the muscle as possible before cutting the tendon. Mice were then transferred to a thermal controlled platform and maintained at 37° C. To stabilize the leg, a metal pin was placed behind the patellar tendon, and the knee was secured to the platform with the tibialis anterior distal tendon sutured to the level arm of the force transducer (Aurora Scientific, Aurora, Canada). An electrode was placed near the sciatic nerve to stimulate it. A warm-up protocol designed by Aurora Scientific was initiated where the resting tension was set at 3-4 g force and maintained for 5 minutes, muscle stimulation at 1 Hz (3 times, 30 sec apart), and an additional muscle stimulation at 150 Hz (3 times, 60 sec apart). Once the muscle was stabilized, the resting tension was set to a length (optimal length) where twitch contractions were maximal. After a 3-min rest period, the tibialis anterior muscle was stimulated at 50, 100, 150 and 200 Hz, allowing a 1-min rest between each stimulus. Following a 5-min rest, the muscles were then subjected to a series of 10 isometric contractions, occurring at 1-min intervals with a 10% stretch-lengthening procedure. The duration of tetanic contraction lasts 200 mins. After the eccentric contractions, the mice were euthanized, and both tibialis anterior muscles were dissected and frozen for histology and molecular studies.

Formulas:

Tibialis anterior limb-specific force=absolute force/cross sectional area

Absolute force=Force at 150 Hz*9.8 (9.8 mN=1 gram)

Cross sectional area=muscle weight (mg)/1.06 (muscle density)*length (mm)*1 muscle weight (g)/[tibialis anterior limb muscle fiber length (cm)×1.06 (g/cm3)]

Diaphragm Tetanic Contraction for Functional Assessment

Mice were euthanized and the diaphragm was dissected with rib attachments and central tendon intact and placed in Kreb's-Henseleit (K-H) buffer (118 mM NaCl, 4.7 mM KCl, 1.2 mM $MgSO_4$, 1.25 mM $CaCl_2$), 1.2 mM $KH_2PO_4$, 25 mM $NaHCO_3$, 11 mM glucose) as previously described. A 2-4 mm wide section of diaphragm was isolated per animal per cohort (n=6). Diaphragm strips were tied firmly with braided surgical silk (6/0; Surgical Specialties, Reading, PA) at the central tendon and sutured through a portion of rib bone affixed to the distal end of the strip. Each muscle was transferred to a water bath filled with oxygenated K-H solution that was maintained at 37° C. The muscles were aligned horizontally and tied directly between a fixed pin and a dual-mode force transducer-servomotor (305C; Aurora Scientific, Aurora, Ontario, Canada). Two platinum plate electrodes were positioned in the organ bath so as to flank the length of the muscle. The muscle was stretched to optimal length for measurement of twitch contractions and then allowed to rest for 10 min before initiation of the tetanic protocol. Once the muscle was stabilized, it was set to an optimal length of 1 g and subjected to a warm-up, which consisted of three 1-Hz twitches every 30 sec followed by three 150-Hz twitches every minute. After a 3-min rest period, the diaphragm was stimulated at 20, 50, 80, 120, 150, 180 Hz, allowing a 2-min rest period between each stimulus, each with a duration of 250 ms to determine maximum tetanic force. Muscle length and weight were measured, and the force was normalized for muscle weight and length.

Formulas:

Diaphragm-specific force=absolute force at 150 Hz/cross sectional area

Absolute force=force at 150 Hz*9.8 (9.8 mN=1 gram)

Cross sectional area=muscle weight (g)/[diaphragm fiber length (cm)×1.06 (g/cm3)]

Laser Monitoring of Open-Field Cage Activity

To assess the level of physical activity, SGCG−/− and WT mice were subjected to an open-field activity protocol similar to that used in previous reports. An open-field activity chamber was used to determine the overall activity of the experimental mice. Mice at 4 weeks of age from the WT (n=6, 5M/1F) and untreated SGCG−/− (n=6, 4M/2F) control groups, along with SCAAVRH74.MHCK7.HSGCG-treated SGCG−/− mice (low dose [n=6, 6M/0F]; mid dose [n=6, 4M/2F]; high dose [n=6, 0M/6F]) were subjected to analysis following a previously described protocol, with several modifications. Mice were treated at 4 weeks of age, with an endpoint age of 12 weeks post-treatment. Cohorts were injected one week apart from one another to eliminate variability in endpoint age. Sessions were broken down by cohort. All mice were tested at the same time of day, between the hours of 6:10 AM and 8:30 AM, when mice are most active. All mice were tested in an isolated room under dim light and with the same handler each time. To reduce anxiety and minimize behavioral variables that could potentially affect normal activity of the mice and consequently the results of the assay, we tested mice that were not individually housed. Mouse activity was monitored using the Photobeam activity system (San Diego Instruments, San Diego, CA). This system uses a grid of invisible infrared light beams that traverse the animal chamber front to back and left to right to monitor the position and movement of the mouse within an x-y-z plane. Activity was recorded for 1-hour cycles at 5-min intervals. Mice were acclimatized to the activity test room for an initial 1-hour session 3 and 4 days before data acquisition began. Mice were tested in individual chambers. The testing equipment was cleaned between each use to reduce mouse reactionary behavioral variables that could alter results. The data were converted to a Microsoft Excel worksheet, and all calculations were done within the Excel program. Individual beam breaks for movement in the x and y planes were added up for each mouse to represent total ambulation, and beam breaks in the z plane were added up to obtain vertical activity within the 1-hour time interval.

Serum Chemistry and Hematology

As a measure of safety, blood chemistries and hematology studies were performed on vector-dosed SGCG−/− and WT mice. Whole blood was retrieved from cardiac puncture from treated WT and SGCG−/− mice. Blood was collected in a serum separating tube and centrifuged for 10 min at 3,500 rpm. Serum was collected, frozen, and sent to Nationwide Children's Hospital for processing and assessment of aspartate aminotransferase (AST) and alanine aminotransferase (ALT) liver enzyme levels.

Serum Creatine Kinase Measurement

Levels of creatine kinase were measured in the sera of WT mice (n=6), untreated SGCG−/− Lactate Ringer's solution (LR) treated mice (n=6), and SCAAVRH74.MHCK7.HSGCG-treated SGCG−/− mice at mid and high doses (n=6) (low dose data were not collected due to insufficient sample volume) using the creatine kinase SL Assay according to manufacturer's protocol (Sekisui Diagnostics; Charlottetown, PE, Canada; catalog no. 326-10). Briefly, 25 µL of serum was mixed with 1 mL of the working reagents and added to a cuvette. A kinetic assay was set on the spectrophotometer to measure the absorbance at 340 nm every 30 sec for 180 sec. Creatine kinase levels were calculated using the absorbance readings and the equation listed below:

$$U/L=[(\Delta Abs./min)*1.025*1000]/[1*6.22*0.025]=(\Delta Abs./min)*6592.$$

Statistical Analysis

Statistical analysis was performed using GraphPad Prism 7.01 software. Data were expressed as the mean±SEM (error bars). One-way ANOVA with Tukey's multiple comparisons test was performed for analysis of blood chemistries, serum creatine kinase, diaphragm and tibialis anterior physiology, and cage activity. Two-way ANOVA with Tukey's multiple comparisons test was performed for analysis of central nucleation and eccentric contraction. Kruskal-Wallis test with Dunn's multiple comparisons test was performed for analysis of fiber diameter.

Figure 2A:
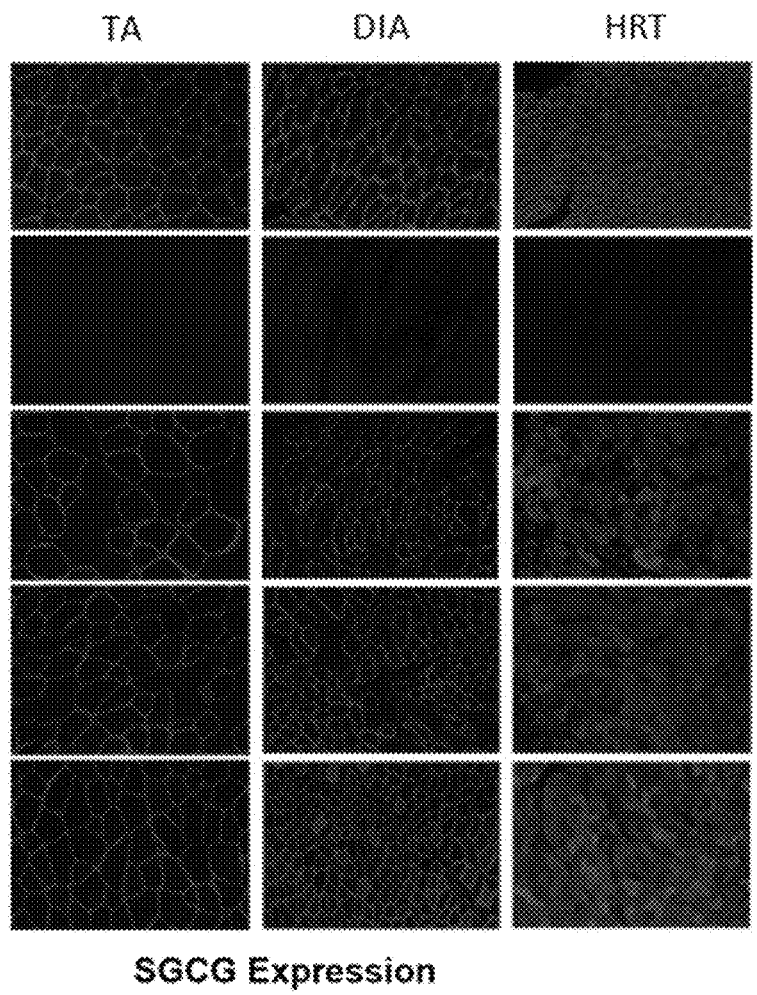
FIGS. 2A and 2B demonstrates human γ-sarcoglycan expression in skeletal muscle.
Figure 2B:
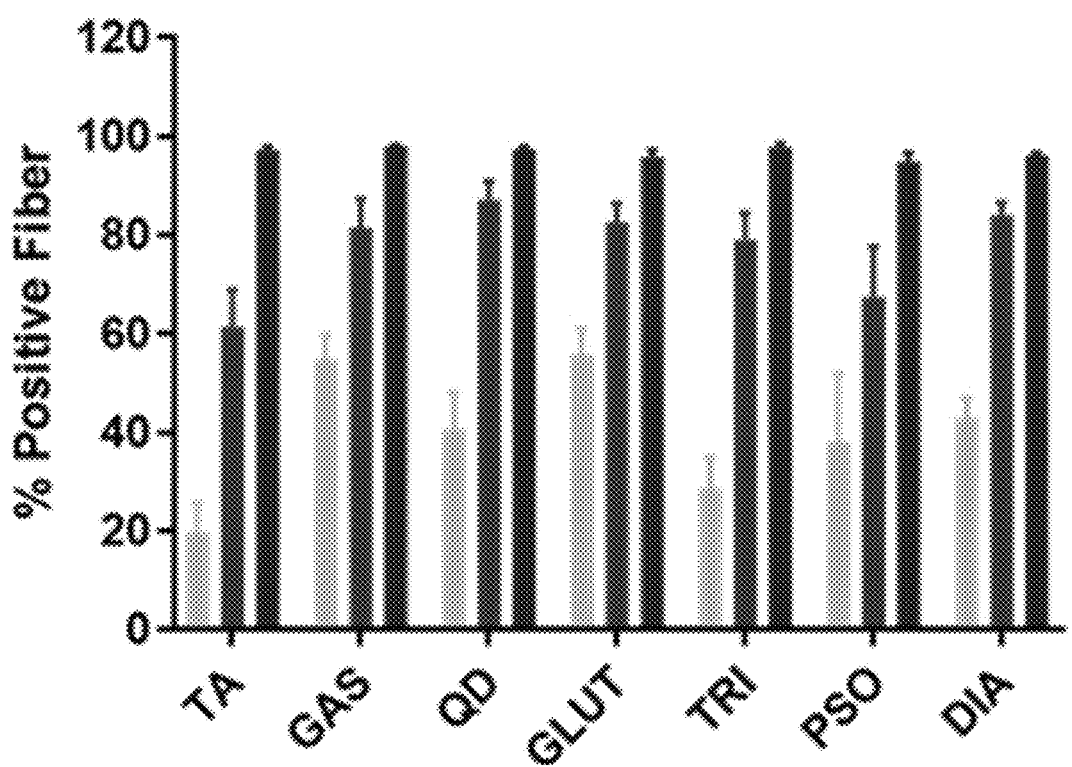

A single systemic injection of SCAAVRH74.MHCK7.hSGCG resulted in successful systemic delivery as shown by biodistribution of vector genome copies (FIG. 1). The IV administration of scAAVrh74.MHCK7.hSGCG AAV vector to SGCG−/− mice in the presence of significant histopathology in the muscle resulted in transgene expression throughout tibialis anterior (TA) limb, DIA, and HRT muscles across doses (FIGS. 2A and 2B).

Figure 3A:
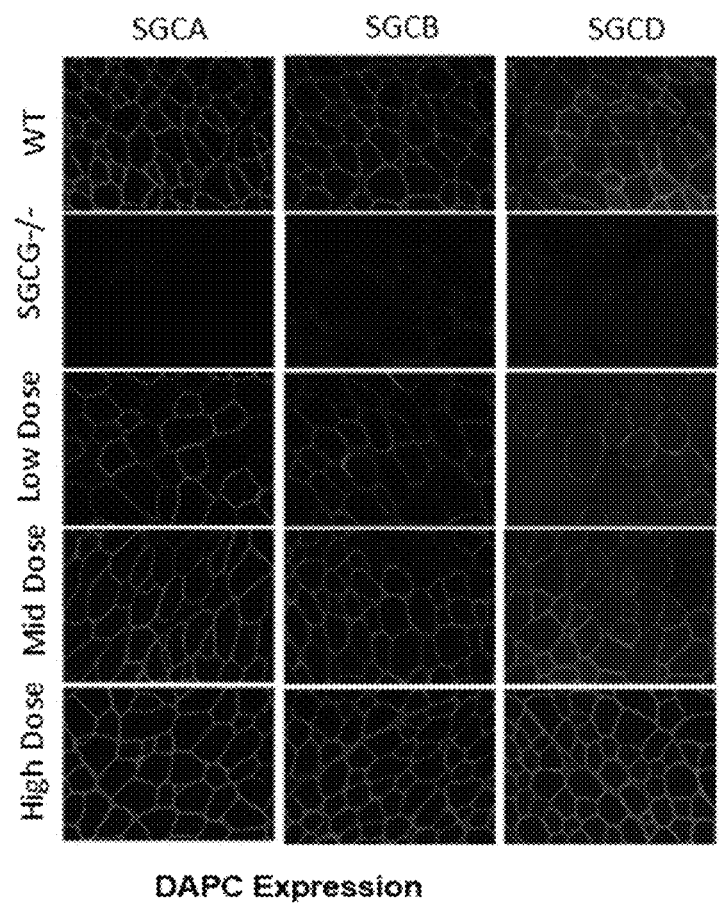
FIGS. 3A and 3B shows restoration of DAPC proteins in SGCBSGCG–/– mice intravenously injected with low-dose, mid-dose, and high-dose scAAVrh.74.MHCK7.hSGCBSGCG.
Figure 3B:
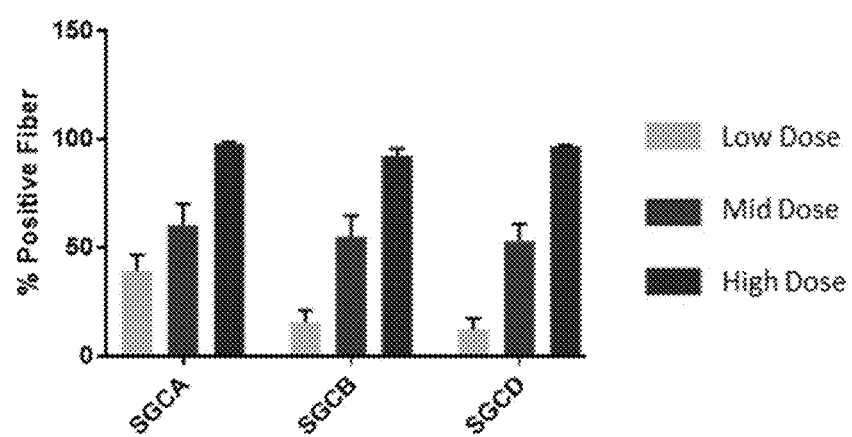

Also, administration of scAAVrh74.MHCK7.hSGCG vector to SGCG−/− mice in the presence of significant histopathology in the muscle resulted in dose-dependent restoration of DAPC proteins at the sarcolemma (FIGS. 3A and 3B). In particular, before treatment SGCG−/− mice show absent or reduced sarcolemma expression of α-sarcoglycan (SGCA), β-sarcoglycan (SGCB), and δ-sarcoglycan (SGCD) (FIGS. 3A and 3B). Treatment with scAAVrh74.MHCK7.hSGCG vector increased SGCA, SGCB, and SGCD subunit expression at the sarcolemma in SGCG−/− mice as measured by immunofluorescent percent-positive fibers (FIGS. 3A and 3B).

Figure 4A:
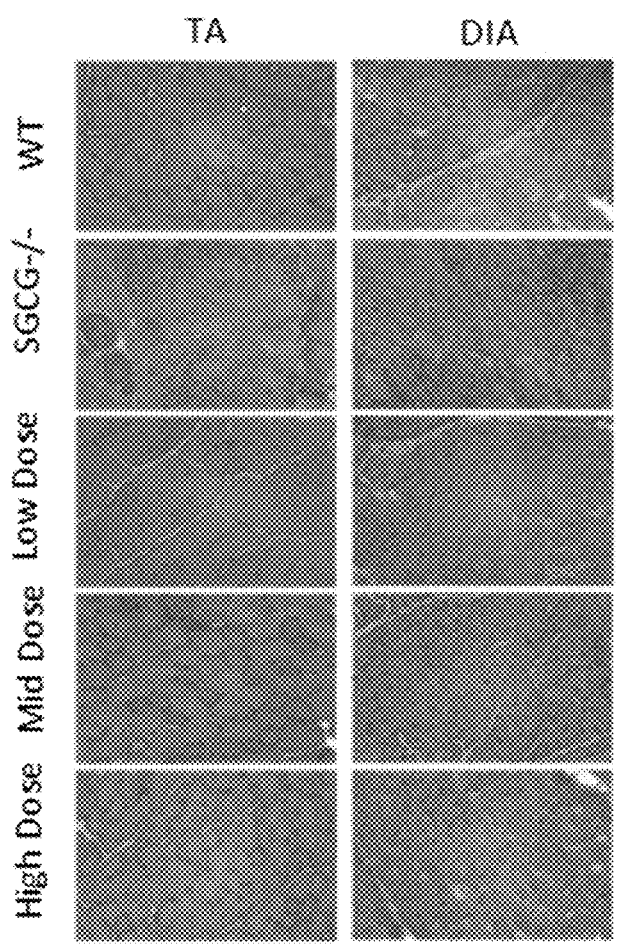
FIGS. 4A-4D demonstrates the effect of systemic treatment with scAAVrh74.MHCK7.hSGCG on muscle pathology.
Figure 4B:
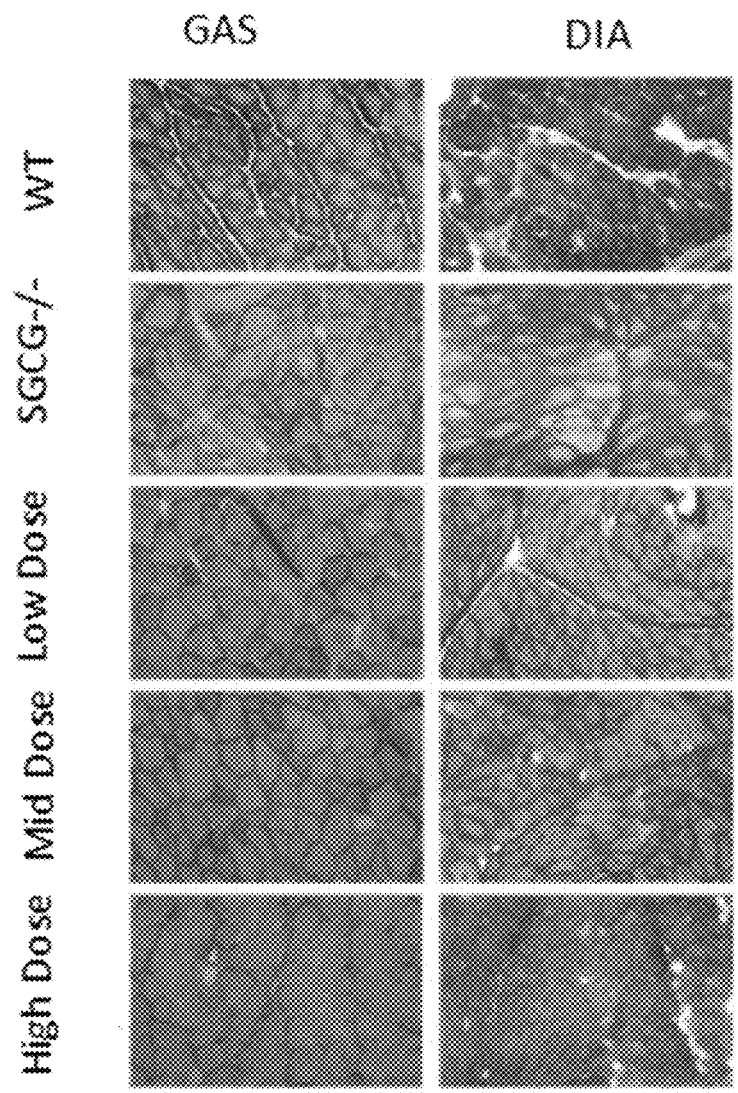
Figure 4C:
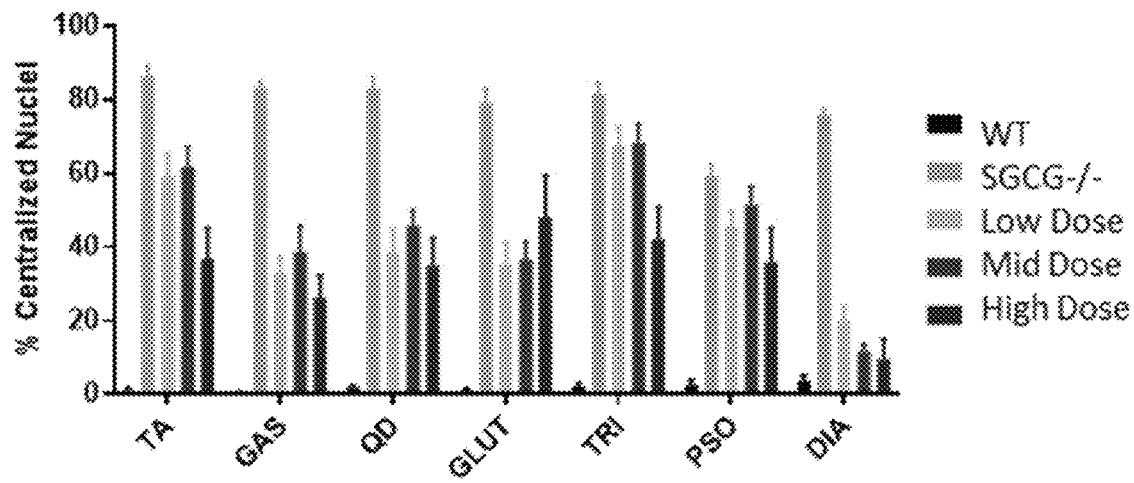
Figure 4D:
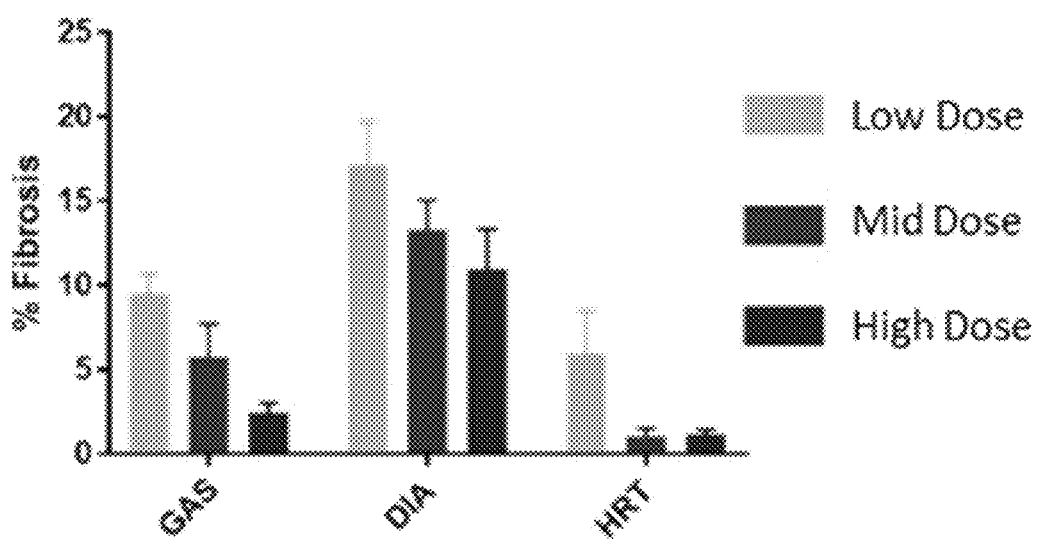

SGCG−/− mice presented significant histopathology in the muscle with high levels of central nucleation compared to WT. After treatment with scAAVrh74.MHCK7.hSGCG, overall muscle pathology improved and decreases in central nuclei were observed (FIG. 4A). Overall fibrotic tissue deposition improved and there was a reduction in levels of fibrosis as dosage escalated compared with levels in untreated SGCG−/− mice (FIGS. 4A-4D).

Figure 5A:
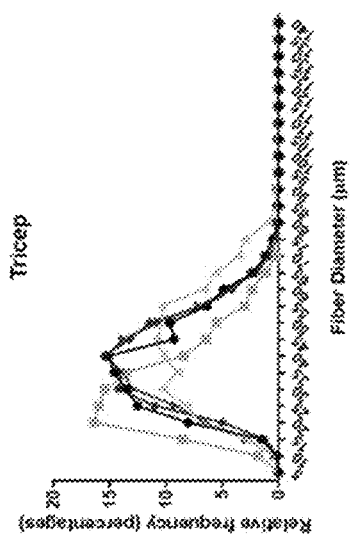
FIGS. 5A, 5B and 5C demonstrates quantitive muscle morphometrics in skeletal muscles from BL/6 WT, SGCG–/–, and scAAVrh.74.MHCK7.hSGCG treated mice at low-dose, mid-dose, and high-dose.
Figure 5B:
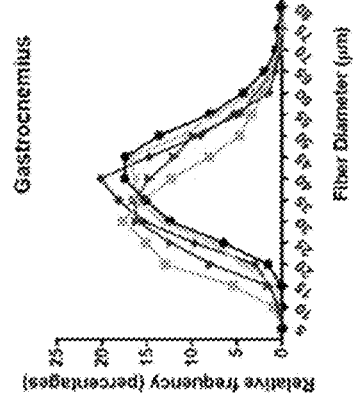
Figure 5C:
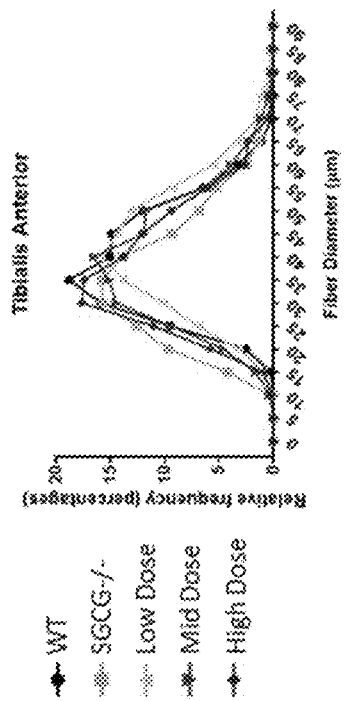
Figure 6A:
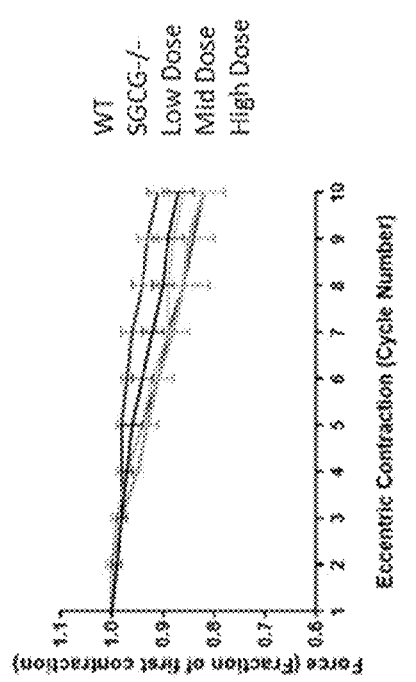
FIGS. 6A, 6B and 6C demonstrates protection of force output in mice following treatment with scAAVrh.74.MHCK7.hSGCG at low-dose, mid-dose, and high-dose.
Figure 6B:
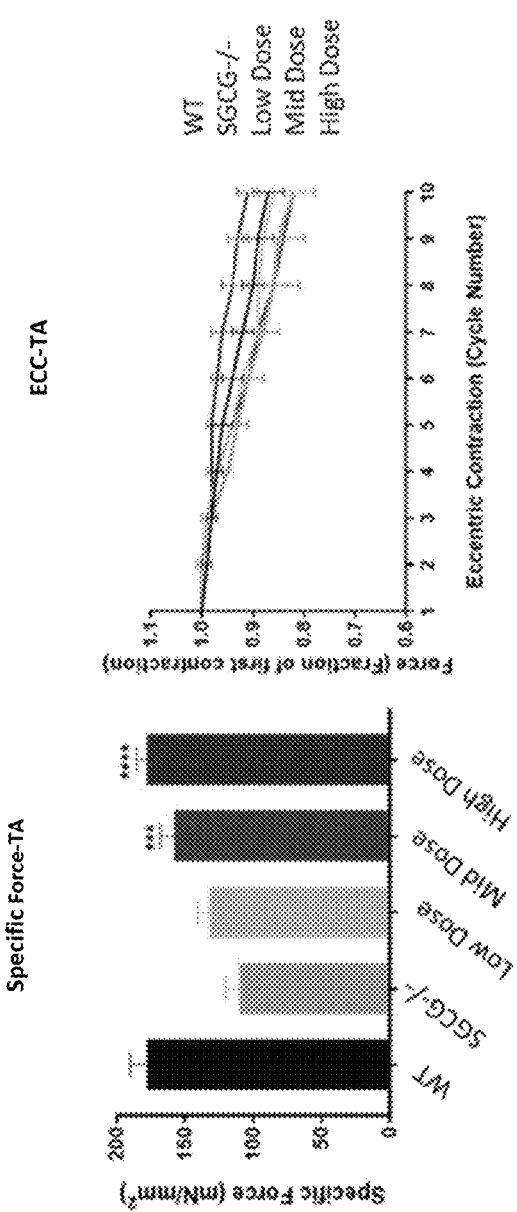
Figure 6C:
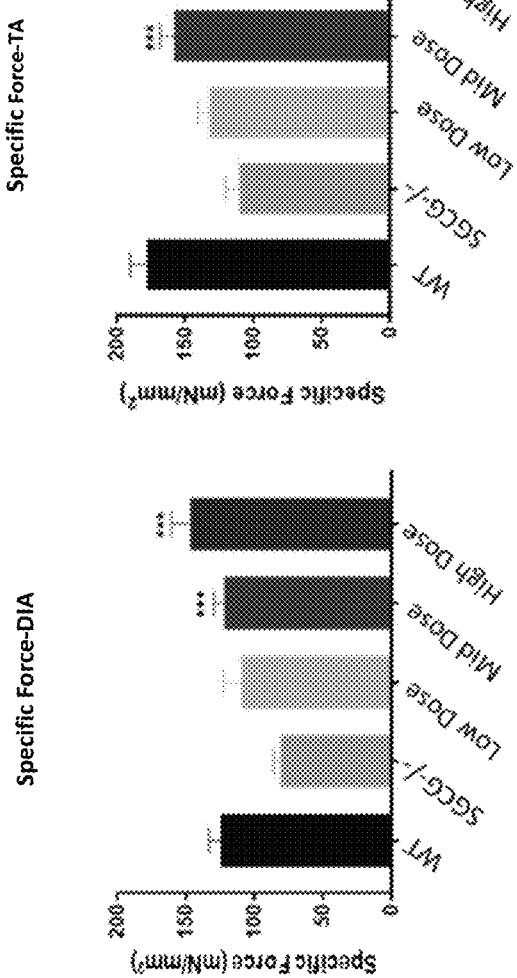

An increase in fiber diameter in all three dosages was seen, indicating normalized fiber size similar to WT fibers in TA, gastrocnemius (GAS), and triceps (TRI) muscles (FIGS. 5A, 5B and 5C). Functional improvement was observed with significantly increased muscle strength (force production) and resistance to contraction-induced injury in the TA and DIA muscles (FIGS. 6A, 6B and 6C). Deficits in specific force and resistance to contraction-induced injury were identified in the tibialis anterior and in specific force in the diaphragm muscles of SGCG−/− mice compared with WT mice. Mid- and high-dose scAAVrh74.MHCK7.hSGCG treatment significantly improved specific force in both muscles compared with untreated SGCG−/− mice (tibialis anterior: low dose p=0.571, mid dose p=0.008, high dose p=0.0001; diaphragm: low dose p=0.388, mid dose p=0.088, high dose p=0.001; (FIGS. 6A, 6B and 6C). Numerical improvement in eccentric contraction was also observed with high dose treatment.

A reduction in ambulation and vertical rearing in the SGCG−/− mouse model compared with WT controls was observed (FIGS. 7A and 7B). Laser-monitoring of open-field cage activity showed increased ambulation and movement in SRP-9005-treated SGCG−/− mice.

The treatment was associated with a decrease in CK levels. Liver enzymes (ALT and AST) returned within the normal limits for mice after treatment (FIGS. 8A, 8B and 8C). Quantitative muscle morphometrics showed an increase in fiber diameter at all three dosages, indicating normalized fiber size similar to WT fibers in tibialis anterior, gastrocnemius, and triceps muscles (Table 2).

TABLE 2

Muscle fiber diameters from quantitative muscle morphometrics

| Muscle | WT | SCGC-/- | Low Dose | Mid Dose | High Dose |
|---|---|---|---|---|---|
| Tibialis anterior, μm | 39.31 (0.24) | 36.14 (0.31) | 42.79 (0.34) | 39.56 (0.30) | 38.05 (0.26) |
| Gastrocnemius, μm | 41.80 (0.26) | 33.28 (0.26) | 40.00 (0.29) | 36.92 (0.27) | 37.96 (0.23) |
| Triceps muscles, μm | 38.52 (0.31) | 31.91 (0.29) | 43.83 (0.49) | 39.09 (0.31) | 39.52 (0.29) |

(Values are mean (SEM). SEM=standard error of the mean)

Western Blot Analysis. Gamma-Sarcoglycan

Figure 10A:
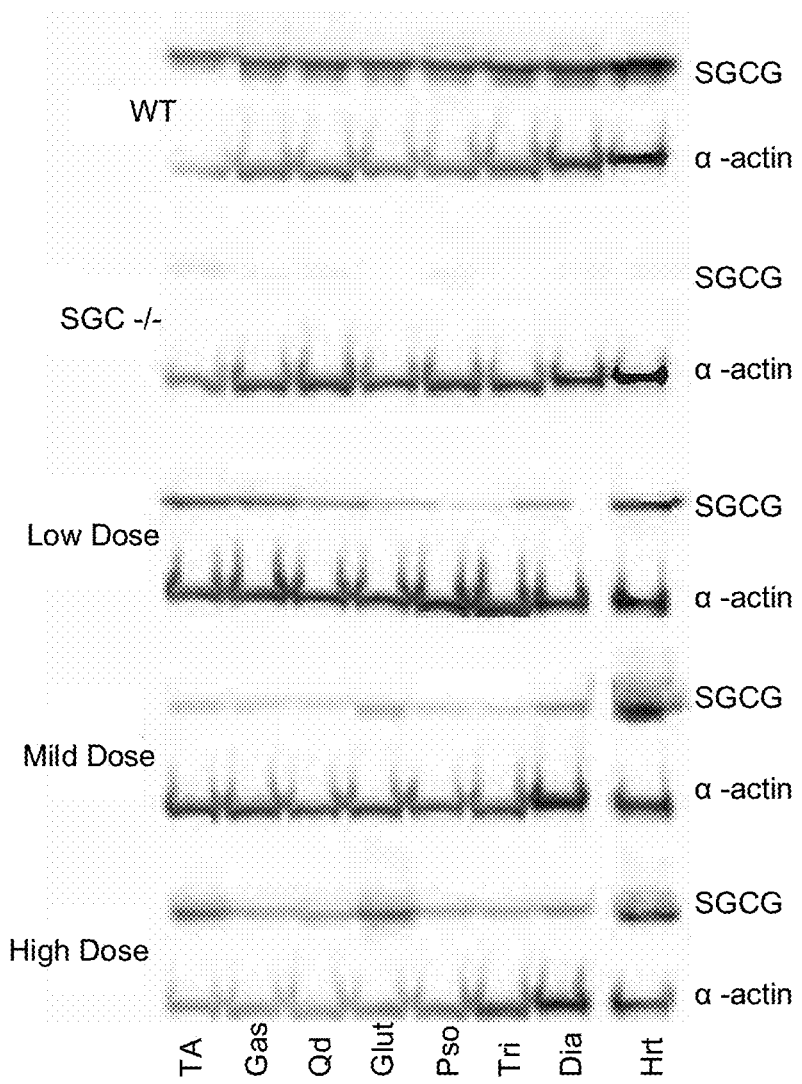
FIG. 10A shows the Western blot assay confirming γ-sarcoglycan protein expression across muscle tissues in treated mice.
Figure 10B:
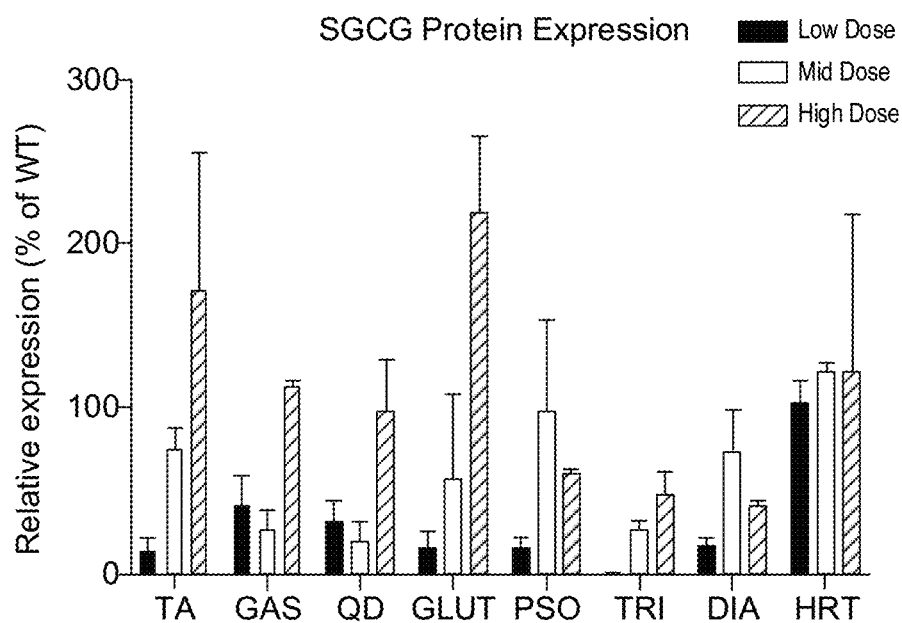
FIG. 10B shows relative expression of SGCG protein in treated mice as compared to the wide-type mice.

Western blot confirmed γ-sarcoglycan protein expression across muscle tissues in treated mice at the lowest dose (FIG. 10A). γ-sarcoglycan expression was dose-dependent and remained at least 100% of wild type (WT) expression in the heart for the low, mid, and high doses (FIG. 10B).

While the present disclosure has been described in terms of specific embodiments, it is understood that variations and modifications will occur to those skilled in the art. Accordingly, only such limitations as appear in the claims should be placed on the disclosure.

All documents referred to in this application are hereby incorporated by reference in their entirety.

What is claimed is:

1. A method of treating muscular dystrophy in a subject in need thereof, comprising the step of administering a recombinant adeno-associated virus (rAAV) scAAVrh74.MHCK7.hSGCG to the subject, wherein the rAAV is administered using a systemic route of administration and at a dose of about $4.63 \times 10^{12}$ vg/kg, about $1.85 \times 10^{13}$ vg/kg, or about $7.41 \times 10^{13}$ vg/kg based on a linearized plasmid as the quantitation standard, and wherein the rAAV comprises a nucleotide sequence that is identical to SEQ ID NO: 7 or SEQ ID NO: 10.

2. The method of claim 1, wherein the level of gamma-sarcoglycan gene expression in a cell of the subject is increased after administration of the rAAV as compared to the level of gamma-sarcoglycan gene expression before administration of the rAAV;
   wherein the average rAAV copy number in a muscle cell of the treated subject is at least 0.01 copy per nucleus;
   wherein the centralized nuclei percentage and/or the fibrosis is reduced in the muscle of the treated subject as compared to the level before administration of the rAAV;
   wherein motor function is improved in said subject as compared to the motor function of said subject before administration of the rAAV;
   wherein the North Star Assessment for Dysferlinopathies (NSAD) are increased in said subject as compared to the NSAD of said subject before administration of the rAAV; and/or
   wherein the ALT and AST levels are reduced in said subject as compared to the ALT and AST levels of said subject before administration of the rAAV.

3. The method of claim 2, wherein the motor function is improved by at least 5%, 10%, 15%, 20%, 25%, 30%, 40%, 45%, or 50%.

4. The method of claim 2, wherein the level of gamma-sarcoglycan protein expression is increased by at least 30, 31, 32, 33, 34, 35, 36, 37, 38, 39, or 40% after administration of the rAAV as compared to the gamma-sarcoglycan protein level before administration of the rAAV.

5. The method of claim 1, wherein the rAAV is administered using an intravenous route.

6. The method of claim 1, wherein the muscular dystrophy is limb-girdle muscular dystrophy.

7. The method of claim 1, wherein the number of gamma-sarcoglycan positive fibers in the muscle tissue of the subject is increased by at least 40, 41, or 42% after administration of the rAAV as compared to the number of gamma-sarcoglycan positive fibers before administration of the rAAV.

8. The method of claim 1, wherein the serum CK level in the subject is decreased by at least 82, 83, 84, 85, 86, 87, 88, 89, or 90% by 60 days to 90 days, 60 days, or 90 days after administration of the rAAV as compared to the serum CK level before administration of the rAAV.

9. The method of claim 1, wherein the level of alpha-sarcoglycan and/or beta-sarcoglycan in the subject is increased after administration of the rAAV as compared to the level of alpha-sarcoglycan and/or beta-sarcoglycan before administration of the rAAV.

10. The method of claim 1, wherein the rAAV is administered at a dose of about $4.63 \times 10^{12}$ vg/kg based on a linearized plasmid as the quantitation standard.

11. The method of claim 1, wherein the rAAV is administered at a dose of about $1.85 \times 10^{13}$ vg/kg based on a linearized plasmid as the quantitation standard.

12. The method of claim 1, wherein the rAAV is administered at a dose of or about $7.41 \times 10^{13}$ vg/kg based on a linearized plasmid as the quantitation standard.

13. The method of claim 1, wherein the rAAV comprises the nucleotide sequence of SEQ ID NO: 7.

14. The method of claim 1, wherein the rAAV comprises the nucleotide sequence of SEQ ID NO: 10.

* * * * *